United States Patent
Yamaguchi et al.

(10) Patent No.: US 8,921,028 B2
(45) Date of Patent: *Dec. 30, 2014

(54) SALT, RESIST COMPOSITION AND METHOD FOR PRODUCING RESIST PATTERN

(75) Inventors: Satoshi Yamaguchi, Osaka (JP); Koji Ichikawa, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 42 days.

This patent is subject to a terminal disclaimer.

(21) Appl. No.: 13/414,267

(22) Filed: Mar. 7, 2012

(65) Prior Publication Data

US 2012/0231392 A1 Sep. 13, 2012

(30) Foreign Application Priority Data

Mar. 8, 2011 (JP) ................... 2011-049969

(51) Int. Cl.

| | | |
|---|---|---|
| G03F 7/004 | (2006.01) | |
| G03F 7/028 | (2006.01) | |
| G03F 7/029 | (2006.01) | |
| C07C 309/04 | (2006.01) | |
| C07C 309/06 | (2006.01) | |
| C07C 309/13 | (2006.01) | |
| C07D 327/08 | (2006.01) | |
| G03F 7/039 | (2006.01) | |
| G03F 7/20 | (2006.01) | |

(52) U.S. Cl.
CPC .............. *C07D 327/08* (2013.01); *G03F 7/029* (2013.01); *C07C 309/13* (2013.01); *C07C 309/06* (2013.01); *C07C 309/04* (2013.01); *G03F 7/00405* (2013.01); *G03F 7/0046* (2013.01); *G03F 7/0397* (2013.01); *G03F 7/2041* (2013.01); *Y10S 430/121* (2013.01); *Y10S 430/123* (2013.01)
USPC ........ 430/270.1; 430/326; 430/920; 430/922; 568/22; 568/24

(58) Field of Classification Search
USPC .............. 430/270.1, 325, 326, 920, 921, 925; 549/16, 17, 26, 43; 544/145; 546/197; 548/526; 568/22, 24
See application file for complete search history.

(56) References Cited

U.S. PATENT DOCUMENTS

| | | |
|---|---|---|
| 6,200,728 B1 | 3/2001 | Cameron et al. |
| 6,203,965 B1 | 3/2001 | Cameron et al. |
| 6,749,987 B2 | 6/2004 | Kodama et al. |
| 6,803,169 B2 | 10/2004 | Cameron et al. |
| 7,435,526 B2 | 10/2008 | Kodama et al. |
| 7,615,330 B2 | 11/2009 | Kamimura et al. |
| 7,776,512 B2 | 8/2010 | Kodama et al. |
| 7,812,194 B2 | 10/2010 | Kodama et al. |
| 7,851,130 B2 | 12/2010 | Kawanishi et al. |
| 8,084,183 B2 | 12/2011 | Yamashita et al. |
| 2001/0038970 A1 | 11/2001 | Cameron et al. |
| 2002/0102491 A1 | 8/2002 | Kodama et al. |
| 2005/0130060 A1 | 6/2005 | Kodama et al. |
| 2007/0003871 A1 | 1/2007 | Kodama et al. |
| 2007/0224540 A1 | 9/2007 | Kamimura et al. |
| 2008/0081288 A1 | 4/2008 | Kawanishi et al. |
| 2008/0085468 A1 | 4/2008 | Kamimura et al. |
| 2009/0047598 A1 | 2/2009 | Yamashita et al. |
| 2009/0148791 A1 | 6/2009 | Kodama et al. |
| 2010/0255419 A1 | 10/2010 | Kodama et al. |
| 2011/0171576 A1 | 7/2011 | Yamaguchi et al. |
| 2011/0201823 A1* | 8/2011 | Yoshida et al. ............ 548/334.1 |
| 2011/0318688 A1* | 12/2011 | Hiraoka et al. ............ 430/270.1 |

FOREIGN PATENT DOCUMENTS

| | | |
|---|---|---|
| JP | 7-333851 A | 12/1995 |
| JP | 2000-241965 A | 9/2000 |
| JP | 2002-214774 A | 7/2002 |
| JP | 2006-215271 A | 8/2006 |
| JP | 2007-086516 A | 4/2007 |

(Continued)

OTHER PUBLICATIONS

Machine translation of JP 2012-031145, published on Feb. 16, 2012.*

*Primary Examiner* — Anca Eoff

(74) *Attorney, Agent, or Firm* — Birch, Stewart, Kolasch & Birch, LLP

(57) ABSTRACT

A salt represented by the formula (I) and a resist composition containing the salt are provided,

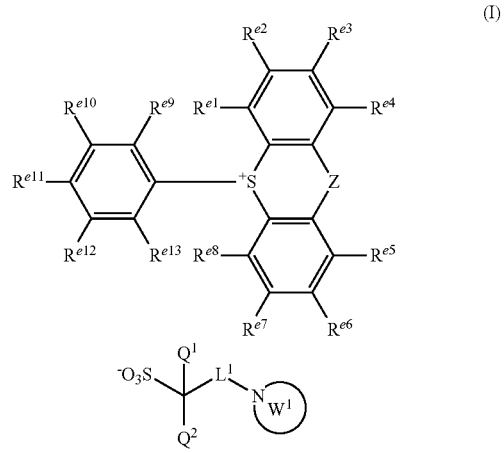

wherein $Q^1$, $Q^2$, $L^1$, ring $W^1$, $R^{e1}$, $R^{e2}$, $R^{e3}$, $R^{e4}$, $R^{e5}$, $R^{e6}$, $R^{e7}$, $R^{e8}$, $R^{e9}$, $R^{e10}$, $R^{e11}$, $R^{e12}$, $R^{e13}$ and Z are defined in the specification.

9 Claims, No Drawings

(56) References Cited

FOREIGN PATENT DOCUMENTS

| | | |
|---|---|---|
| JP | 2007-171649 A | 7/2007 |
| JP | 2007-178858 A | 7/2007 |
| JP | 2007-210904 A | 8/2007 |
| JP | 2007-232769 A | 9/2007 |
| JP | 2007-293249 A | 11/2007 |
| JP | 2007-293250 A | 11/2007 |
| JP | 2008-100988 A | 5/2008 |
| JP | 2008-107817 A | 5/2008 |
| JP | 2009-037057 A | 2/2009 |
| JP | 2009-053518 A | 3/2009 |
| JP | 2009-053665 A | 3/2009 |
| JP | 2009-058949 A | 3/2009 |
| JP | 2009-069381 A | 4/2009 |
| JP | 2011-037839 A | 2/2011 |
| JP | 2012-031145 * | 2/2012 |

* cited by examiner

SALT, RESIST COMPOSITION AND METHOD FOR PRODUCING RESIST PATTERN

CROSS-REFERENCE TO RELATED APPLICATIONS

This application claims priority to Japanese Application No. 2011-49969 filed on Mar. 8, 2011. The entire disclosures of Japanese Application No. 2011-49969 is incorporated hereinto by reference.

BACKGROUND OF THE INVENTION

1. Field of the Invention

The present invention relates to a salt, a resist composition and a method for producing resist pattern.

2. Background Information

Recently, a triarylsulfonium cation-containing salt is used as an acid generator for a resist composition which is used for ArF exposure and is now actively advanced development for semiconductor microfabrication. Examples of such salt include a salt represented by the formula below,

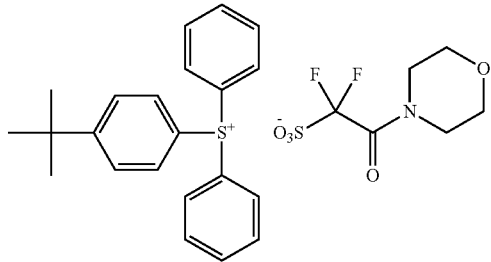

which is described in Patent document of JP-2002-214774A.

However, with the resist composition containing the conventional salt as an acid generator, the focus margin (DOE) at producing a resist pattern may be not always satisfied with.

SUMMARY OF THE INVENTION

The present invention provides following inventions of <1> to <9>.

<1> A salt represented by the formula (I),

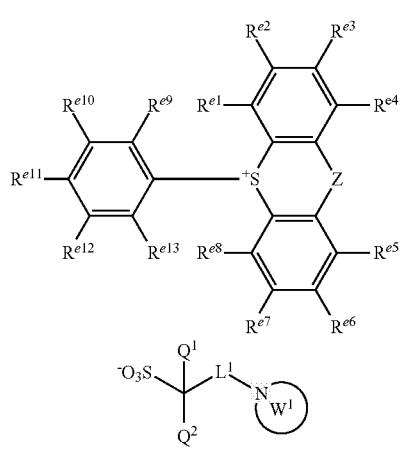

(I)

wherein $Q^1$ and $Q^2$ independently represent a fluorine atom or a $C_1$ to $C_6$ perfluoroalkyl group;

$L^1$ represents *—CO—O-$L^a$- or *—$CH_2$—O-$L^b$-, * represents a bond to —$CQ^1Q^2$, $L^a$ and $L^b$ independently represent a $C_1$ to $C_{15}$ divalent saturated aliphatic hydrocarbon group, and one or more —$CH_2$— contained in the divalent saturated aliphatic hydrocarbon group may be replaced by —O— or —CO—;

ring $W^1$ represents a $C_2$ to $C_{36}$ heterocyclic ring, and one or more —$CH_2$— contained in the heterocyclic ring may be replaced by —O—;

$R^{e1}$, $R^{e2}$, $R^{e3}$, $R^{e4}$, $R^{e5}$, $R^{e6}$, $R^{e7}$, $R^{e8}$, $R^{e9}$, $R^{e10}$, $R^{e11}$, $R^{e12}$ and $R^{e13}$ independently represent a hydrogen atom, a halogen atom, a hydroxy group, a $C_1$ to $C_{12}$ hydrocarbon group or carboxyl group, or two of $R^{e1}$, $R^{e2}$, $R^{e3}$, $R^{e4}$, $R^{e5}$, $R^{e6}$, $R^{e7}$, $R^{e8}$, $R^{e9}$, $R^{e10}$, $R^{e11}$, $R^{e12}$ and $R^{e13}$, which two respectively bond to adjacent carbon atoms, may form a ring together with two carbon atoms bonded thereto, and one or more —$CH_2$— contained in the hydrocarbon group may be replaced by —O— or —CO—;

Z represents a single bond or a divalent linking group.

<2> The salt according to <1>, wherein Z in the formula (I) is a oxygen atom.

<3> The salt according to <1> or <2>, wherein $L^1$ in the formula (I) is a *—CO—O-$L^a$, wherein $L^a$ is defined as <1>.

<4> An acid generator comprising the salt according to any one of <1> to <3>.

<5> A resist composition comprising the acid generator according to <4>, and a resin.

<6> The resist composition according to <5>, wherein the resin is insoluble or poorly soluble in alkali aqueous solution, but becoming soluble in an alkali aqueous solution by the action of an acid.

<7> The resist composition according to <5> or <6>, which further comprises a basic compound.

<8> The resist composition according to any one of <5> to <7>, which further comprises a solvent.

<9> A method for producing resist pattern comprising steps of;

(1) applying the resist composition of <5> onto a substrate;

(2) drying the applied composition to form a composition layer;

(3) exposing the composition layer;

(4) heating the exposed composition layer, and (5) developing the heated composition layer.

DETAILED DESCRIPTION OF THE PREFERRED EMBODIMENTS

<Definition>

In the present specification, any group exemplified below is applicable to any of the chemical formulae having a similar group with optionally selecting the number of carbon atoms, unless otherwise specified. The number attached to "C" means the carbon number of each group. When a group can form linear and branched chain and/or cyclic structures, all structures are included and may simultaneously present in one group, unless otherwise specified. When one group or moiety takes a stereoisomeric form, all stereoisomeric forms are included. Each group can form monovalent, or di- or more-valent group depending on the bonded position and bonding form.

A hydrocarbon group includes an aliphatic hydrocarbon group and an aromatic group. The aliphatic hydrocarbon group includes a chain aliphatic hydrocarbon group, an alicyclic hydrocarbon group and a combination thereof.

Examples of a monovalent chain aliphatic hydrocarbon group include methyl, ethyl, propyl, butyl, pentyl, hexyl, heptyl, octyl, decyl, dodecyl, hexadecyl, pentadecyl, hexyldecyl, heptadecyl and octadecyl groups. The aliphatic hydrocarbon group may be any of a liner and a branched chain aliphatic hydrocarbon groups. The chain aliphatic hydrocarbon group may include a carbon-carbon double bond, but a saturated chain aliphatic hydrocarbon group, i.e., alkyl group, is preferable.

Examples of a divalent chain aliphatic hydrocarbon group include a group in which one hydrogen atom is removed from the above the monovalent chain aliphatic hydrocarbon group, i.e., alkanediyl group.

The cyclic aliphatic hydrocarbon group may be any of a monocyclic or a polycyclic aliphatic hydrocarbon groups. The cyclic aliphatic hydrocarbon group hereinafter is sometimes referred to as "alicyclic hydrocarbon group". The alicyclic hydrocarbon group may include a carbon-carbon double bond, but a saturated alicyclic hydrocarbon group is preferable.

Examples of a monovalent alicyclic hydrocarbon group include a group in which one hydrogen atom is removed from an alicyclic hydrocarbon. Examples of a divalent alicyclic hydrocarbon group include a group in which two hydrogen atoms are removed from the alicyclic hydrocarbon group.

Examples of the alicyclic hydrocarbon typically include a cycloalkane below.

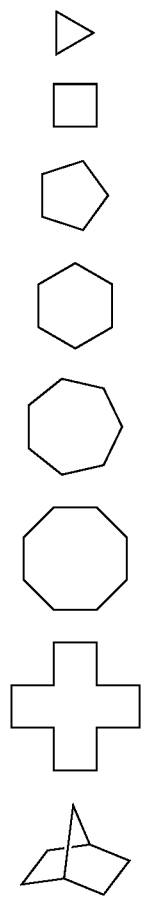

(KA-1)
(KA-2)
(KA-3)
(KA-4)
(KA-5)
(KA-6)
(KA-7)
(KA-8)

-continued

 (KA-9)

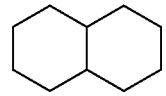 (KA-10)

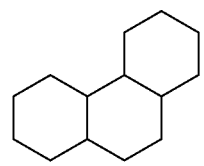 (KA-11)

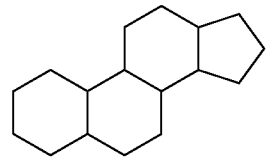 (KA-12)

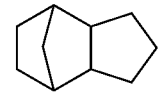 (KA-13)

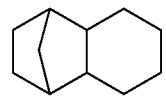 (KA-14)

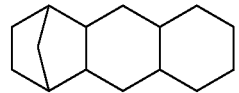 (KA-15)

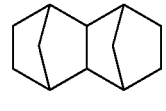 (KA-16)

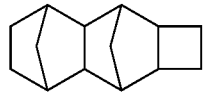 (KA-17)

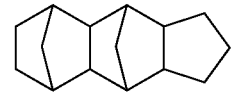 (KA-18)

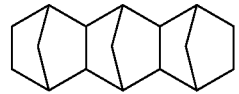 (KA-19)

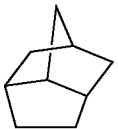 (KA-20)

 (KA-21)

(KA-22)

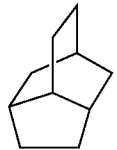

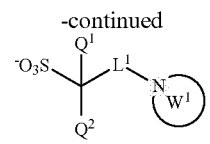

Examples of the aromatic hydrocarbon group typically include an aryl group such as phenyl, naphthyl, anthryl, biphenyl, phenanthryl and fluorenyl groups.

The aliphatic hydrocarbon group and the aromatic hydrocarbon group may be substituted with a substituent.

Typical examples of the substituent of the aliphatic hydrocarbon group include a halogen atom, an alkoxy group, an acyl group, an aryl group, an aralkyl group and an aryloxy group.

Typical examples of the substituent of the aromatic hydrocarbon group include a halogen atom, an alkoxy group, an acyl group, an alkyl group and an aryloxy group.

Examples of the halogen atom include fluorine, chlorine, bromine and iodine atoms.

Examples of the alkoxyl group include methoxy, ethoxy, propoxy, butoxy, pentyloxy, hexyloxy, heptyloxy, octyloxy, decyloxy and dodecyloxy groups. The alkoxyl group may be any of a liner and a branched chain alkoxyl groups.

Examples of the acyl group include a group bonding a carbonyl group to the alkyl group, such as, acetyl, propionyl, butyryl, valeryl, hexylcarbonyl, heptylcarbonyl, octylcarbonyl, decylcarbonyl and dodecylcarbonyl groups, and a group bonding a carbonyl group to the aryl group, such as, benzoyl group. The alkyl group in the acyl group may be any of a liner and a branched chain alkyl groups.

Examples of the aryloxy group include a group bonding an oxygen atom to the above aryl group.

Examples of the aralkyl group include benzyl, phenethyl, phenylpropyl, naphthylmethyl and naphthylethyl groups.

"(meth)acrylic monomer" means at least one monomer having a structure of "$CH_2=CH-CO-$" or "$CH_2=C(CH_3)-CO-$", as well as "(meth)acrylate" and "(meth)acrylic acid" mean "at least one acrylate or methacrylate" and "at least one acrylic acid or methacrylic acid", respectively.

<Salt (I)>

The salt of the present invention is represented by the formula (I) below (hereinafter is sometimes referred to as "salt (I)"),

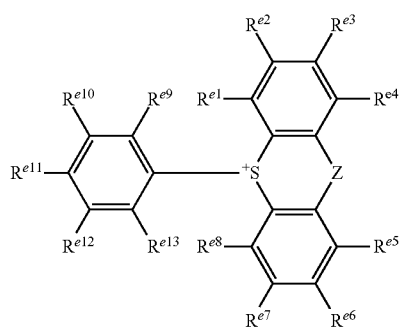

wherein $Q^1$ and $Q^2$ independently represent a fluorine atom or a $C_1$ to $C_6$ perfluoroalkyl group;

$L^1$ represents *—CO—O—$L^a$- or *—$CH_2$—O—$L^b$-, * represents a bond to —$CQ^1Q^2$, $L^a$ and $L^b$ independently represent a $C_1$ to $C_{15}$ divalent saturated aliphatic hydrocarbon group, and one or more —$CH_2$— contained in the divalent saturated aliphatic hydrocarbon group may be replaced by —O— or —CO—;

ring $W^1$ represents a $C_2$ to $C_{36}$ heterocyclic ring, and one or more —$CH_2$— contained in the heterocyclic ring may be replaced by —O—;

$R^{e1}$, $R^{e2}$, $R^{e3}$, $R^{e4}$, $R^{e5}$, $R^{e6}$, $R^{e7}$, $R^{e8}$, $R^{e9}$, $R^{e10}$, $R^{e11}$, $R^{e12}$ and $R^{e13}$ independently represent a hydrogen atom, a halogen atom, a hydroxy group, a $C_1$ to $C_{12}$ hydrocarbon group or carboxyl group, or two of $R^{e1}$, $R^{e2}$, $R^{e3}$, $R^{e4}$, $R^{e5}$, $R^{e6}$, $R^{e7}$, $R^{e8}$, $R^{e9}$, $R^{e10}$, $R^{e11}$, $R^{e12}$ and $R^{e13}$, which two respectively bond to adjacent carbon atoms, may form a ring together with two carbon atoms bonded thereto, and one or more —$CH_2$— contained in the hydrocarbon group may be replaced by —O— or —CO—;

Z represents a single bond or a divalent linking group.

Z represents a single bond or a divalent linking group.

Hereinafter a cation constituting the salt (I) is sometimes referred to as "cation (I)" and an anion constituting the salt (I) is sometimes referred to as "anion (I)".

Examples of the perfluoroalkyl group of $Q^1$ and $Q^2$ include trifluoromethyl, perfluoroethyl, perfluoropropyl, perfluoroisopropyl, perfluorobutyl, perfluoro-sec-butyl, perfluoro-tert-butyl, perfluoropentyl and perfluorohexyl groups.

Among these, $Q^1$ and $Q^2$ independently are preferably trifluoromethyl or fluorine atom, and more preferably a fluorine atom.

The divalent saturated aliphatic hydrocarbon group of $L^a$ and $L^b$ include any of a linear chain, a branched chain, a mono-alicyclic or a poly-alicyclic hydrocarbon group. Among these, $L^a$ and $L^b$ are preferably a $C_4$ to $C_{15}$ divalent saturated aliphatic hydrocarbon group, more preferably a $C_5$ to $C_{15}$ divalent saturated aliphatic hydrocarbon group, and more preferably a $C_6$ to $C_{15}$ divalent saturated aliphatic hydrocarbon group, in particular, $L^a$ and $L^b$ are preferably a chain hydrocarbon group and an aliphatic hydrocarbon group, more preferably a $C_5$ to $C_{12}$ chain hydrocarbon group and a $C_5$ to $C_{12}$ aliphatic hydrocarbon group, and still more preferably a $C_5$ to $C_{12}$ chain hydrocarbon group. Here, one or more —$CH_2$— contained in the divalent saturated aliphatic hydrocarbon group may be replaced by —O— or —CO—, the number of carbon atom means the number of that before replacing by —O— or —CO—.

Examples of *—CO—O—$L^a$- in which one or more —$CH_2$— contained in the divalent saturated aliphatic hydrocarbon group of $L^a$ is replaced by —O— or —CO— include a group represented by the formula (L1-2),

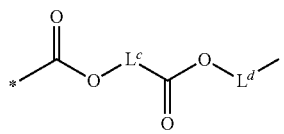

(L1-2)

wherein $L^c$ and $L^d$ independently represent a $C_1$ to $C_{12}$ divalent saturated aliphatic hydrocarbon group.

Examples of *—$CH_2$—O-$L^b$- in which one or more —$CH_2$— contained in the divalent saturated aliphatic hydrocarbon group of $L^b$ is replaced by —O— or —CO— preferably include a group represented by the formula (L1-4),

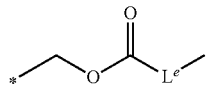

(L1-4)

wherein $L^e$ represent a $C_1$ to $C_{14}$ divalent saturated hydrocarbon group. Among these, $L^e$ is preferably a $C_6$ to $C_{13}$ divalent saturated hydrocarbon group.

In the formula (L1-2) and the formula (L1-4), the group is represented so as to correspond with two sides of the formula (I), that is, the left side of the group bonds to $C(Q^1)(Q^2)$- and the right side of the group bonds to a nitrogen atom (examples of the formula below are the same as above). * represents a bond.

Examples of the divalent group represented by the formula —CO—O-$L^a$- include groups below.

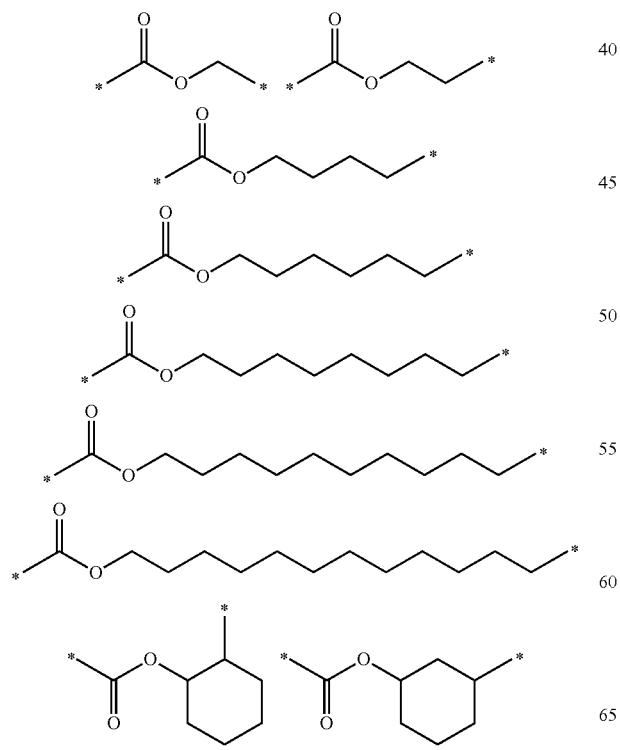

Examples of the divalent group represented by the formula (L1-2) include groups below.

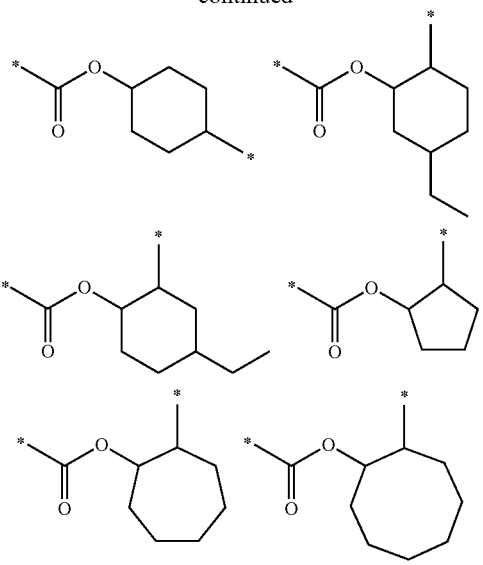

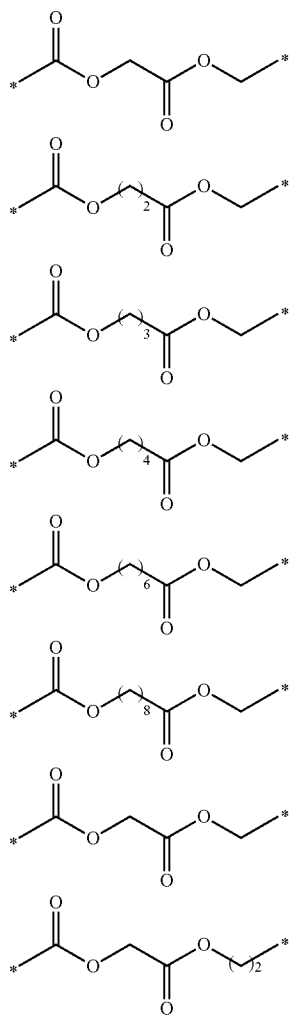

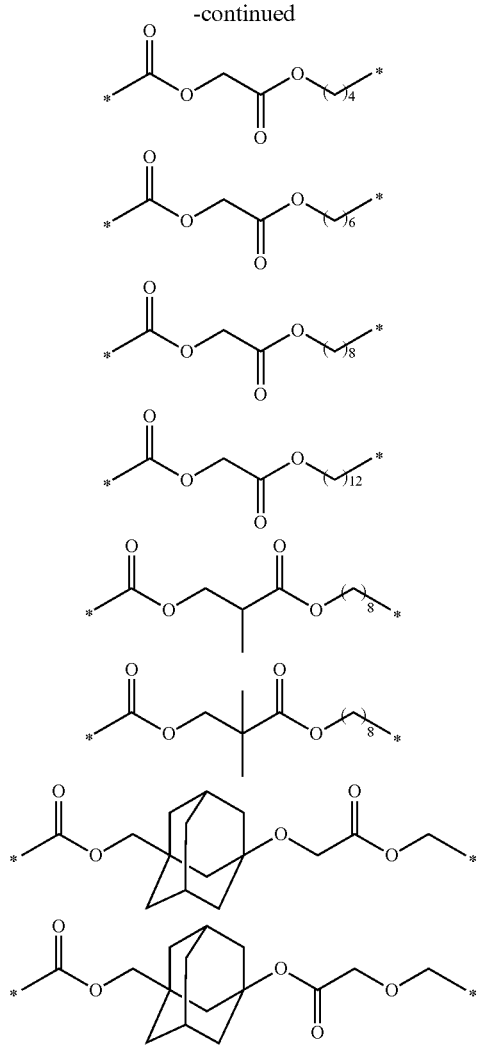
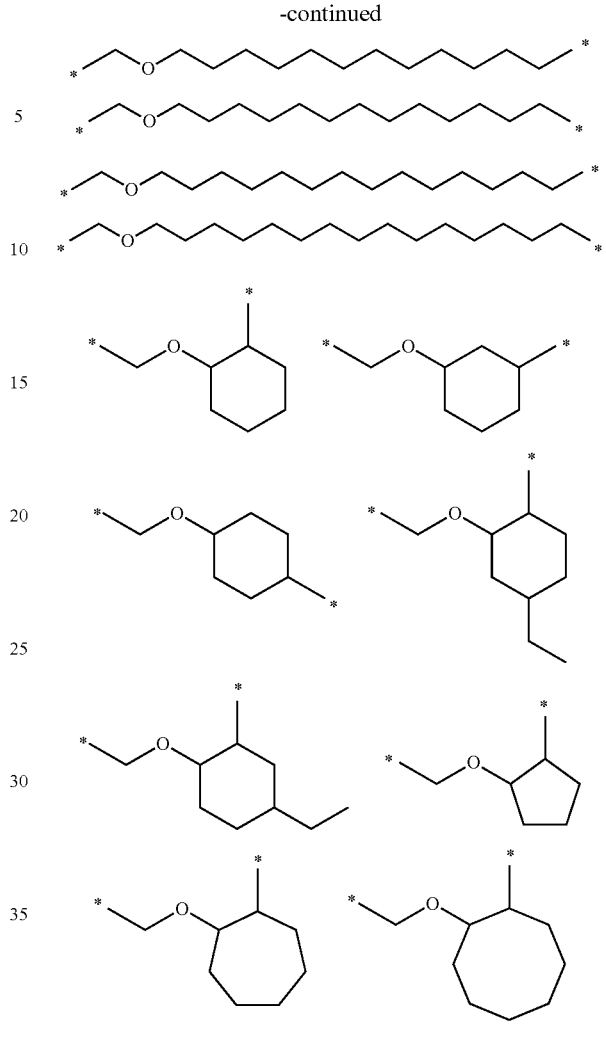
Examples of the divalent group represented by the formula *—CH$_2$—O-L$^b$- include groups below.
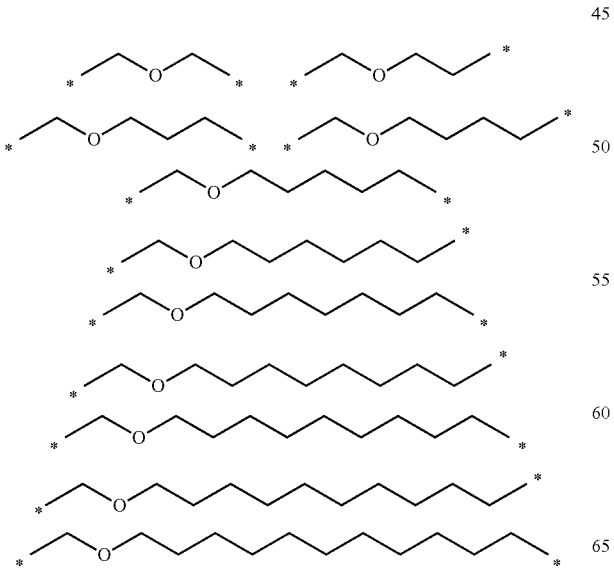
Examples of the divalent group represented by the formula (L1-4) include groups below.
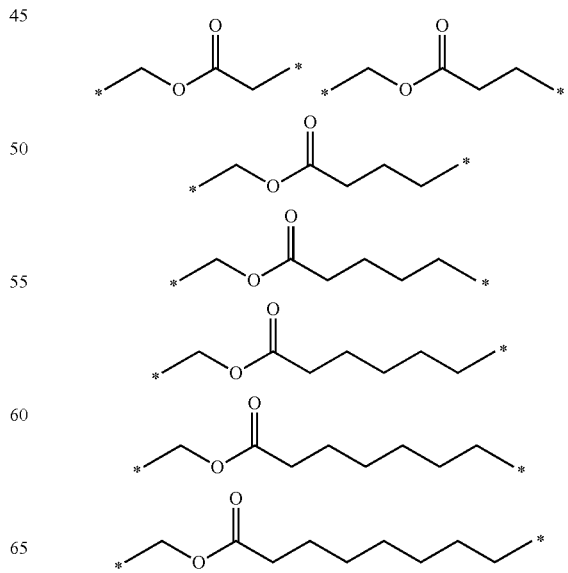

-continued

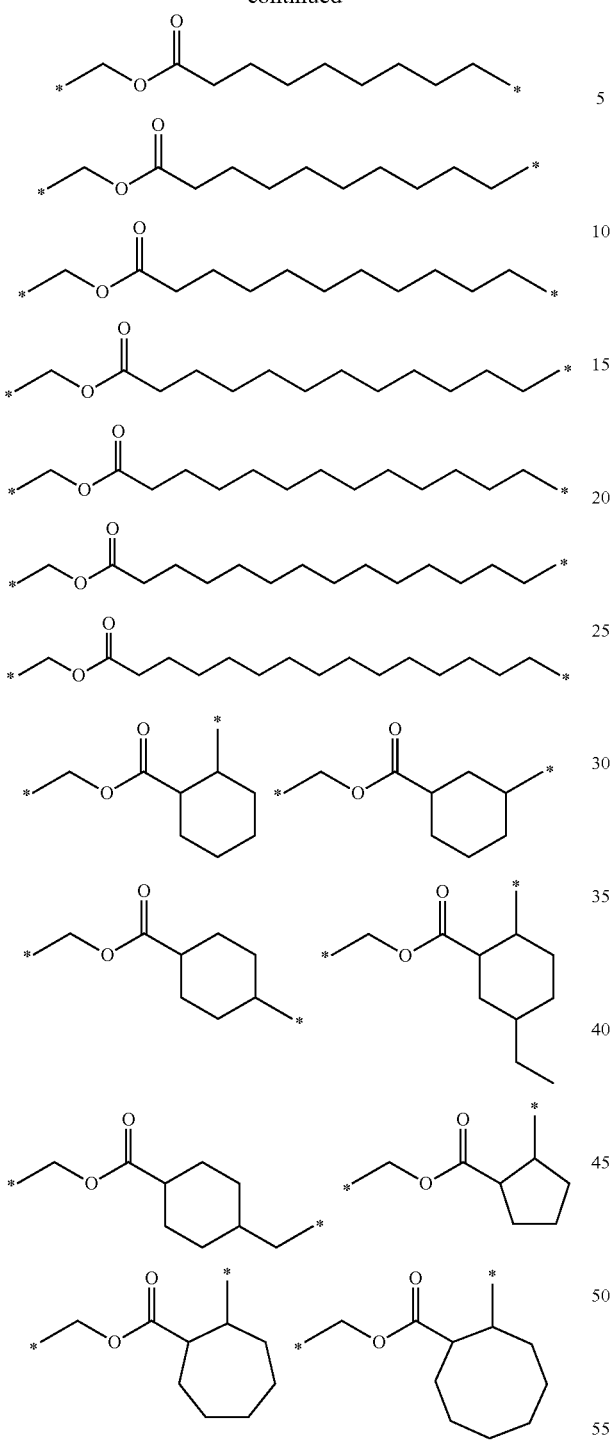

$L^1$ in the formula (I) is preferably *—CO—O-$L^a$-.

The heterocyclic ring of ring $W^1$ has a nitrogen atom which bonds to $L^1$, and may have at least one oxygen atom in addition to a nitrogen atom as the atom constituting the heterocyclic ring. The heterocyclic ring may be any of an aromatic or non-aromatic heterocyclic ring, and any of a monocycle or a polycycle.

Examples of the heterocyclic ring represented by the formula below:

include as the followings.

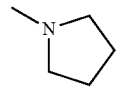
(W1)

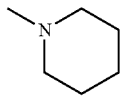
(W2)

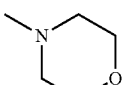
(W3)

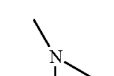
(W4)

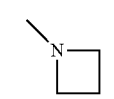
(W5)

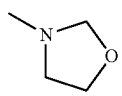
(W6)

(W7)

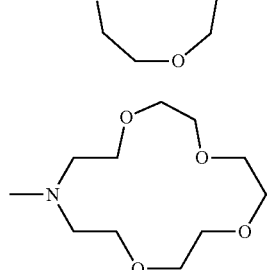
(W8)

Among these, the groups represented by the formula (W1), the formula (W2) and the formula (W3) are preferable.

Examples of the anion (I) of the salt (I) include anions indicated below.

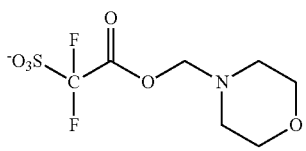
(I-a-1)

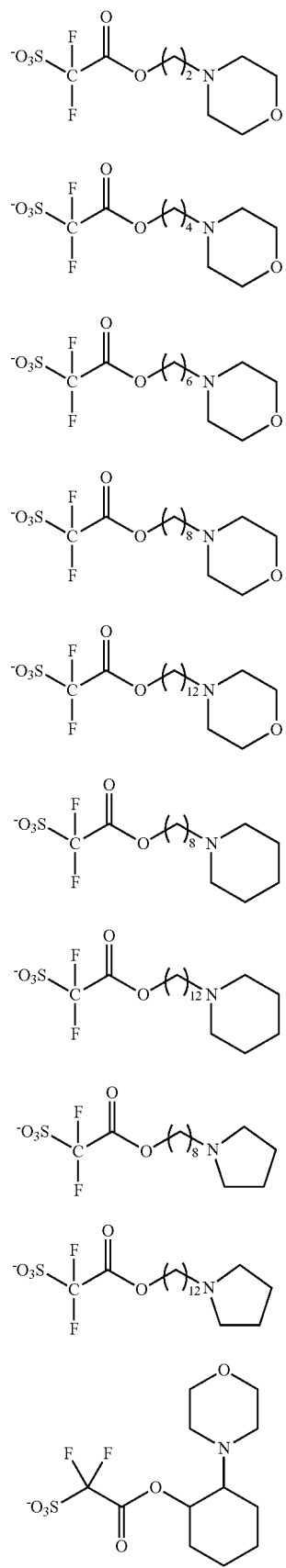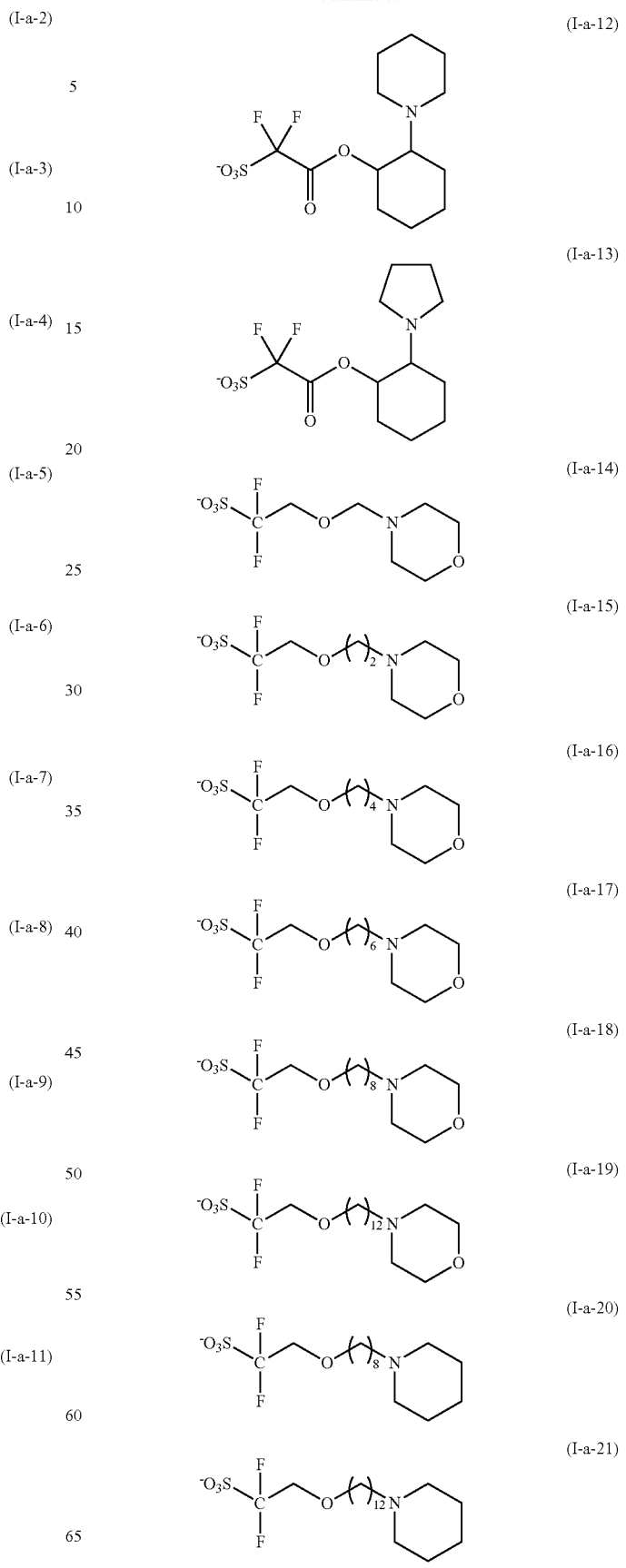

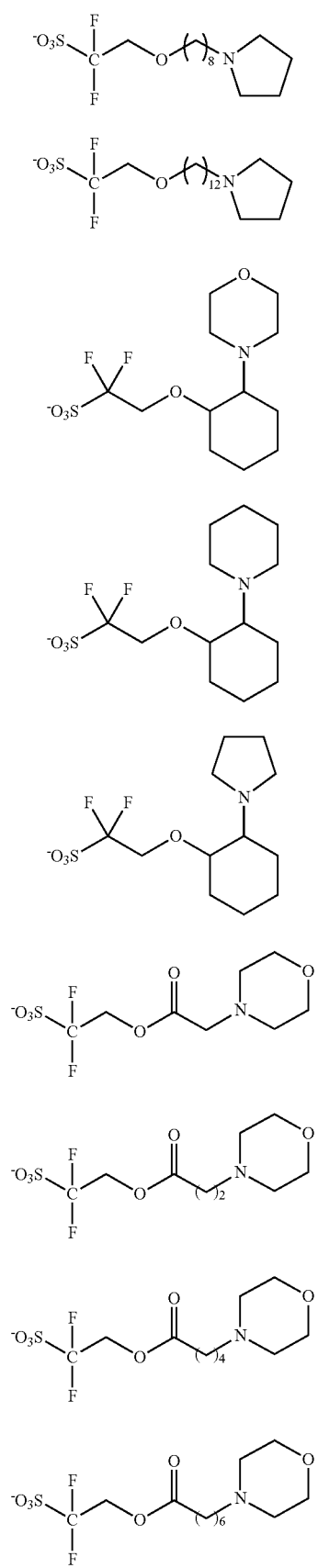
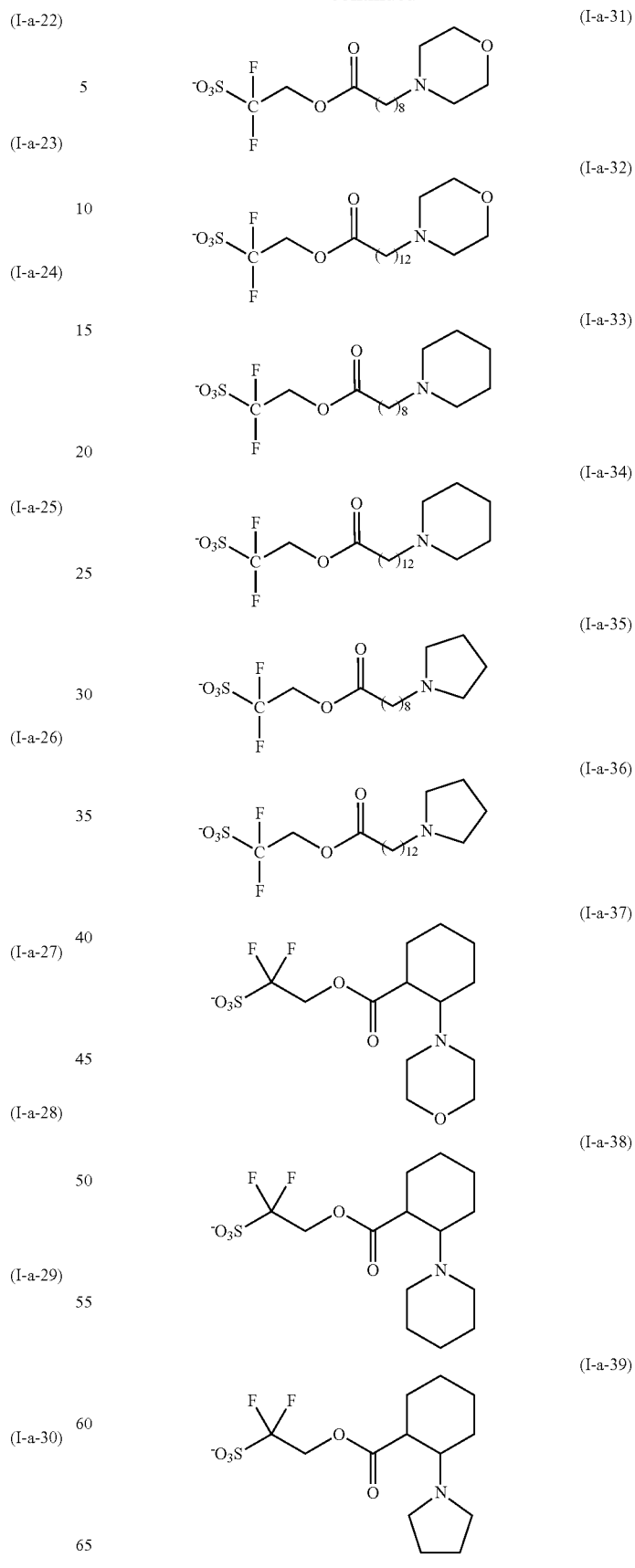

The hydrocarbon group of $R^{e1}$ to $R^{e13}$ includes any of a $C_1$ to $C_{12}$ alkyl group, a $C_1$ to $C_{12}$ alkenyl group, a $C_1$ to $C_{12}$ alkynyl group and a $C_6$ to $C_{12}$ aryl.

A group in which a hydrocarbon group is an alkyl group and one or more —CH$_2$— contained in the alkyl group may be replaced by —O— or —CO— include any of, for example, a $C_1$ to $C_{11}$ alkoxy alkyl group, a $C_2$ to $C_{12}$ acyl group, a $C_2$ to $C_u$ acyloxy group, a $C_2$ to $C_{10}$ alkoxycarbonyloxy group and a $C_2$ to $C_{11}$ alkoxycarbonyl group.

A ring formed by two of $R^{e1}$ to $R^{e13}$ bonded to adjacent carbon atoms together with two carbon atoms bonded thereto include any of an aromatic or non-aromatic, alicyclic or heterocyclic ring, and monocycle or polycycle (i.e., condensed ring). Example of the ring include a benzene ring, a naphthalene ring, an anthracene ring, a phenanthrene ring, a fluorene ring, a triphenylene ring, a naphthacene ring, a biphenyl ring, a pyrrole ring, a franc ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxaline ring, an isoquinoline ring, a carbazole ring, a phenanthridine ring, an acridine ring, a phenanthroline ring, a thianthrene ring, a chromene ring, a xanthene ring, a phenoxathiin ring, a phenothiazine ring and phenazine ring.

Among these, $R^{e1}$ to $R^{e13}$ are preferably independently a hydrogen atom, a halogen atom, a hydroxy group, an alkyl group or an alkoxy group, and more preferably independently a hydrogen atom in view of ease of manufacture.

Examples of the divalent linking group of Z include a $C_1$ to $C_4$ alkandiyl group, a $C_6$ to $C_{10}$ arylene group, a carbonyl group (—CO—), a sulfonyl group (—SO$_2$—), a carbonyloxy group (—COO—), a carbonyl imino group (—CONH—), a sulfonyl imino group (—SO$_2$NH—), an imino group (—NH—), a dithio group (—SS—), vinylene group (—CH=CH—), an imino carbonyl imino group (—NH-CONH—), an imino sulfonyl imino group (—NHSO$_2$NH—), an oxygen atom (—O—) and sulfur atom (—S—).

Among these, Z is preferably a single bond, an alkandiyl group, an arylene group, a sulfonyl group, an imino group, a vinylene group, an imino carbonyl imino group, an imino sulfonyl imino group, an oxygen atom and sulfur atom, more prefably a single bond, an alkandiyl group, and an oxygen atom, and still more preferably an oxygen atom.

The cation (I) of the salt (I) preferably include cations below,

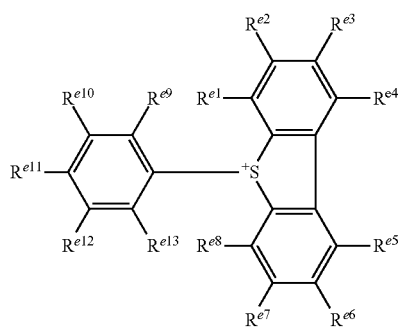

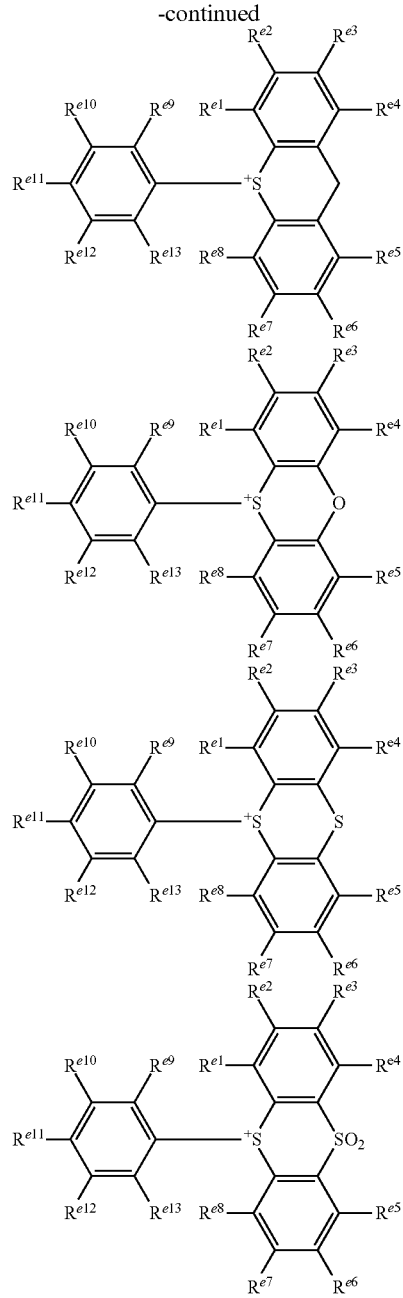

wherein $R^{e1}$ to Ren represent the same meaning as defined above.

Specific examples of the cation (I) of the salt (I) include cations below.

(I-c-1)

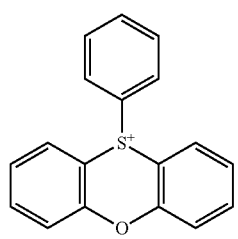

(I-c-2)
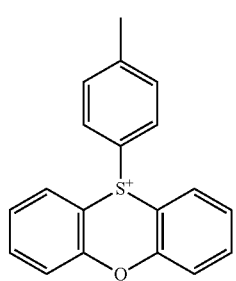
(I-c-3)
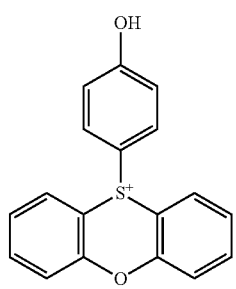
(I-c-4)
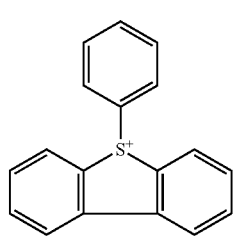
(I-c-5)
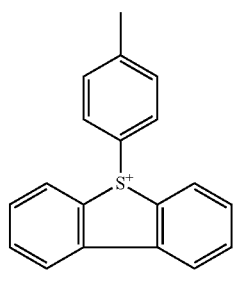
(I-c-6)
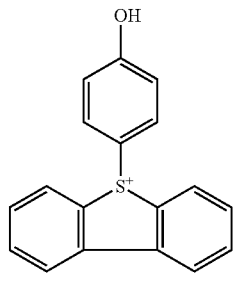
(I-c-7)
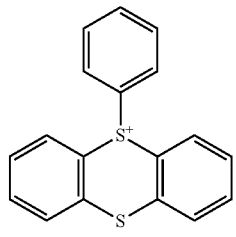
(I-c-8)
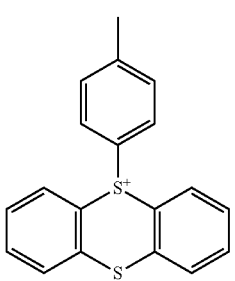
(I-c-9)
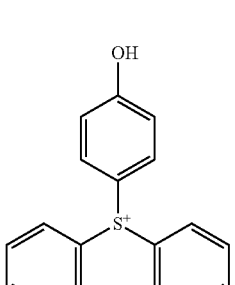
(I-c-10)
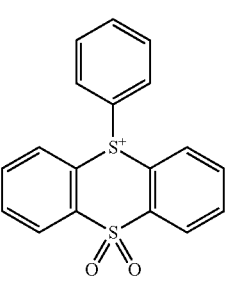
(I-c-11)
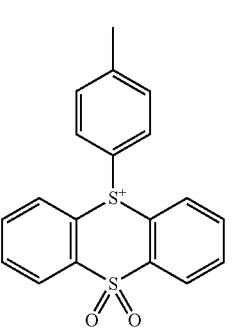
(I-c-12)
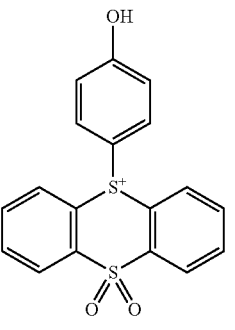

-continued (I-c-13)

(I-c-14)

(I-c-15)

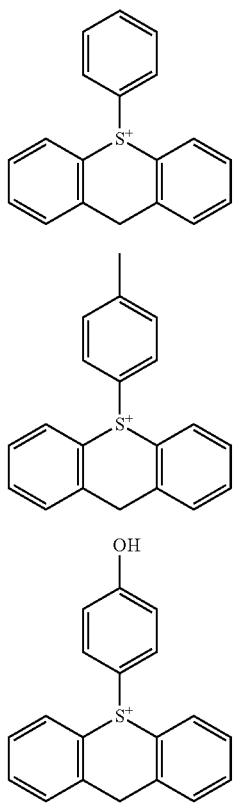

The salt (I) is a salt in combination of the above anion (I) and cation (I). The above anion and the cation may optionally be combined, for example, as described in the Tables below. The anion represented by the formula (1-a-1) is expressed "(1-a-1)", and the cation represented by the formula (1-c-1) is expressed "(1-c-1)" in the table, for example.

TABLE 1

| Salt (I) | Anion (I) | Cation (I) |
|---|---|---|
| (I-1) | (I-a-5) | (I-c-1) |
| (I-2) | (I-a-6) | (I-c-1) |
| (I-3) | (I-a-1) | (I-c-1) |
| (I-4) | (I-a-2) | (I-c-1) |
| (I-5) | (I-a-3) | (I-c-1) |
| (I-6) | (I-a-4) | (I-c-1) |
| (I-7) | (I-a-7) | (I-c-1) |
| (I-8) | (I-a-8) | (I-c-1) |
| (I-9) | (I-a-9) | (I-c-1) |
| (I-10) | (I-a-10) | (I-c-1) |
| (I-11) | (I-a-11) | (I-c-1) |
| (I-12) | (I-a-12) | (I-c-1) |
| (I-13) | (I-a-13) | (I-c-1) |
| (I-14) | (I-a-14) | (I-c-1) |
| (I-15) | (I-a-15) | (I-c-1) |
| (I-16) | (I-a-16) | (I-c-1) |
| (I-17) | (I-a-17) | (I-c-1) |
| (I-18) | (I-a-18) | (I-c-1) |
| (I-19) | (I-a-19) | (I-c-1) |
| (I-20) | (I-a-20) | (I-c-1) |
| (I-21) | (I-a-21) | (I-c-1) |
| (I-22) | (I-a-22) | (I-c-1) |
| (I-23) | (I-a-23) | (I-c-1) |
| (I-24) | (I-a-24) | (I-c-1) |
| (I-25) | (I-a-25) | (I-c-1) |
| (I-26) | (I-a-26) | (I-c-1) |
| (I-27) | (I-a-27) | (I-c-1) |

TABLE 1-continued

| Salt (I) | Anion (I) | Cation (I) |
|---|---|---|
| (I-28) | (I-a-28) | (I-c-1) |
| (I-29) | (I-a-29) | (I-c-1) |
| (I-30) | (I-a-30) | (I-c-1) |
| (I-31) | (I-a-31) | (I-c-1) |
| (I-32) | (I-a-32) | (I-c-1) |
| (I-33) | (I-a-33) | (I-c-1) |
| (I-34) | (I-a-34) | (I-c-1) |
| (I-35) | (I-a-35) | (I-c-1) |
| (I-36) | (I-a-36) | (I-c-1) |
| (I-37) | (I-a-37) | (I-c-1) |
| (I-38) | (I-a-38) | (I-c-1) |
| (I-39) | (I-a-39) | (I-c-1) |

TABLE 2

| Salt (I) | Anion (I) | Cation (I) |
|---|---|---|
| (I-40) | (I-a-5) | (I-c-2) |
| (I-41) | (I-a-6) | (I-c-2) |
| (I-42) | (I-a-1) | (I-c-2) |
| (I-43) | (I-a-2) | (I-c-2) |
| (I-44) | (I-a-3) | (I-c-2) |
| (I-45) | (I-a-4) | (I-c-2) |
| (I-46) | (I-a-7) | (I-c-2) |
| (I-47) | (I-a-8) | (I-c-2) |
| (I-48) | (I-a-9) | (I-c-2) |
| (I-49) | (I-a-10) | (I-c-2) |
| (I-50) | (I-a-11) | (I-c-2) |
| (I-51) | (I-a-12) | (I-c-2) |
| (I-52) | (I-a-13) | (I-c-2) |
| (I-53) | (I-a-14) | (I-c-2) |
| (I-54) | (I-a-15) | (I-c-2) |
| (I-55) | (I-a-16) | (I-c-2) |
| (I-56) | (I-a-17) | (I-c-2) |
| (I-57) | (I-a-18) | (I-c-2) |
| (I-58) | (I-a-19) | (I-c-2) |
| (I-59) | (I-a-20) | (I-c-2) |
| (I-60) | (I-a-21) | (I-c-2) |
| (I-61) | (I-a-22) | (I-c-2) |
| (I-62) | (I-a-23) | (I-c-2) |
| (I-63) | (I-a-24) | (I-c-2) |
| (I-64) | (I-a-25) | (I-c-2) |
| (I-65) | (I-a-26) | (I-c-2) |
| (I-66) | (I-a-27) | (I-c-2) |
| (I-67) | (I-a-28) | (I-c-2) |
| (I-68) | (I-a-29) | (I-c-2) |
| (I-69) | (I-a-30) | (I-c-2) |
| (I-70) | (I-a-31) | (I-c-2) |
| (I-71) | (I-a-32) | (I-c-2) |
| (I-72) | (I-a-33) | (I-c-2) |
| (I-73) | (I-a-34) | (I-c-2) |
| (I-74) | (I-a-35) | (I-c-2) |
| (I-75) | (I-a-36) | (I-c-2) |
| (I-76) | (I-a-37) | (I-c-2) |
| (I-77) | (I-a-38) | (I-c-2) |
| (I-78) | (I-a-39) | (I-c-2) |

TABLE 3

| Salt (I) | Anion (I) | Cation (I) |
|---|---|---|
| (I-79) | (I-a-5) | (I-c-3) |
| (I-80) | (I-a-6) | (I-c-3) |
| (I-81) | (I-a-1) | (I-c-3) |
| (I-82) | (I-a-2) | (I-c-3) |
| (I-83) | (I-a-3) | (I-c-3) |
| (I-84) | (I-a-4) | (I-c-3) |
| (I-85) | (I-a-7) | (I-c-3) |
| (I-86) | (I-a-8) | (I-c-3) |
| (I-87) | (I-a-9) | (I-c-3) |
| (I-88) | (I-a-10) | (I-c-3) |
| (I-89) | (I-a-11) | (I-c-3) |
| (I-90) | (I-a-12) | (I-c-3) |

TABLE 3-continued

| Salt (I) | Anion (I) | Cation (I) |
| --- | --- | --- |
| (I-91) | (I-a-13) | (I-c-3) |
| (I-92) | (I-a-14) | (I-c-3) |
| (I-93) | (I-a-15) | (I-c-3) |
| (I-94) | (I-a-16) | (I-c-3) |
| (I-95) | (I-a-17) | (I-c-3) |
| (I-96) | (I-a-18) | (I-c-3) |
| (I-97) | (I-a-19) | (I-c-3) |
| (I-98) | (I-a-20) | (I-c-3) |
| (I-99) | (I-a-21) | (I-c-3) |
| (I-100) | (I-a-22) | (I-c-3) |
| (I-101) | (I-a-23) | (I-c-3) |
| (I-102) | (I-a-24) | (I-c-3) |
| (I-103) | (I-a-25) | (I-c-3) |
| (I-104) | (I-a-26) | (I-c-3) |
| (I-105) | (I-a-27) | (I-c-3) |
| (I-106) | (I-a-28) | (I-c-3) |
| (I-107) | (I-a-29) | (I-c-3) |
| (I-108) | (I-a-30) | (I-c-3) |
| (I-109) | (I-a-31) | (I-c-3) |
| (I-110) | (I-a-32) | (I-c-3) |
| (I-111) | (I-a-33) | (I-c-3) |
| (I-112) | (I-a-34) | (I-c-3) |
| (I-113) | (I-a-35) | (I-c-3) |
| (I-114) | (I-a-36) | (I-c-3) |
| (I-115) | (I-a-37) | (I-c-3) |
| (I-116) | (I-a-38) | (I-c-3) |
| (I-117) | (I-a-39) | (I-c-3) |

TABLE 4

| Salt (I) | Anion (I) | Cation (I) |
| --- | --- | --- |
| (I-118) | (I-a-5) | (I-c-4) |
| (I-119) | (I-a-6) | (I-c-4) |
| (I-120) | (I-a-1) | (I-c-4) |
| (I-121) | (I-a-2) | (I-c-4) |
| (I-122) | (I-a-3) | (I-c-4) |
| (I-123) | (I-a-4) | (I-c-4) |
| (I-124) | (I-a-7) | (I-c-4) |
| (I-125) | (I-a-8) | (I-c-4) |
| (I-126) | (I-a-9) | (I-c-4) |
| (I-127) | (I-a-10) | (I-c-4) |
| (I-128) | (I-a-11) | (I-c-4) |
| (I-129) | (I-a-12) | (I-c-4) |
| (I-130) | (I-a-13) | (I-c-4) |
| (I-131) | (I-a-14) | (I-c-4) |
| (I-132) | (I-a-15) | (I-c-4) |
| (I-133) | (I-a-16) | (I-c-4) |
| (I-134) | (I-a-17) | (I-c-4) |
| (I-135) | (I-a-18) | (I-c-4) |
| (I-136) | (I-a-19) | (I-c-4) |
| (I-137) | (I-a-20) | (I-c-4) |
| (I-138) | (I-a-21) | (I-c-4) |
| (I-139) | (I-a-22) | (I-c-4) |
| (I-140) | (I-a-23) | (I-c-4) |
| (I-141) | (I-a-24) | (I-c-4) |
| (I-142) | (I-a-25) | (I-c-4) |
| (I-143) | (I-a-26) | (I-c-4) |
| (I-144) | (I-a-27) | (I-c-4) |
| (I-145) | (I-a-28) | (I-c-4) |
| (I-146) | (I-a-29) | (I-c-4) |
| (I-147) | (I-a-30) | (I-c-4) |
| (I-148) | (I-a-31) | (I-c-4) |
| (I-149) | (I-a-32) | (I-c-4) |
| (I-150) | (I-a-33) | (I-c-4) |
| (I-151) | (I-a-34) | (I-c-4) |
| (I-152) | (I-a-35) | (I-c-4) |
| (I-153) | (I-a-36) | (I-c-4) |
| (I-154) | (I-a-37) | (I-c-4) |
| (I-155) | (I-a-38) | (I-c-4) |
| (I-156) | (I-a-39) | (I-c-4) |

TABLE 5

| Salt (I) | Anion (I) | Cation (I) |
| --- | --- | --- |
| (I-157) | (I-a-5) | (I-c-6) |
| (I-158) | (I-a-6) | (I-c-6) |
| (I-159) | (I-a-11) | (I-c-6) |
| (I-160) | (I-a-18) | (I-c-6) |
| (I-161) | (I-a-19) | (I-c-6) |
| (I-162) | (I-a-24) | (I-c-6) |
| (I-163) | (I-a-31) | (I-c-6) |
| (I-164) | (I-a-32) | (I-c-6) |
| (I-165) | (I-a-37) | (I-c-6) |
| (I-166) | (I-a-5) | (I-c-7) |
| (I-167) | (I-a-6) | (I-c-7) |
| (I-168) | (I-a-11) | (I-c-7) |
| (I-169) | (I-a-18) | (I-c-7) |
| (I-170) | (I-a-19) | (I-c-7) |
| (I-171) | (I-a-24) | (I-c-7) |
| (I-172) | (I-a-31) | (I-c-7) |
| (I-173) | (I-a-32) | (I-c-7) |
| (I-174) | (I-a-37) | (I-c-7) |
| (I-175) | (I-a-5) | (I-c-10) |
| (I-176) | (I-a-6) | (I-c-10) |
| (I-177) | (I-a-11) | (I-c-10) |
| (I-178) | (I-a-18) | (I-c-10) |
| (I-179) | (I-a-19) | (I-c-10) |
| (I-180) | (I-a-24) | (I-c-10) |
| (I-181) | (I-a-31) | (I-c-10) |
| (I-182) | (I-a-32) | (I-c-10) |
| (I-183) | (I-a-37) | (I-c-10) |
| (I-184) | (I-a-5) | (I-c-13) |
| (I-185) | (I-a-6) | (I-c-13) |
| (I-186) | (I-a-11) | (I-c-13) |
| (I-187) | (I-a-18) | (I-c-13) |
| (I-188) | (I-a-19) | (I-c-13) |
| (I-189) | (I-a-24) | (I-c-13) |
| (I-190) | (I-a-31) | (I-c-13) |
| (I-191) | (I-a-32) | (I-c-13) |
| (I-192) | (I-a-37) | (I-c-13) |

Specific examples of the salt (I) include salts below.

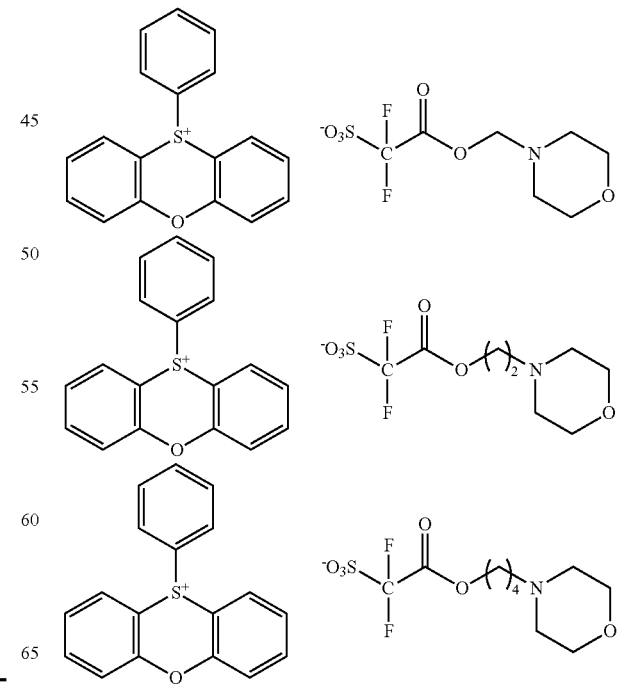

25
-continued
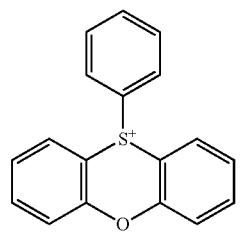 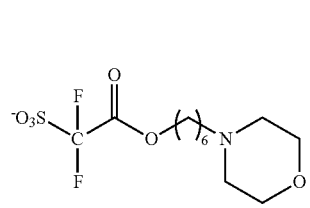
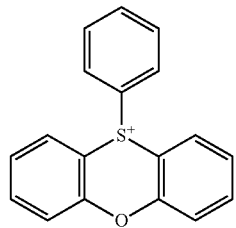 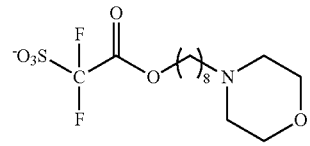
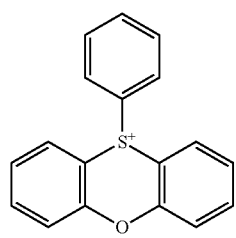 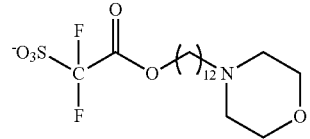
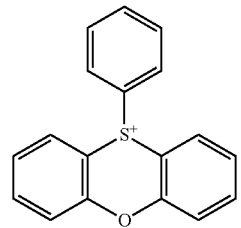 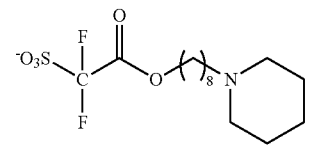
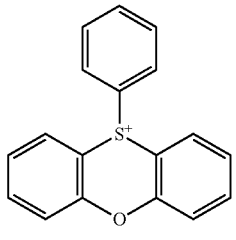 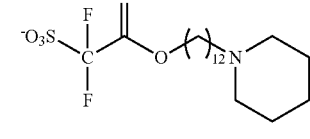
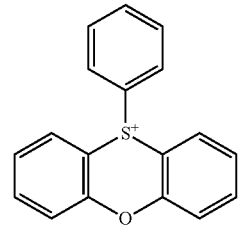 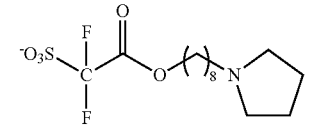
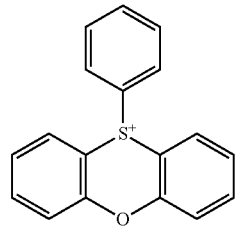 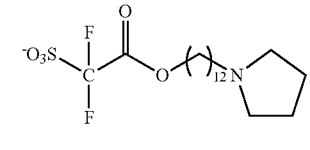
26
-continued
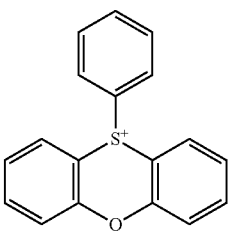 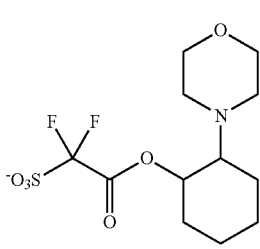
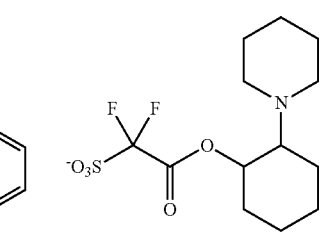 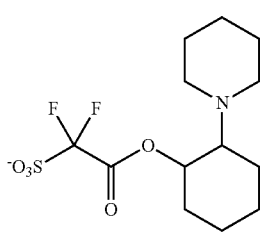
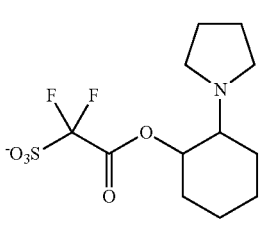
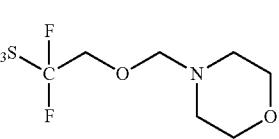
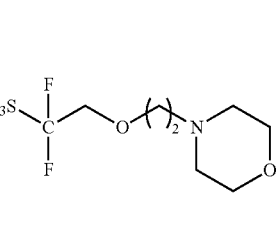
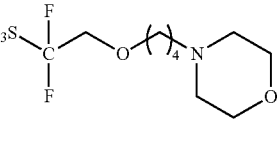
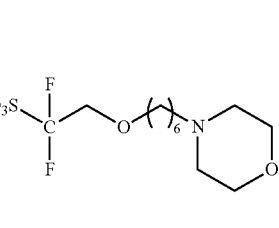

27
-continued
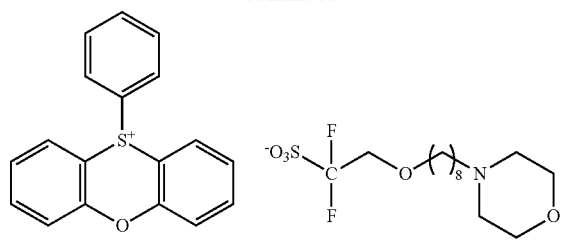
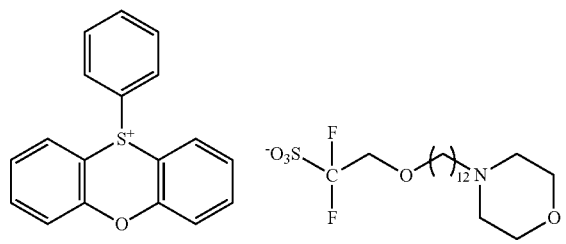
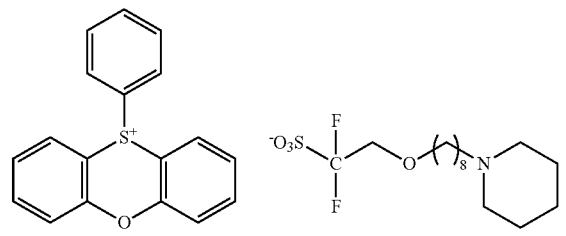
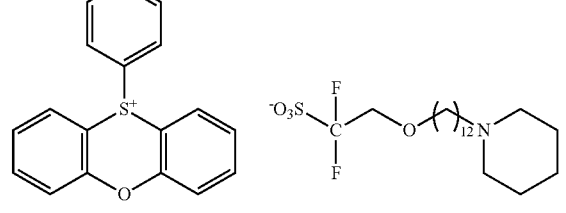
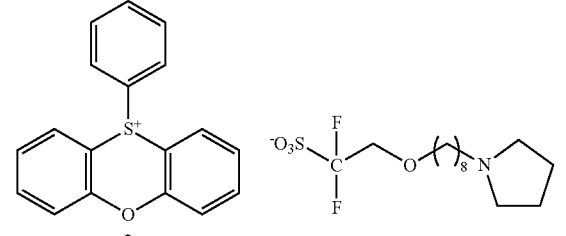
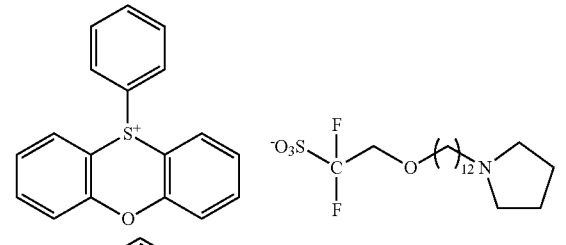
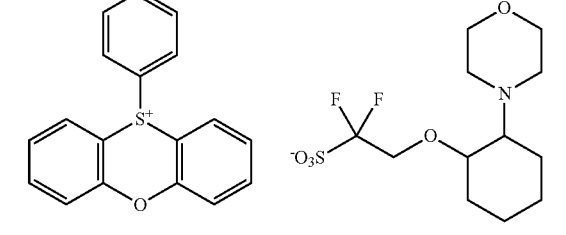
28
-continued
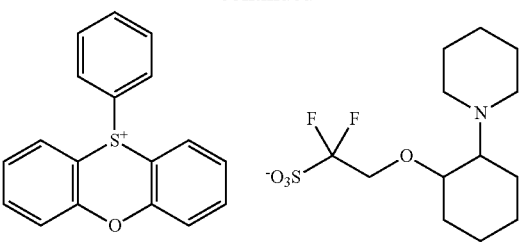
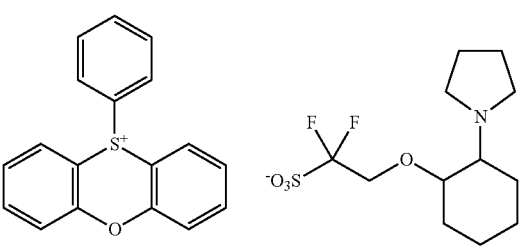
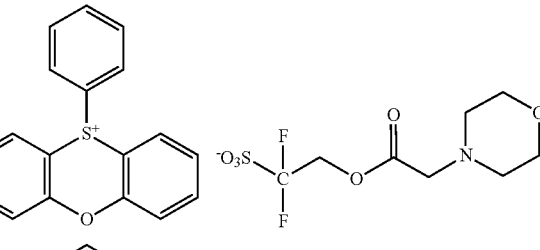
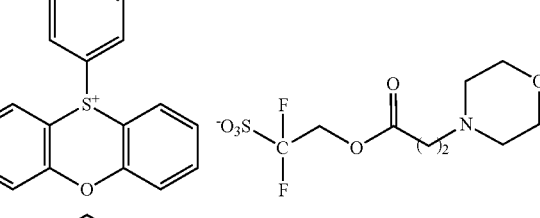
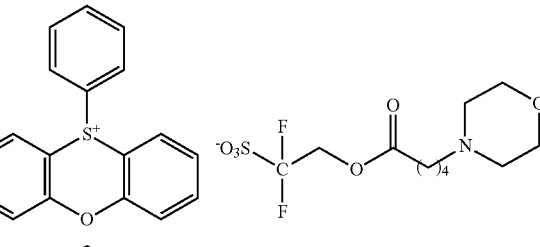
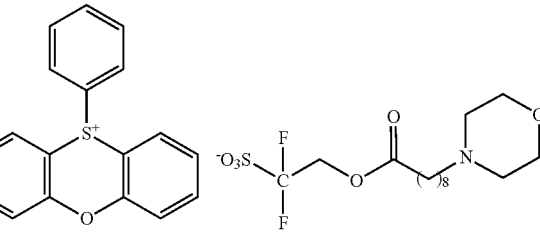

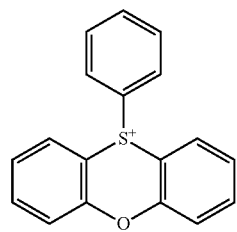 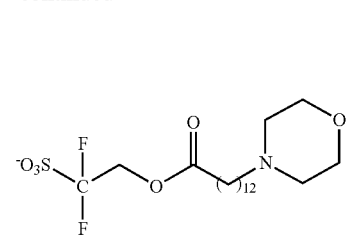 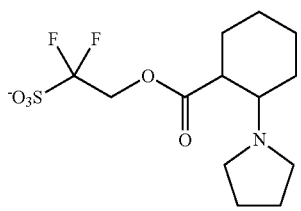
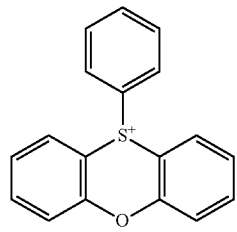 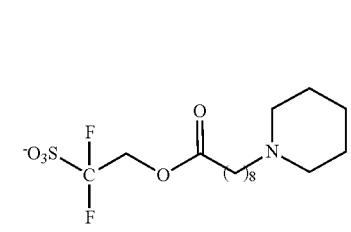 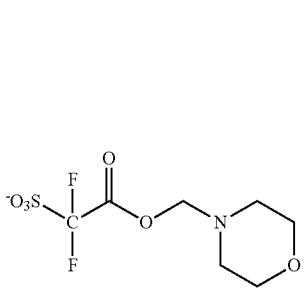
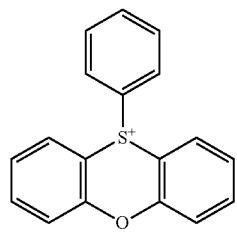 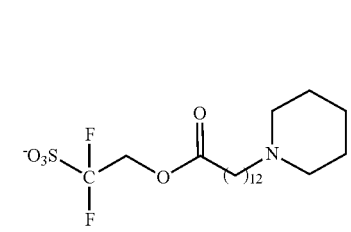 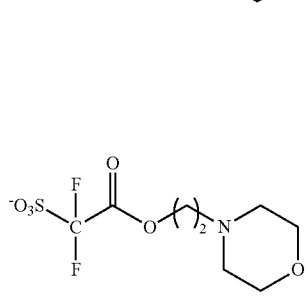
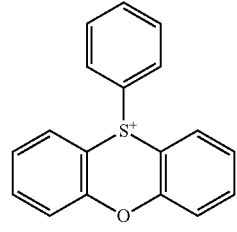 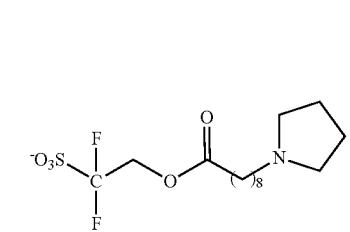 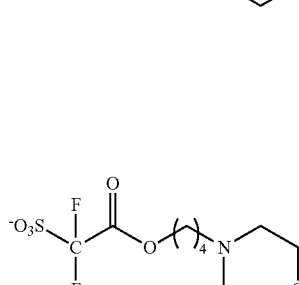
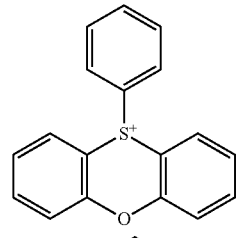 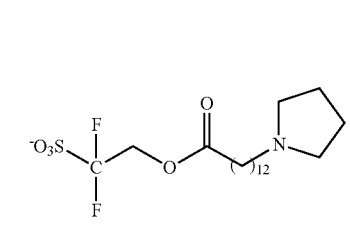 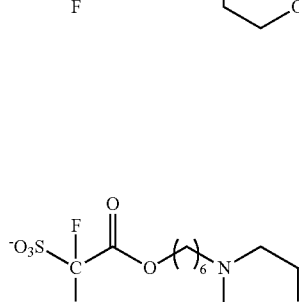
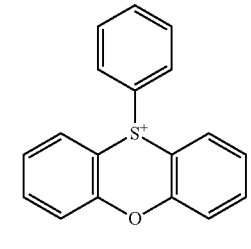 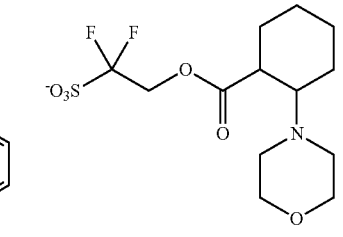 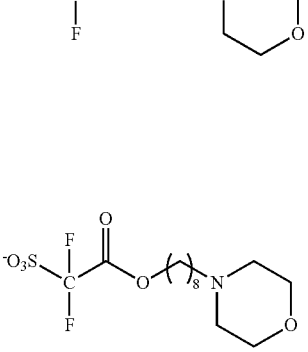
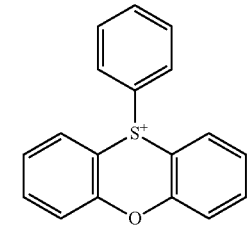 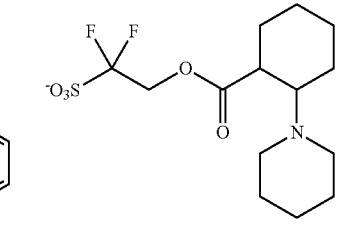

31
-continued
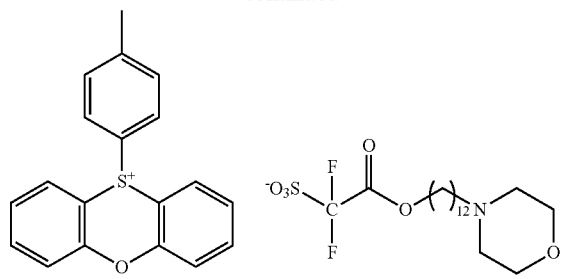
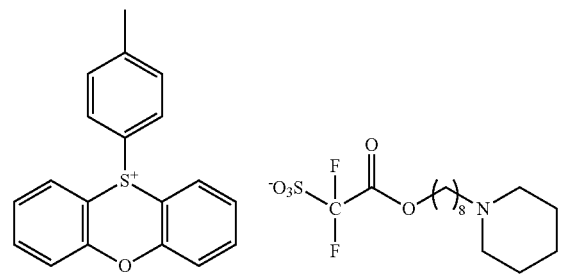
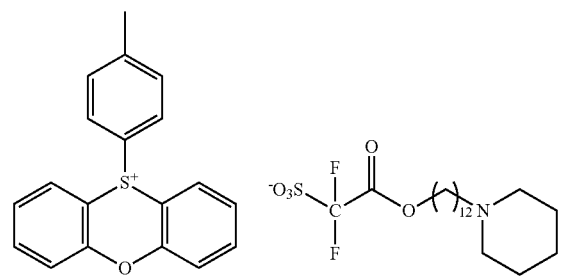
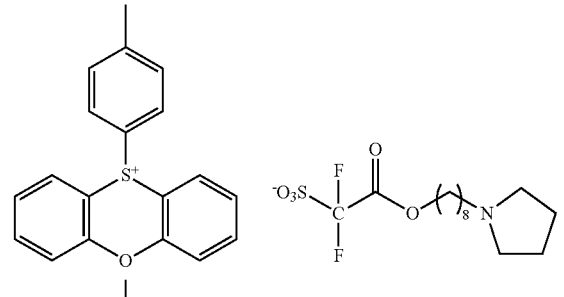
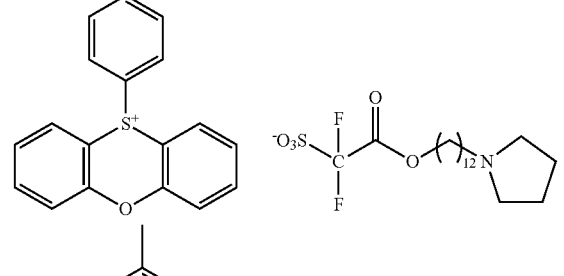
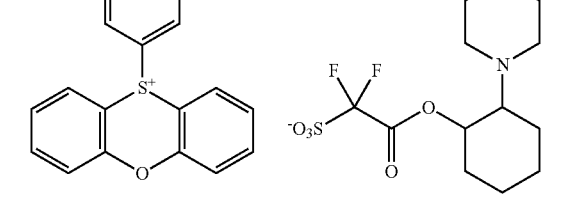
32
-continued
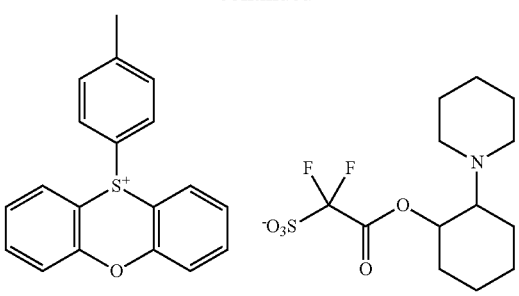
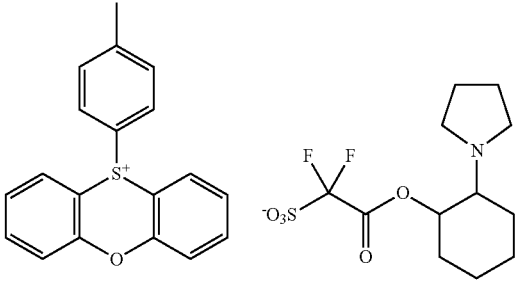
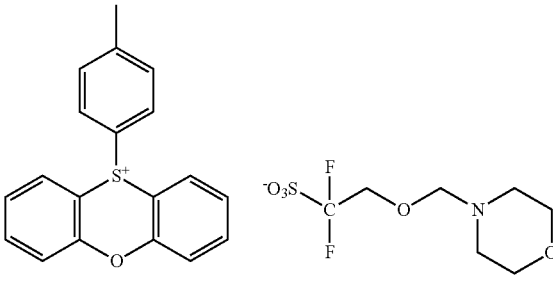
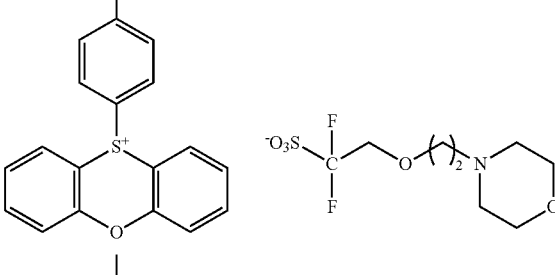
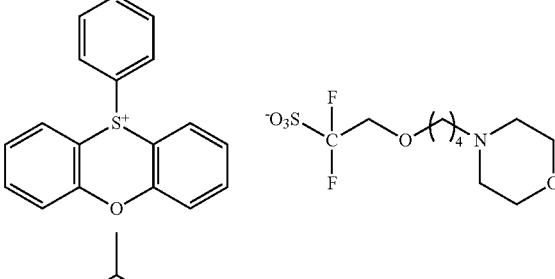
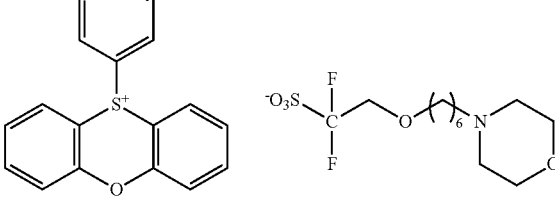

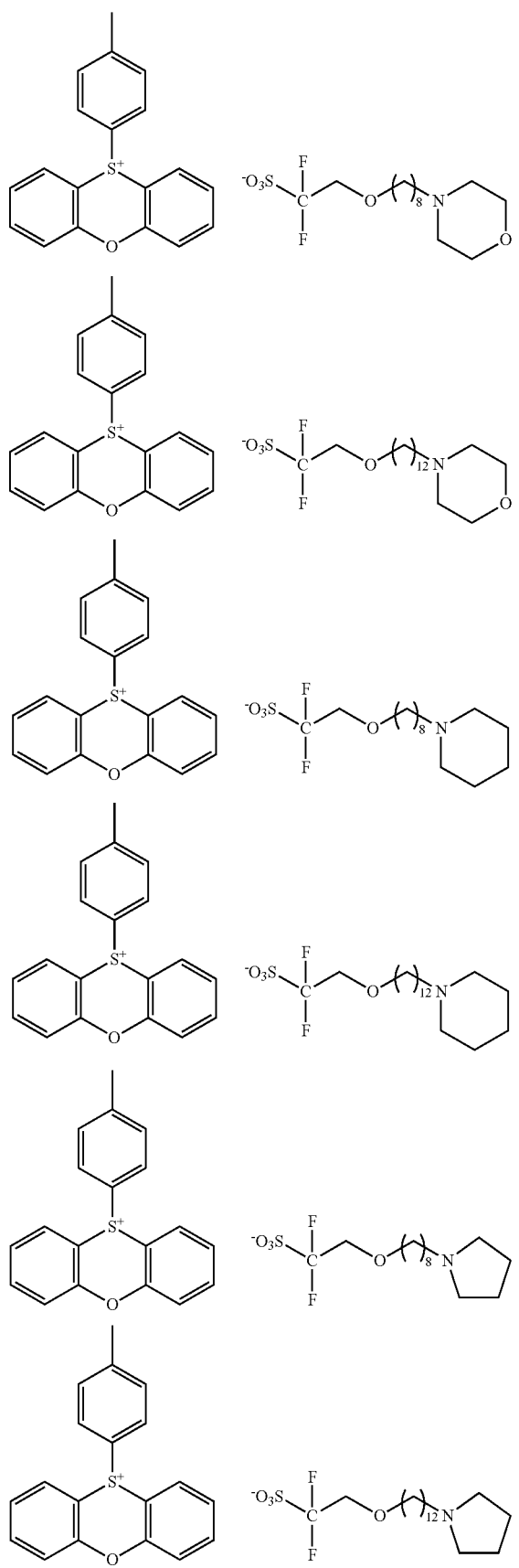
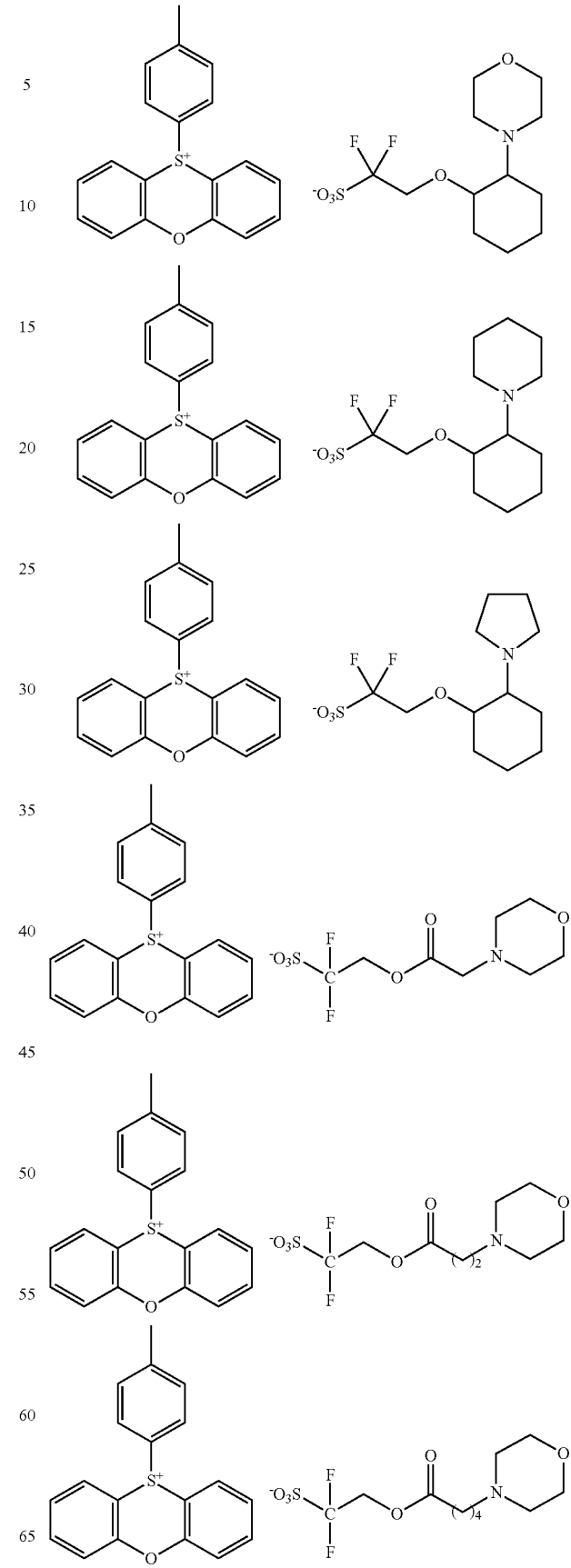

35
-continued
36
-continued
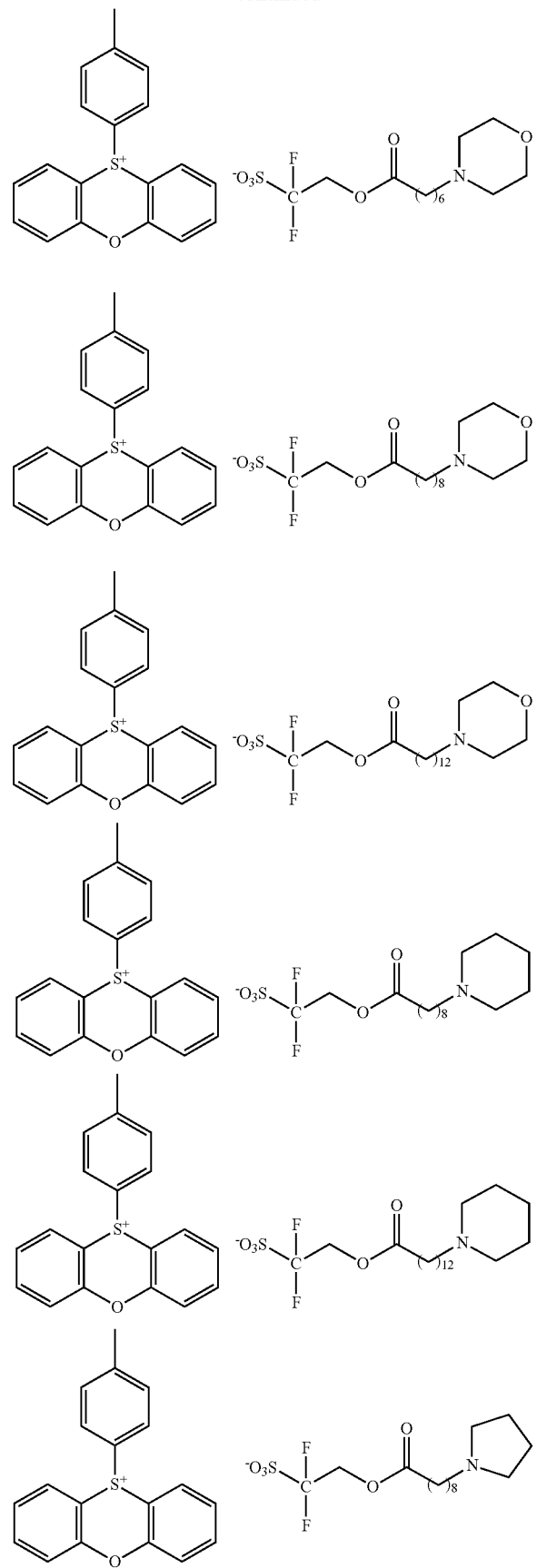
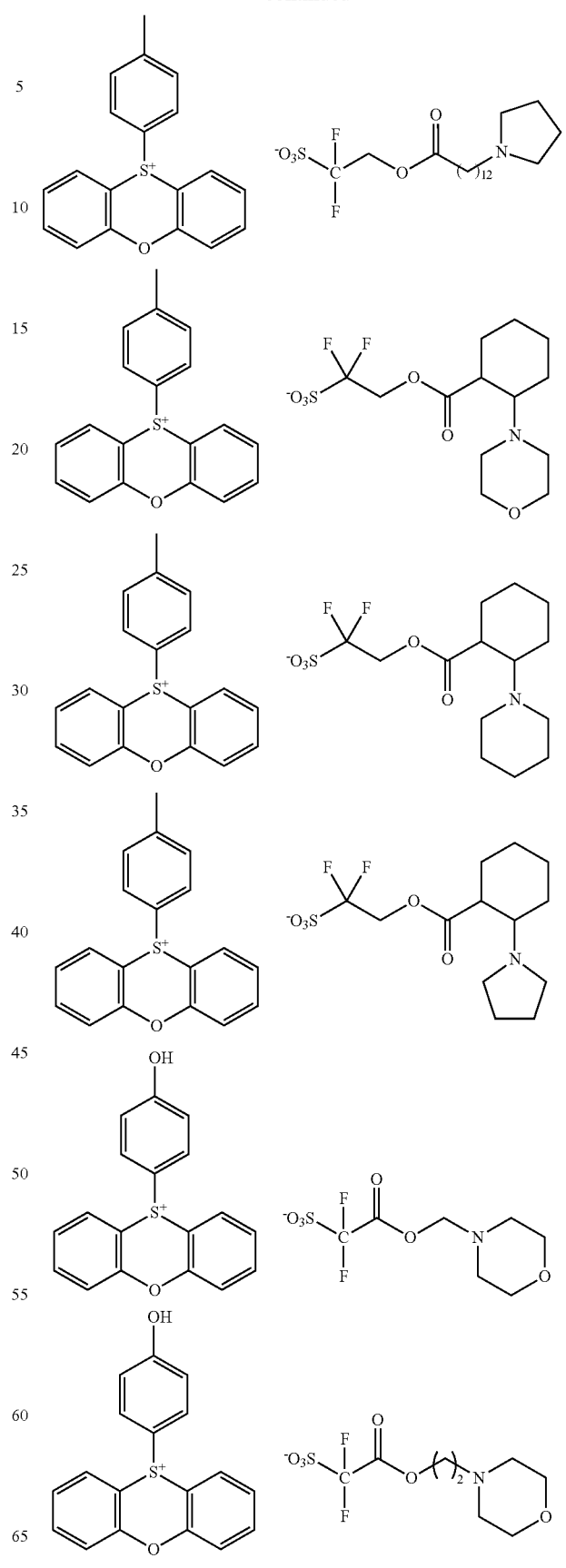

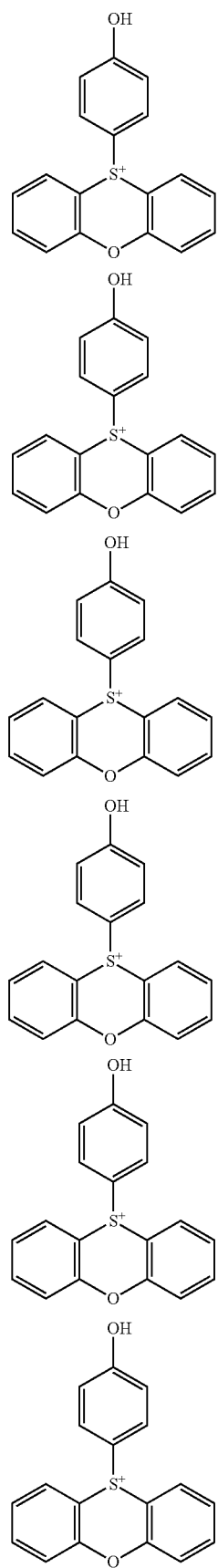
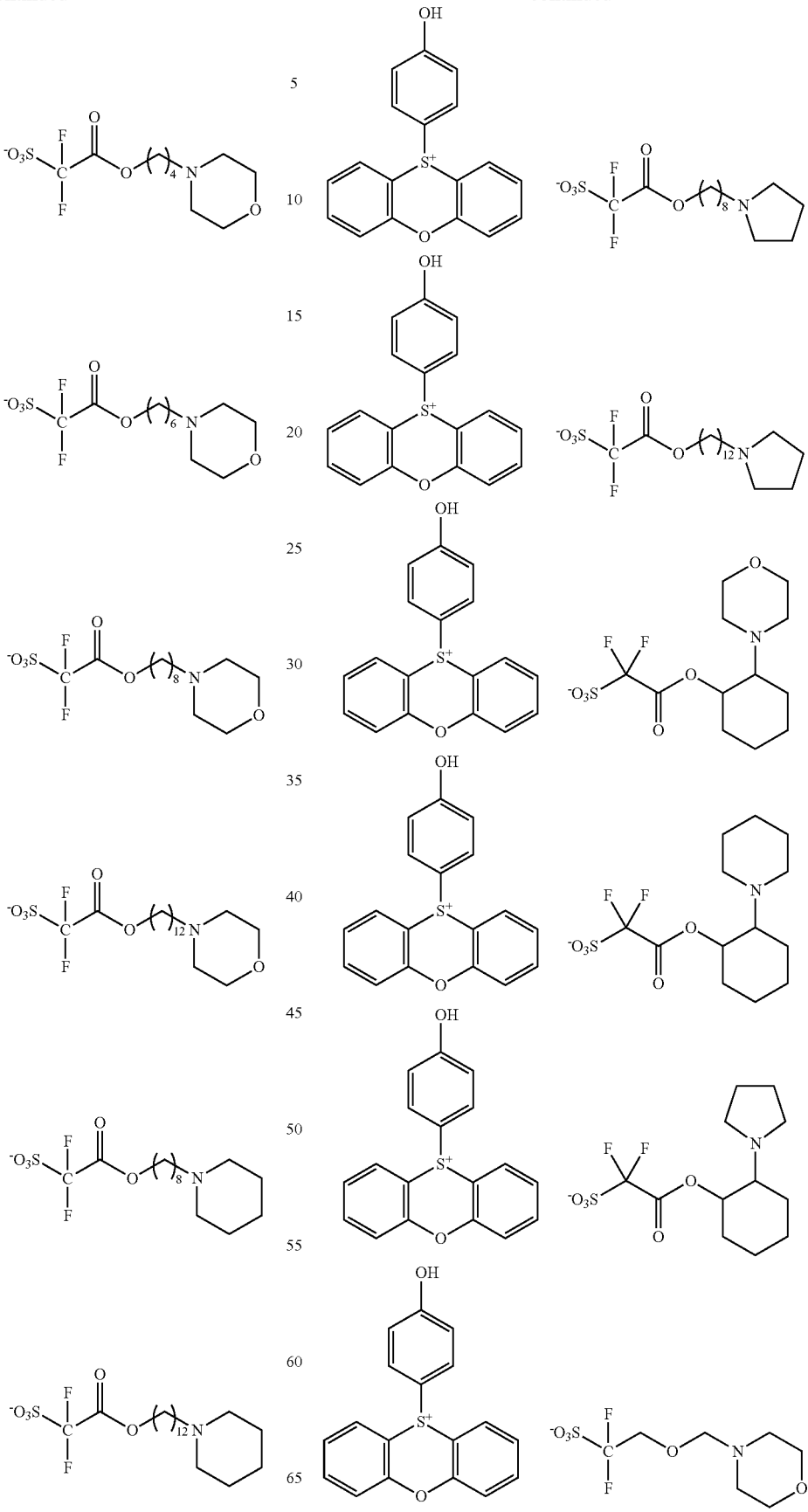

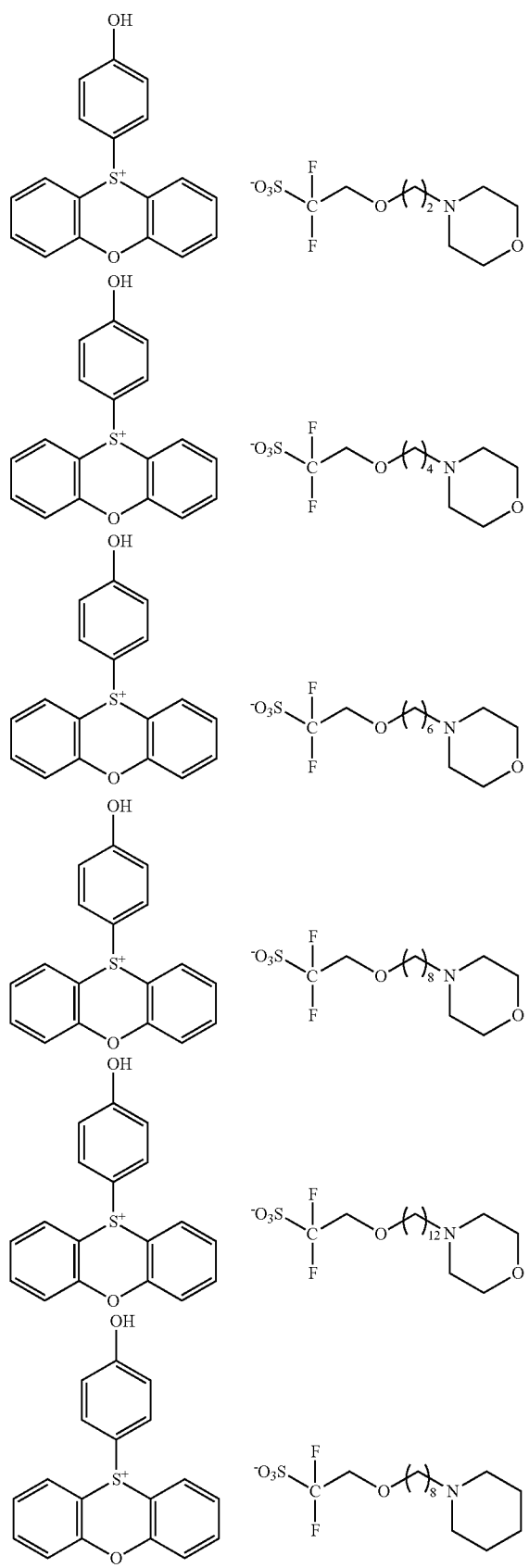
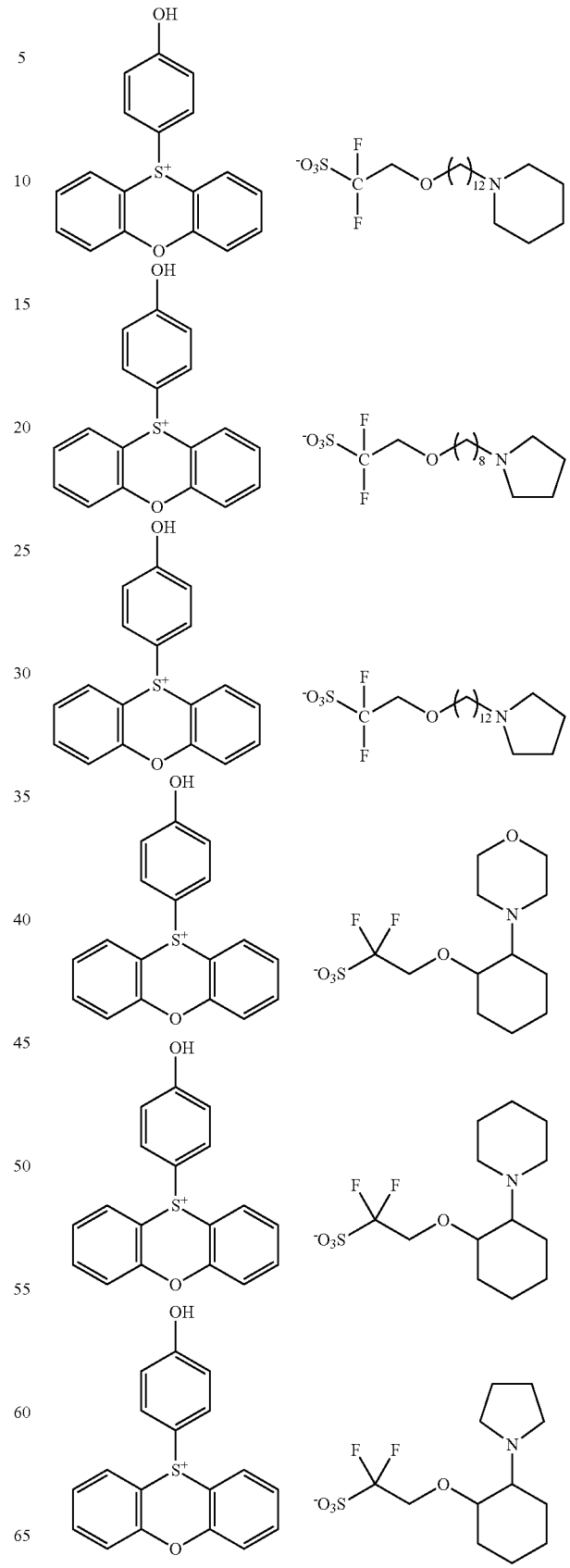

-continued
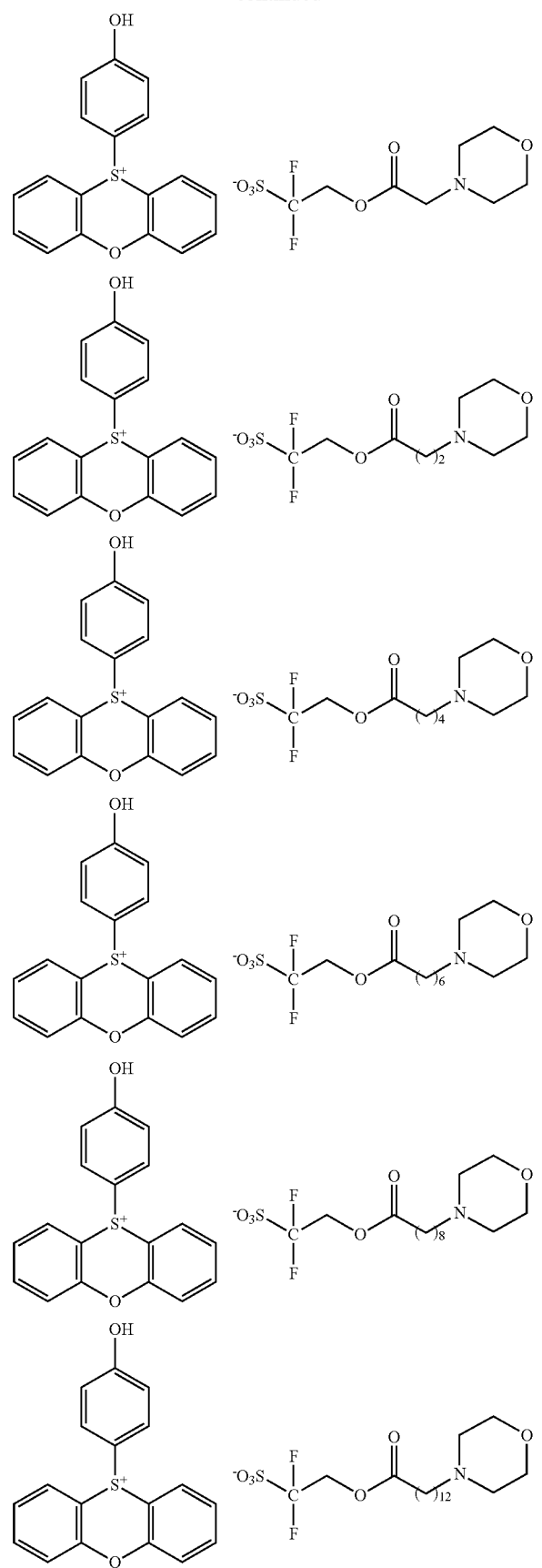
-continued
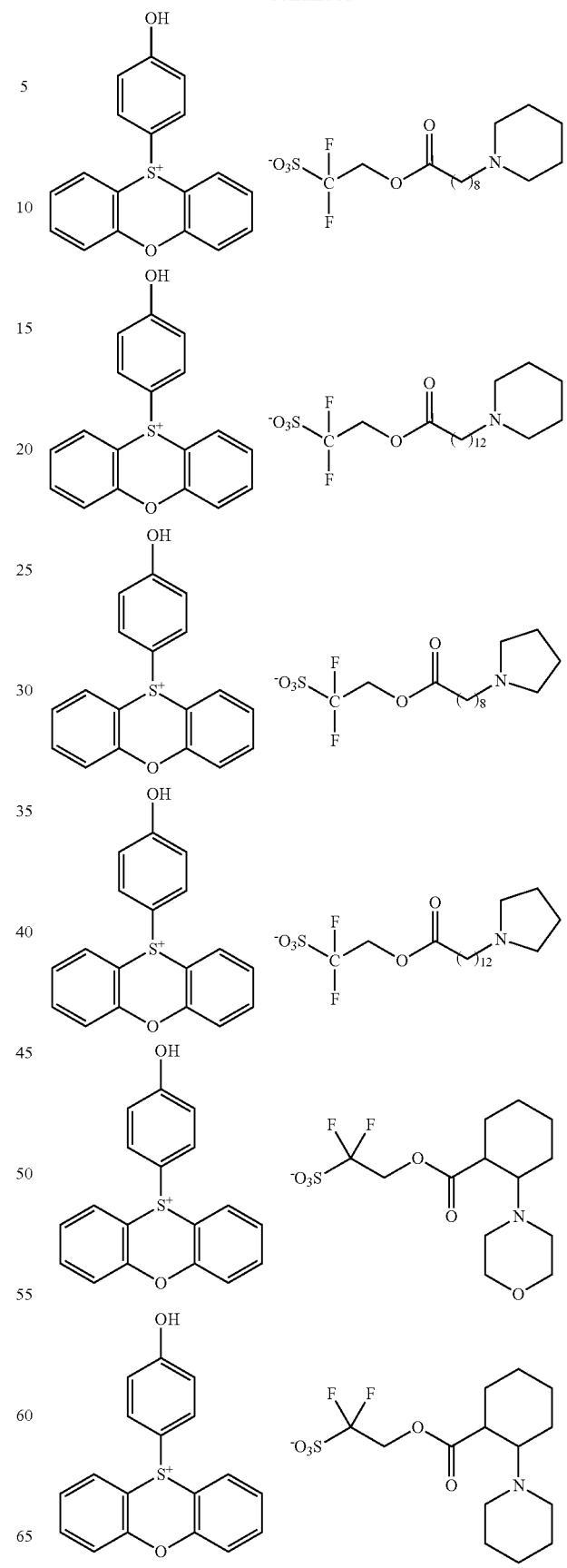

-continued

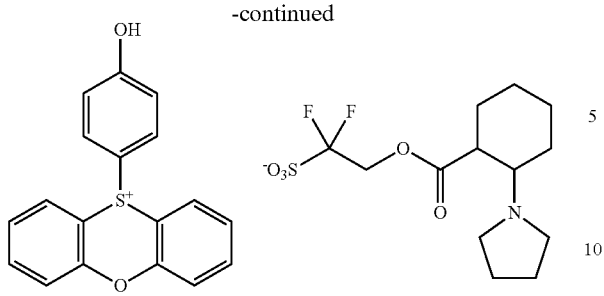

A salt represented by the formula (b1) in which $L^1$ is *—CO—O—$(CH_2)_8$— (hereinafter is sometimes referred to as "salt (b1)") of the salt (I) can be produced, for example, by a method indicated below. In the formula below, $Q^1$, $Q^2$, $W^1$, $R^{e1}$ to $R^{e13}$ and Z represent the same meaning as defined above.

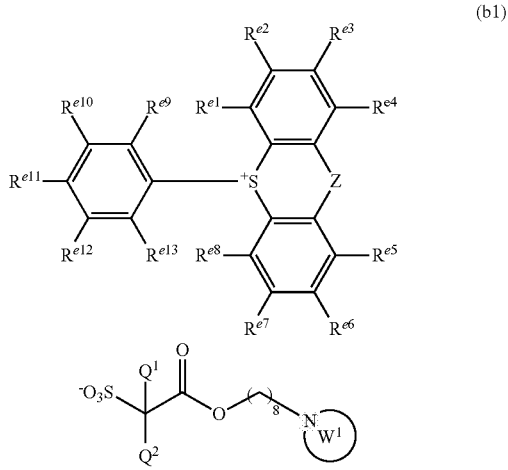

(b1)

A compound which can induce the cation (I) (hereinafter is sometimes referred to as "compound (Ib-c)") can be produced by reacting a compound represented by the formula (b1-a) with a compound represented by the formula (b1-b) in presence of trimethylsilyl chloride in a solvent, and then contacting with hydrochloric acid.

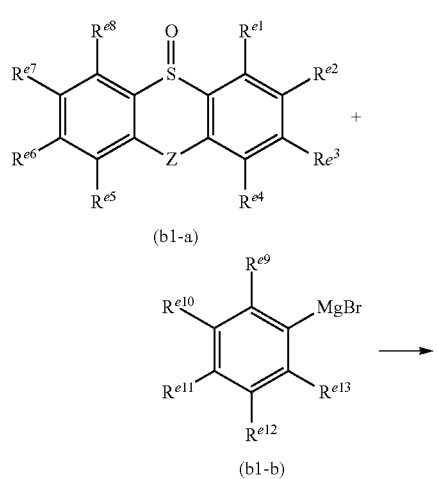

-continued

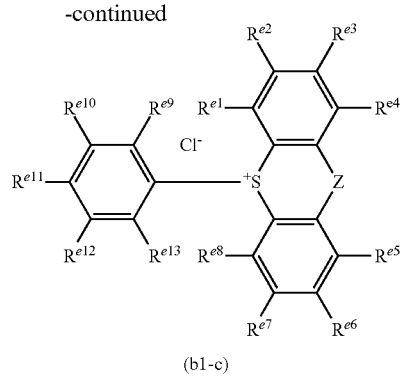

(b1-c)

Preferred examples of the solvent include tetrahydrofuran.

As the compound (b1-a), a marketed product can be used. Examples of the marketed product include dibenzothiophene sulfone. When one or more substituents are introduced into a benzene ring of dibenzothiophene sulfone by a known method, a dibenzothiophene sulfone having any of substituents as $R^{e1}$ to $R^{e8}$ can be obtained. However, non-substituted dibenzothiophene sulfone, in which all of $R^{e1}$ to $R^{e8}$ are a hydrogen atom, is preferable in view of ease of manufacture.

As the compound (b1-b), phenyl magnesium bromide which is a Grignard reagent produced by reacting phenyl bromide and magnesium is preferable in view of easily available. When phenyl bromide is replaced to other aryl halide, a Grignard reagent having any of substituents as $R^{e9}$ to $R^{e13}$ can be obtained. However, non-substituted phenyl magnesium bromide, in which all of $R^{e9}$ to $R^{e13}$ are a hydrogen atom, is preferable in view of ease of manufacture and easily-available.

A compound which can induce the anion (I) (hereinafter is sometimes referred to as "compound (Ib-f)") can be produced by reacting a compound represented by the formula (b1-d) with a compound represented by the formula (b1-e) in presence of an acid catalyst in a solvent.

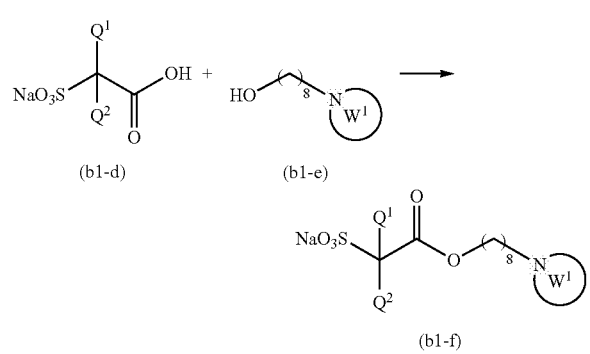

The compound (b1-d) can be produced by a method described in JP2006-257078A.

As the compound (b1-e), a marketed product can be used. Examples of the marketed product include 4-(8-hydroxyoctyl)morpholine and 4-(2-hydroxyethyl)morpholine.

Preferred examples of the solvent include n-heptane. Preferred examples of the acid catalyst include trifluoroacetic acid.

The salt (b1) can be produced by reacting thus obtained compound which can induce the cation (I) (compound (Ib-c)) and the compound which can induce the anion (I) (compound (Ib-f)) in presence of an acid catalyst in a solvent.

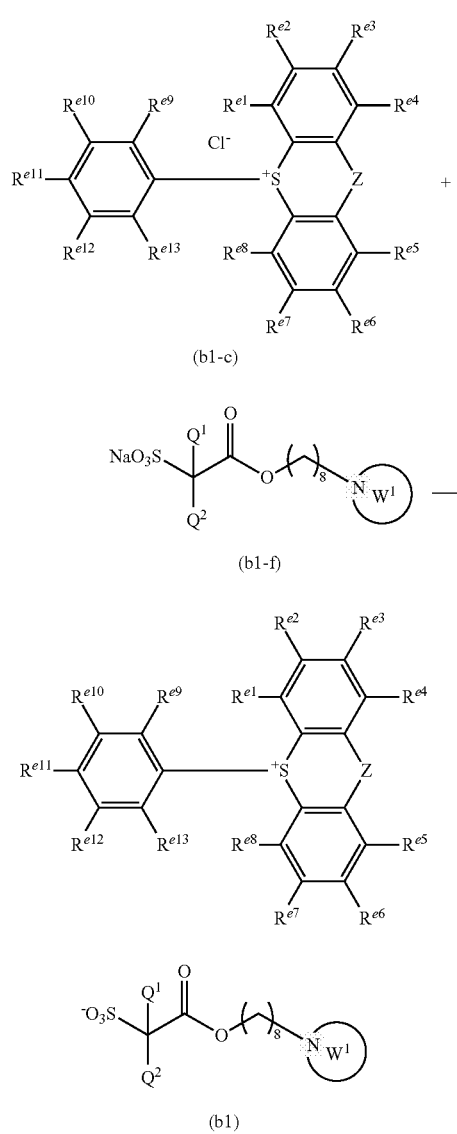

(b1-c)

(b1-f)

(b1)

Preferred examples of the solvent include chloroform. Preferred examples of the acid catalyst include hydrochloric acid.

The above mentioned method can apply to production of the salts (I) wherein $L^1$ is —COO—R— (R is a divalent $C_1$ to $C_{15}$ saturated hydrocarbon group).

<Acid Generator>

The acid generator of the present invention contains the above salt (I) as an essential ingredient. The salt (I) may be used as a single salt or as a combination of two or more salts. Also, the acid generator of the present invention may contain one or more known salt for the acid generator other than the salt (I) (hereinafter is sometimes referred to as "acid generator (B)").

An acid generator (B) is generally classified into non-ionic-based or ionic-based acid generator. The present acid generator may be used either acid generators.

Examples of the non-ionic-based acid generator include organic halogenated compounds; sulfonate esters such as 2-nitrobenzyl ester, aromatic sulfonate, oxime sulfonate, N-sulfonyl oxyimide, sulfonyl oxyketone and diazo naphthoquinone 4-sulfonate; sulfones such as disulfone, ketosulfone and sulfone diazomethane.

Examples of the ionic acid generator includes onium salts containing onium cation (such as diazonium salts, phosphonium salts, sulfonium salts, iodonium salts).

Examples of anion of onium salts include sulfonate anion, sulfonylimide anion and sulfonylmethyde anion.

For the acid generator (B), compounds which generate an acid by radiation described in JP S63-26653A, JP S55-164824A, JP S62-69263A, JP S63-146038A, JP S63-163452A, JP S62-153853A, JP S63-146029A, U.S. Pat. No. 3,779,778B, U.S. Pat. No. 3,849,137B, DE3,914,407B and EP-126,712A can be used.

Also, as the acid generator (B), compounds formed according to conventional methods can be used.

Preferred acid generators (B) in combination of the salt (I) are represented by the formula (B1-1) to the formula (B1-17). Among these, the salt represented by the formulae (B1-1), (B1-2), (B1-6), (B1-11), (B1-12), (B1-13) and (B1-14) which contain triphenyl sulfonium cation, and the formulae (B1-3) and (B1-7) which contain tritolyl sulfonium cation are preferable.

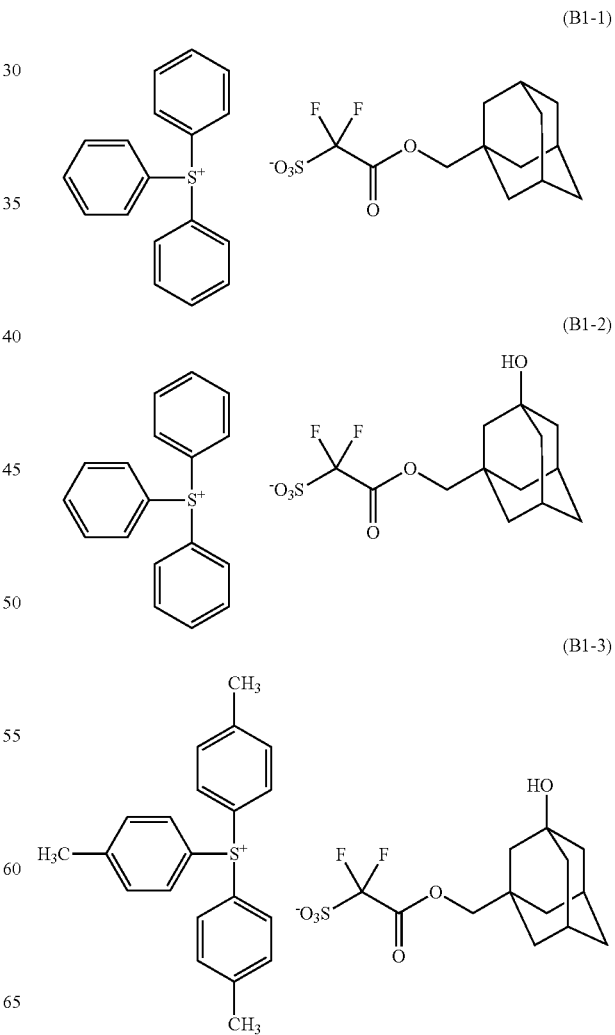

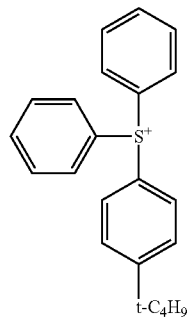 (B1-4)
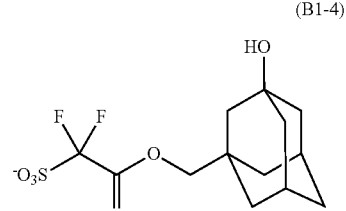
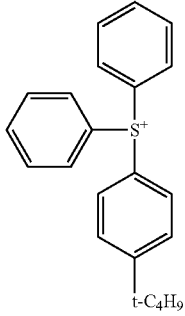 (B1-8)
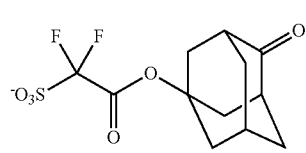
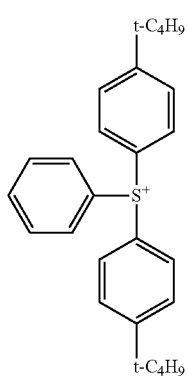 (B1-5)
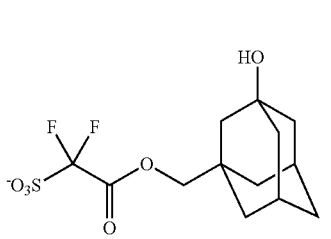
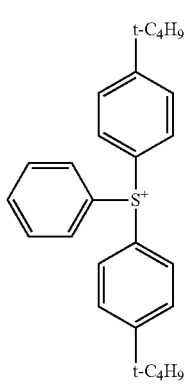 (B1-9)
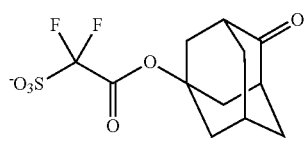
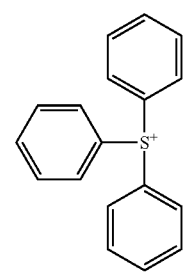 (B1-6)
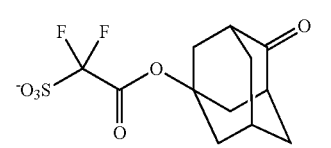
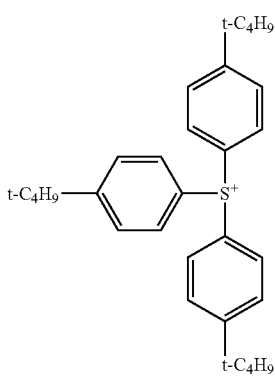 (B1-10)
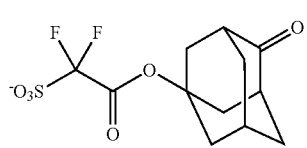
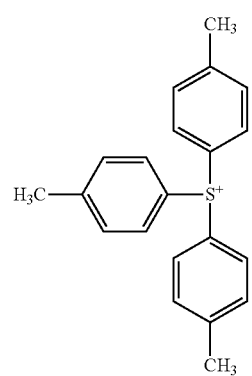 (B1-7)
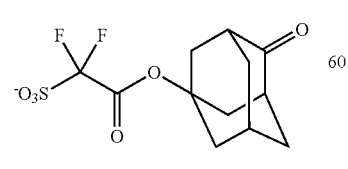
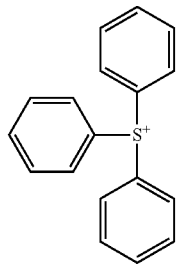 (B1-11)

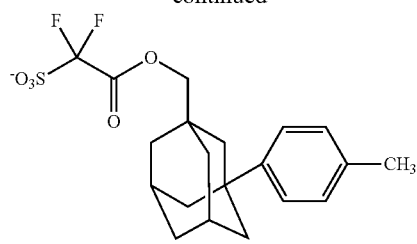

(B1-12)

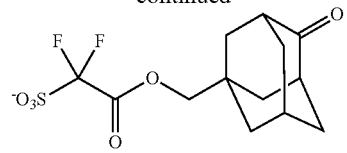

(B1-17)

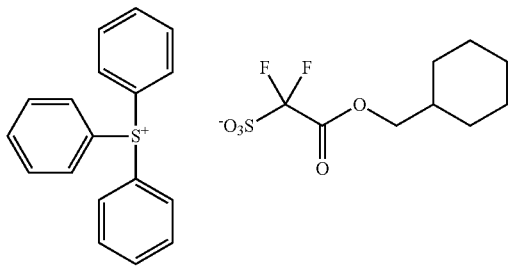

(B1-13)

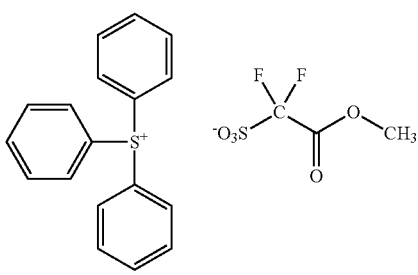

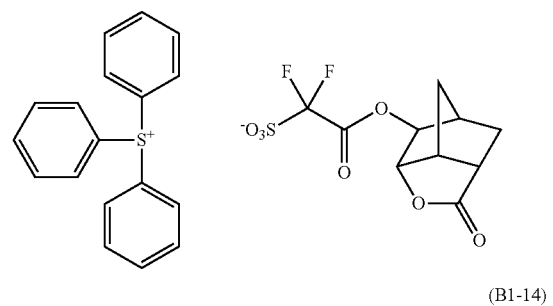

(B1-14)

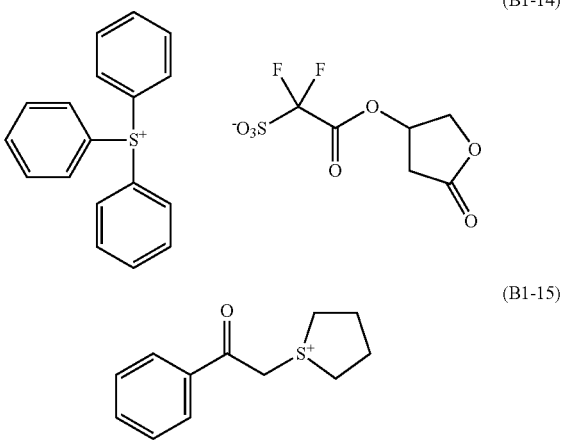

(B1-15)

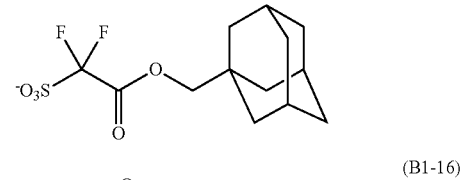

(B1-16)

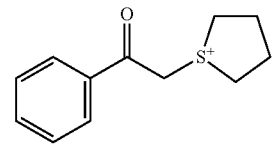

In the acid generator of the present invention, the salt (I) is contained together with the acid generator (B), the salt (I) is preferably not less than 1 parts by weight (and more preferably not less than 2 parts by weight), and not more than 99 parts by weight (and more preferably not more than 98 parts by weight), with respect to 100 parts by weight of the acid generator.

In this case, the weight ratio of the acid generator (I)/acid generator (B) may be 1/99 to 99/1, preferably 3/97 to 50/50, and more preferably 5/95 to 30/70.

<Resist Composition>

The resist composition of the present invention contains;

(A) a resin (hereinafter is sometimes referred to as "resin (A)"), and (B) the acid generator described above.

Moreover, the present resist composition preferably contains a solvent (hereinafter is sometimes referred to as "solvent (D)") and/or an additive such as a basic compound (hereinafter is sometimes referred to as "basic compound (C)") which is known as a quencher in this technical field, as needed.

<Acid Generator>

The acid generator in the resist composition of the present invention contains the salt (I). Further, the present resist composition preferably contains the acid generator (B) other than the salt (I) as described above.

In the resist composition of the present invention, the total amount of the acid generator is preferably not less than 1 parts by weight (and more preferably not less than 3 parts by weight), and not more than 40 parts by weight (and more preferably not more than 35 parts by weight), with respect to 100 parts by weight of the resin (A).

<Resin (A)>

The resin (A) is preferably a resin having properties which is insoluble or poorly soluble in alkali aqueous solution, but becoming soluble in an alkali aqueous solution by the action of an acid in order to produce a resist pattern with excellent focus margin (DOF) by utilizing an acid generated from the acid generator described above at producing a resist pattern. Here "a resin having properties which is insoluble or poorly soluble in alkali aqueous solution, but becomes soluble in an alkali aqueous solution by the action of an acid" means a resin that is insoluble or poorly soluble in aqueous alkali solution before contact with the acid, and becomes soluble in aqueous alkali solution after contact with an acid.

Therefore, the resin (A) is preferably a resin having at least one of the structural unit which contains a labile group to an acid (hereinafter is sometimes referred to as "acid labile group") and is derived from a monomer having the acid labile group. Hereinafter such monomer is sometimes referred to as "acid labile monomer (a1)", and such structural unit is sometimes referred to as "structural unit (a1)".

Also, the resin (A) may include a structural unit other than the structural unit having the acid labile group as long as the resin (A) has above properties.

Examples of the structural unit other than the structural unit having the acid labile group include a structural unit derived from a monomer not having the acid labile group (hereinafter such monomer is sometimes referred to as "acid stable monomer" and such group is sometimes referred to as "acid stable group"), and a structural unit derived from a known monomer in this field.

<Acid Labile Group>

The "acid labile group" means a group which has an elimination group and in which the elimination group is detached by contacting with an acid resulting in forming a hydrophilic group such as a hydroxy or carboxy group. Examples of the acid labile group include a group represented by the formula (1) and a group represented by the formula (2). Hereinafter a group represented by the formula (1) may refer to as an "acid labile group (1)", and a group represented by the formula (2) may refer to as an "acid labile group (2)".

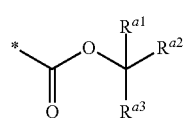

(1)

wherein $R^{a1}$ to $R^{a3}$ independently represent a $C_1$ to $C_8$ alkyl group or a $C_3$ to $C_{20}$ alicyclic hydrocarbon group, or $R^{a1}$ and $R^{a2}$ may be bonded together to form a $C_2$ to $C_{20}$ divalent hydrocarbon group, * represents a bond. In particular, the bond here represents a bonding site (the similar shall apply hereinafter for "bond").

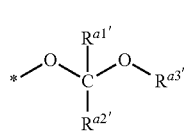

(2)

wherein $R_{a1}'$ and $R^{a2'}$ independently represent a hydrogen atom or a $C_1$ to $C_{12}$ hydrocarbon group, $R^{a3'}$ represents a $C_1$ to $C_{20}$ hydrocarbon group, or $R^{a2'}$ and $R^{a3'}$ may be bonded together to form a divalent $C_2$ to $C_{20}$ hydrocarbon group, and one or more —$CH_2$— contained in the hydrocarbon group or the divalent hydrocarbon group may be replaced by —O— or —S—, * represents a bond.

The alicyclic hydrocarbon group of $R^{a1}$ and $R^{a2}$ preferably has 5 to 16 carbon atoms.

When $R^{a1}$ and $R^{a2}$ is bonded together to form a $C_2$ to $C_{20}$ hydrocarbon group, examples of the group-$C(R^{a1})(R^{a2})(R^{a3})$ include groups below. The divalent hydrocarbon group preferably has 3 to 12 carbon atoms.

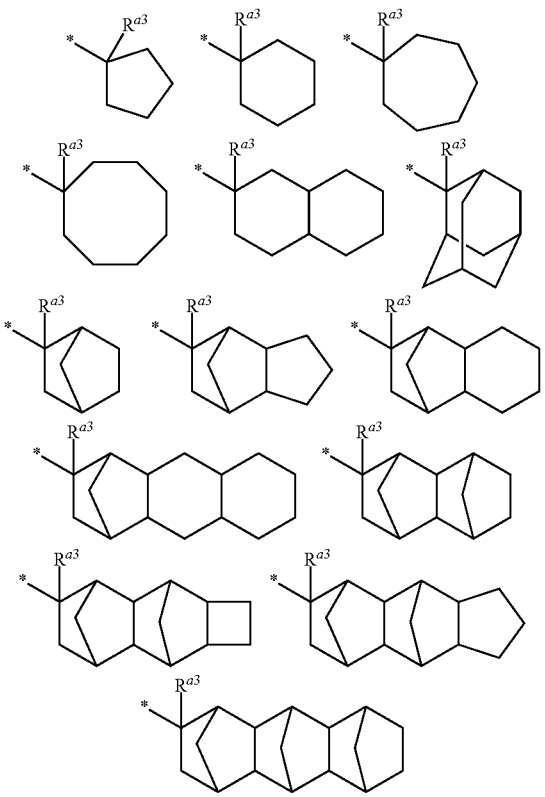

Specific examples of the acid labile group (1) include, for example, 1,1-dialkylalkoxycarbonyl group (a group in which $R^{a1}$ to $R^{a3}$ are alkyl groups, preferably tert-butoxycarbonyl group, in the formula (1)), 2-alkyladamantane-2-yloxycarbonyl group (a group in which $R^{a1}$, $R^{a2}$ and a carbon atom form adamantyl group, and $R^{a3}$ is alkyl group, in the formula (1)), and 1-(adamantine-1-yl)-1-alkylalkoxycarbonyl group (a group in which $R^{a1}$ and $R^{a2}$ are alkyl group, and $R^{a3}$ is adamantyl group, in the formula (1)).

The hydrocarbon group of $R^{a1'}$ to $R^{a3'}$ includes any of an alkyl group, an alicyclic hydrocarbon group and an aromatic hydrocarbon group.

At least one of $R^{a1'}$ and $R^{a2'}$ is preferably a hydrogen atom.

Specific examples of the acid labile group (2) include a group below.

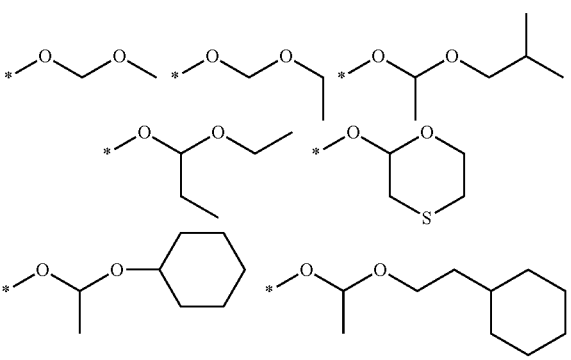

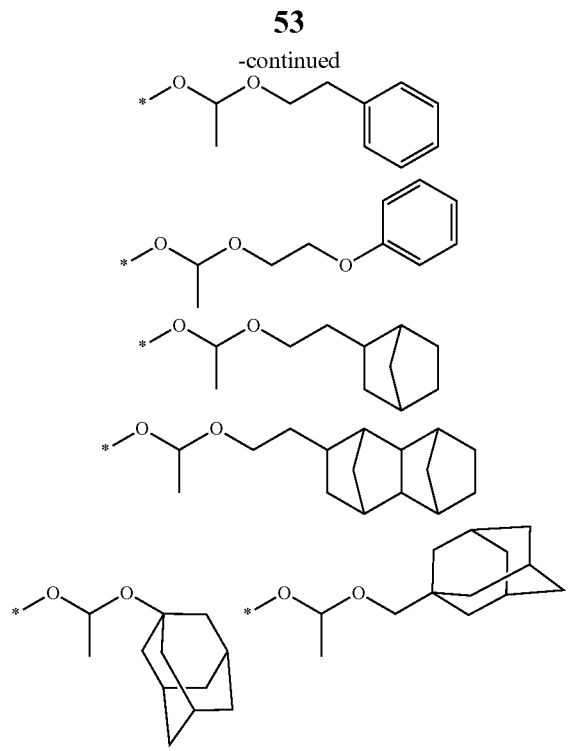

<Acid Labile Monomer (a1)>

The acid labile monomer (a1) is preferably a monomer having an acid labile group and a carbon-carbon double bond, and more preferably a (meth)acrylic monomer having the acid labile group.

Among the (meth)acrylic monomer having an acid labile group, it is preferably a monomer having a $C_5$ to $C_{20}$ alicyclic hydrocarbon group. When a resin which can be obtained by polymerizing monomers having bulky structure such as the alicyclic hydrocarbon group is used, the resist composition having excellent resolution tends to be obtained during the production of a resist pattern.

Examples of the (meth)acrylic monomer having the acid labile group and a carbon-carbon double bond preferably include a monomer giving a structural unit represented by the formula (a1-1) and a monomer giving a structural unit represented by the formula (a1-2), below. Hereinafter such structural units are sometimes referred to as a "structural unit (a1-1)" and a "structural unit (a1-2)" and monomers inducing such structural units are sometimes referred to as a "monomer (a1-1)" and a "monomer (a1-2)". These may be used as a single monomer or as a combination of two or more monomers.

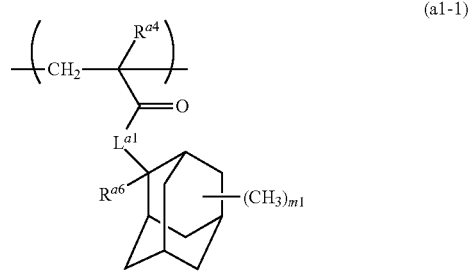

(a1-1)

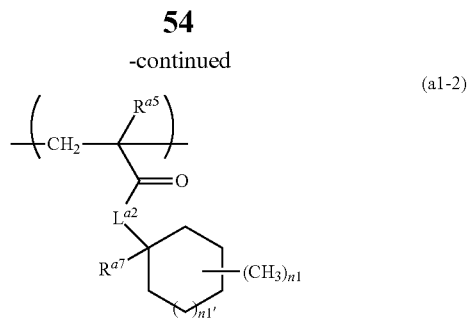

(a1-2)

wherein $L^{a1}$ and $L^{a2}$ independently represent *—O— or *—O—$(CH_2)_{k1}$—CO—O—, k1 represents an integer of 1 to 7, * represents a bond to the carbonyl group;

$R^{a4}$ and $R^{a5}$ independently represent a hydrogen atom or a methyl group;

$R^{a6}$ and $R^{a7}$ independently represent a $C_3$ to $C_{10}$ aliphatic hydrocarbon group;

m1 represents an integer 0 to 14;

n1 represents an integer 0 to 10; and n1' represents an integer 0 to 3.

In the formula (a1-1) and the formula (a1-2), $L^{a1}$ and $L^{a2}$ are preferably *—O— or *—O—$(CH_2)_{k1'}$—CO—O—, here k1' represents an integer of 1 to 4 and more preferably 1, and more preferably *—O—.

$R^{a4}$ and $R^{a5}$ are preferably a methyl group.

The aliphatic hydrocarbon group of $R^{a6}$ and $R^{a7}$ is preferably a $C_1$ to $C_8$ alkyl group or a $C_3$ to $C_{10}$ alicyclic hydrocarbon group, more preferably a $C_1$ to $C_8$ alkyl group or a $C_3$ to $C_8$ alicyclic hydrocarbon group, and still more preferably a $C_1$ to $C_6$ alkyl group or a $C_3$ to $C_6$ alicyclic hydrocarbon group.

m1 is preferably an integer of 0 to 3, and more preferably 0 or 1.

n1 is preferably an integer of 0 to 3, and more preferably 0 or 1.

n1' is preferably 0 or 1, and more preferably 1.

Examples of the monomer giving the structural unit (a1-1) include monomers described in JP 2010-204646A. Among these, the structural units are preferably structural units represented by the formula (a1-1-1) to the formula (a1-1-6), and more preferably structural units represented by the formula (a1-1-1) to the formula (a1-1-3) below.

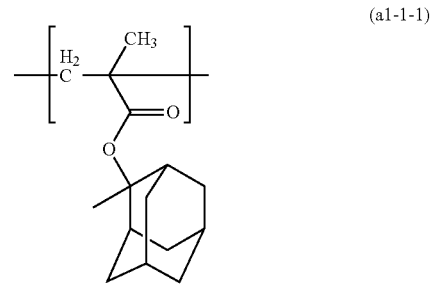

(a1-1-1)

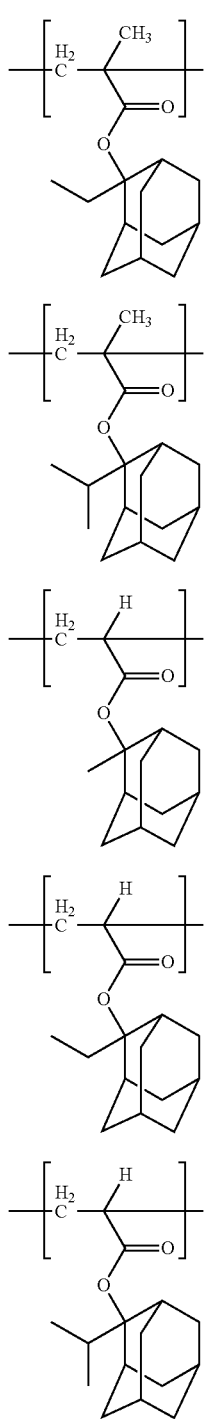

(a1-1-2)

(a1-1-3)

(a1-1-4)

(a1-1-5)

(a1-1-6)

Examples of the monomer (a1-2) include 1-ethylcyclopentane-1-yl(meth)acrylate, 1-ethylcyclohexane-1-yl(meth)acrylate, 1-ethylcycloheptane-1-yl(meth)acrylate, 1-methylcyclopentane-1-yl(meth)acrylate, 1-isopropylcyclopentane-1-yl(meth)acrylate.

Specific examples of the monomer (a1-2) include the monomers giving the structural units represented by the formula (a1-2-1) to the formula (a1-2-6) are preferable, and the monomers giving the structural units represented by the formula (a1-2-3) and the formula (a1-2-4) are more preferable, and the monomer giving the structural units represented by the formula (a1-2-3) are still more preferable.

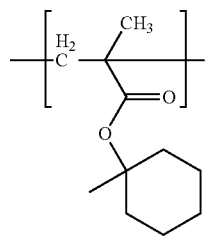

(a1-2-1)

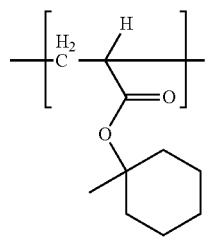

(a1-2-2)

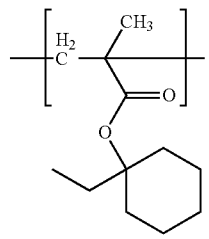

(a1-2-3)

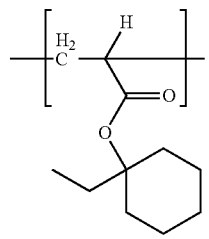

(a1-2-4)

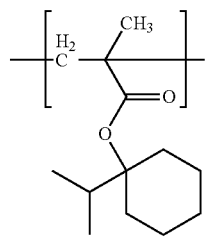

(a1-2-5)

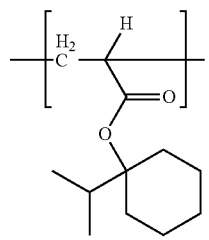

(a1-2-6)

When the resin (A) contains the structural unit (a1-1) and/or the structural unit (a1-2), the total proportion thereof is generally 10 to 95 mol %, preferably 15 to 90 mol %, more preferably 20 to 85 mol %, and still more preferably more preferably 20 to 60 mol %, with respect to the total structural units (100 mol %) of the resin (A).

The proportion of the structural unit derived from the monomer having an adamantyl group (in particular, the monomer having the acid labile group (a1-1)) is preferably 15 mol % or more with respect to the structural units derived from the acid labile monomer (a1). As the mole ratio of the structural unit derived from the monomer having an adamantyl group increases within this range, the dry etching resistance of the resulting resist improves.

For achieving the proportion of the structural unit (a1-1) and/or the structural unit (a1-2) in the resin (A) within the above range, the amount of the monomer (a1-1) and/or a monomer (a1-2) to be used can be adjusted with respect to the total amount of the monomer to be used when the resin (A) is produced (the same shall apply hereinafter for corresponding adjustment of the proportion).

Examples of a monomer having an acid labile group (2) and a carbon-carbon double bond include a monomer represented by the formula (a1-5). Such monomer may be hereinafter referred to as "monomer (a1-5)". When the resin (A) has the structural unit derived from the monomer (a1-5), a resist pattern tends to be obtained with few defects.

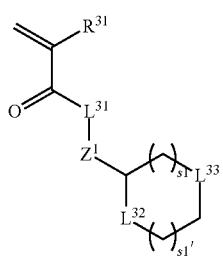
(a1-5)

wherein $R^{31}$ represents a hydrogen atom, a halogen atom or a $C_1$ to $C_6$ alkyl group that optionally has a halogen atom;

$L^{31}$, $L^{32}$ and $L^{33}$ independently represent *—O—, *—S— or *—O—$(CH_2)_{k4}$—CO—O—, k4 represents an integer of 1 to 7, * represents a bond to the carbonyl group (—CO—);

s1 represents an integer of 0 to 4;

s1' represents an integer of 0 to 4;

$Z^1$ represents a single bond or a $C_1$ to $C_6$ alkanediyl group, and one or more —$CH_2$— contained in the alkanediyl group may be replaced by —O— or —CO—.

In the formula (a1-5), $R^{31}$ is preferably a hydrogen atom, a methyl group or trifluoromethyl group;

$L^1$ is preferably —O—;

$L^2$ and $L^3$ are independently preferably *—O— or *—S—, and more preferably —O— for one and —S— for another;

s1 is preferably 1;

s1' is preferably an integer of 0 to 2;

$Z^1$ is preferably a single bond or —$CH_2$—CO—O—.

Examples of the monomer represented by the formula (a1-5) include monomers described below.

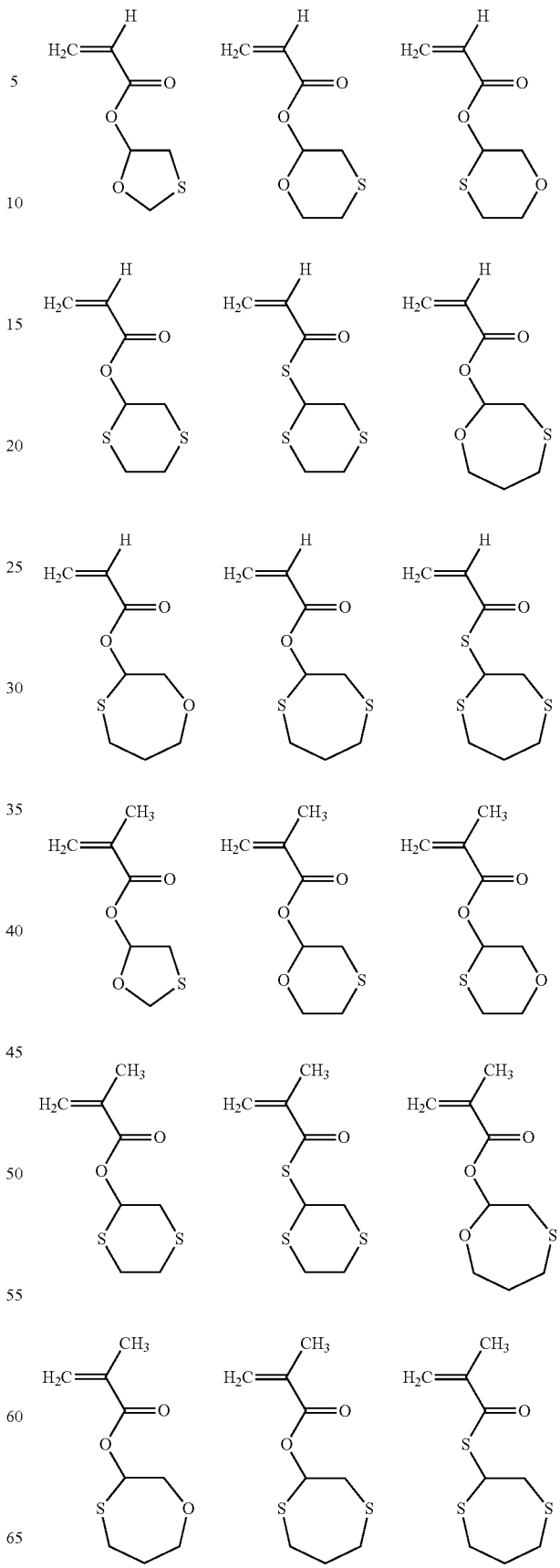

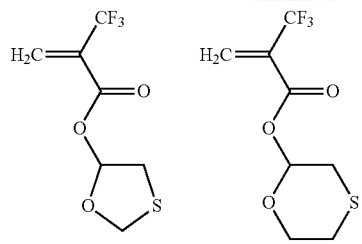
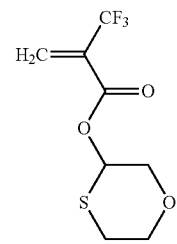
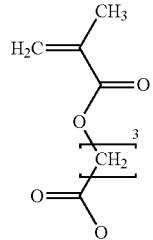
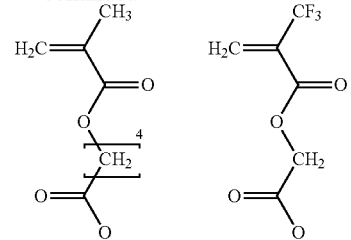

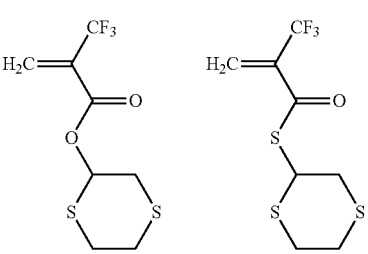
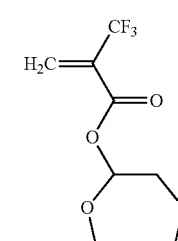
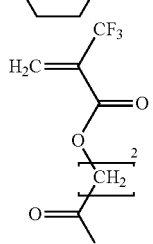
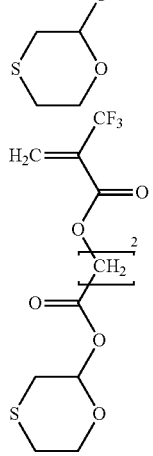
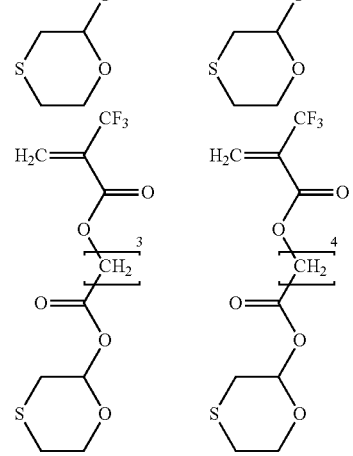

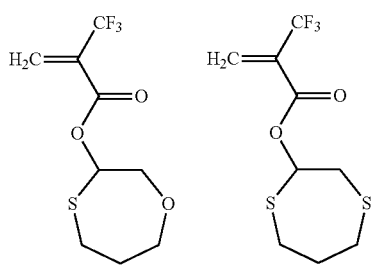
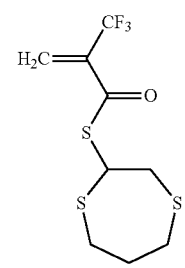

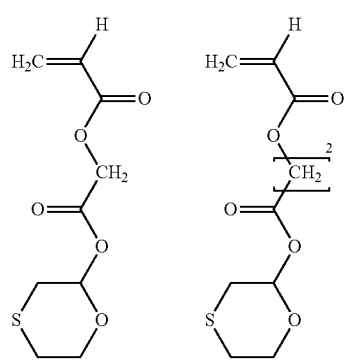
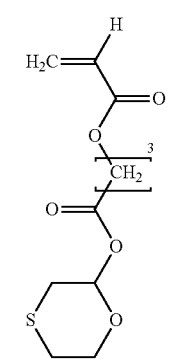
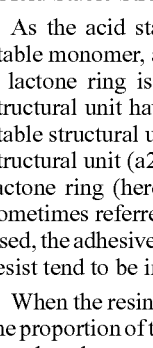

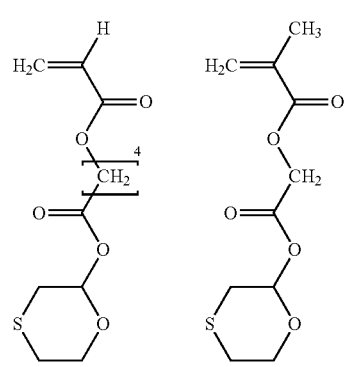
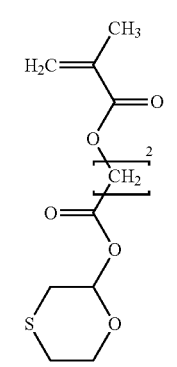

When the resin (A) contains the structural unit derived from the monomer (a1-5), the proportion thereof is generally 1 to 95 mol %, preferably 3 to 90 mol %, and more preferably 5 to 85 mol %, with respect to the total structural units (100 mol %) constituting the resin (A).

<Acid Stable Structural Unit>

As the acid stable structural unit derived from the acid stable monomer, a structural unit having a hydroxy group or a lactone ring is preferable. When a resin containing the structural unit having hydroxy group (hereinafter such acid stable structural unit is sometimes referred to as "acid stable structural unit (a2)") or a acid stable structural unit having a lactone ring (hereinafter such acid stable structural unit is sometimes referred to as "acid stable structural unit (a3)") is used, the adhesiveness of resist to a substrate and resolution of resist tend to be improved.

When the resin (A) contains the acid stable structural unit, the proportion of the acid stable structural unit can be adjusted based on the amount of the acid labile structural unit (a1). For example, the ratio of [the acid labile structural unit (a1)]: [the acid stable structural unit] is preferably 10 to 80 mol %:90 to 20 mol %, and more preferably 20 to 60 mol %:80 to 40 mol %.

Within this range of the ratio, the dry etching resistance of the resulting resist composition improves.

<Acid Stable Structural Unit (a2)>

The acid stable structural unit (a2), which has the hydroxy group, is preferably selected depending on the kinds of an exposure light source at producing the resist pattern.

When KrF excimer laser lithography (248 nm), or high-energy irradiation such as electron beam or EUV light is used for the resist composition, using the acid stable structural unit having a phenolic hydroxy group such as hydroxystyrene, represented by the formula (a2-0), as the acid stable structural unit (a2) is preferable.

When ArF excimer laser lithography (193 nm), i.e., short wavelength excimer laser lithography is used, using the acid stable structural unit having a hydroxy adamantyl group represented by the formula (a2-1) as the acid stable structural unit (a2) is preferable.

The acid stable structural unit (a2) having the hydroxy group may be used as a single structural unit or as a combination of two or more structural unit.

Examples of the acid stable structural unit having phenolic hydroxy group include styrene-based structural units represented by the formula (a2-0) (hereinafter the structural unit is sometimes referred to as "acid stable structural unit (a2-0)") based on such as p- or m-hydroxystyrene.

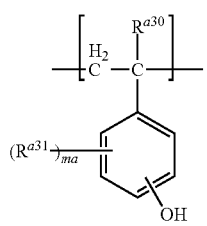

(a2-0)

wherein $R^{a30}$ represents a hydrogen atom, a halogen atom or a $C_1$ to $C_6$ alkyl group that optionally has a halogen atom;

$R^{a31}$ in each occurrence independently represents a halogen atom, a hydroxy group, a $C_1$ to $C_6$ alkyl group, a $C_1$ to $C_6$ alkoxy group, a $C_2$ to $C_4$ acyl group, a $C_2$ to $C_4$ acyloxy group, an acryloyl group or methacryloyl group;

ma represents an integer 0 to 4.

In the formula (a2-0), examples of the alkyl group having a halogen atom of $R^{a30}$ include trifluoromethyl, perfluoroethyl, perfluoropropyl, perfluoro-isopropyl, perfluorobutyl, perfluoro-sec-butyl, perfluoro-tert-butyl, perfluoropentyl, perfluorohexyl, trichloromethyl, perburomomethyl and periodomethyl groups.

The alkyl group of $R^{a30}$ and $R^{a31}$ is preferably a $C_1$ to $C_4$ alkyl group, more preferably a $C_1$ to $C_2$ alkyl group, and still more preferably methyl group.

The alkoxy group of Ranis preferably a $C_1$ to $C_4$ alkoxy group, more preferably a $C_1$ to $C_2$ alkoxy group, and still more preferably methoxy group.

ma is preferably 0, 1 or 2, more preferably 0 or 1, and still more preferably 0.

The acid stable structural unit (a2-0) is preferably structural units described below.

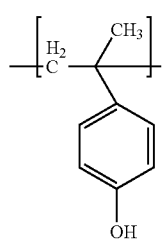

(a2-0-1)

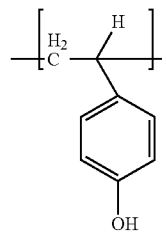

(a2-0-2)

When the resin (A) is produced using the acid stable monomer giving the structural unit (a2-0), p-hydroxystylene or p-hydroxy-α-methylstylene is used as the monomer. Also, a monomer in which the phenolic hydroxy group is protected by a protecting group can be used. Such protecting group may be a group which can be deprotected through contact with an acid. Because the phenolic hydroxy group protected by the protecting group is deprotected through contact with the acid, the acid stable monomer can be easily obtained. However, because the resin (A) has the structural unit derived from the monomer having the acid labile group (a1) as described above, when the phenolic hydroxy group protected by the protecting group is depeotected, the phenolic hydroxy group is preferably placed in contact with a base, so that the acid labile group does not get seriously impaired. Examples of the protecting group which is deprotectable by the base include an acetyl group. Examples of the base include 4-dimethylaminopyrizine and triethylamine.

When the resin (A) contains the structural unit represented by the formula (a2-0), the proportion thereof is generally 90 mol % or less, preferably 10 to 85 mol %, and more preferably 15 to 80 mol %, with respect to the total structural units constituting the resin (A).

Examples of the acid stable structural unit having hydroxy adamantyl include the monomer represented by the formula (a2-1).

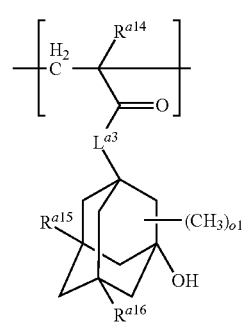

(a2-1)

wherein $L^{a3}$ represents —O— or *—O—$(CH_2)_{k2}$—CO—O—;

k2 represents an integer of 1 to 7;

* represents a bind to —CO—;

$R^{a14}$ represents a hydrogen atom or a methyl group;

$R^{a15}$ and $R^{a16}$ independently represent a hydrogen atom, a methyl group or a hydroxy group;

o1 represents an integer of 0 to 10.

In the formula (a2-1), $L^{a3}$ is preferably —O—, —O—$(CH_2)_{f1}$—CO—O—, here f1 represents an integer of 1 to 4, and more preferably —O—.

$R^{a14}$ is preferably a methyl group.

$R^{a15}$ is preferably a hydrogen atom.

$R^{a16}$ is preferably a hydrogen atom or a hydroxy group.

o1 is preferably an integer of 0 to 3, and more preferably an integer of 0 or 1.

Examples of the acid stable structural unit (a2-1) include structural units described in JP 2010-204646A. Among these, the structural units are preferably structural units represented by the formula (a2-1-1) to the formula (a2-1-6), more preferably structural units represented by the formula (a2-1-1) to the formula (a2-1-4), and still more preferably structural units represented by the formula (a2-1-1) and the formula (a2-1-3) below.

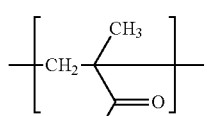
(a2-1-1)

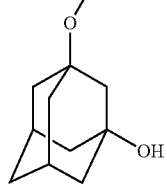
(a2-1-2)

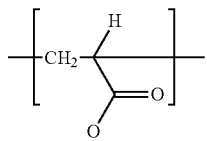
(a2-1-3)

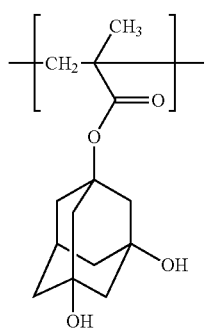
(a2-1-4)

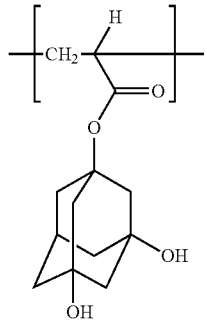

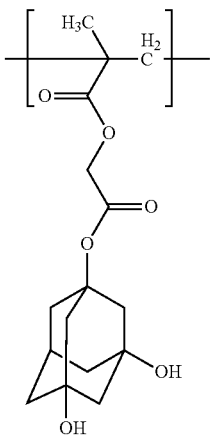
(a2-1-5)

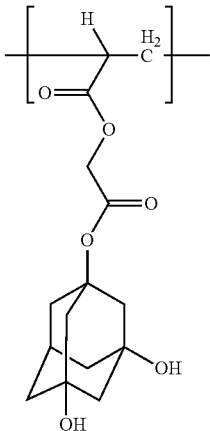
(a2-1-6)

When the resin (A) contains the acid stable structural unit represented by the formula (a2-1), the proportion thereof is generally 3 to 45 mol %, preferably 5 to 40 mol %, and more preferably 5 to 35 mol % with respect to the total structural units (100 mol %) constituting the resin (A).

<Acid Stable Structural Unit (a3)>

The lactone ring included in the acid stable structural unit (a3) may be a monocyclic compound such as β-propiolactone ring, γ-butyrolactone, δ-valerolactone, or a condensed ring with monocyclic lactone ring and other ring. Among these, γ-butyrolactone and condensed ring with γ-butyrolactone and other ring are preferable.

Examples of the acid stable structural unit (a3) having the lactone ring include structural units represented by the formula (a3-1), the formula (a3-2) and the formula (a3-3). These structural units may be used as a single structural unit or as a combination of two or more structural units.

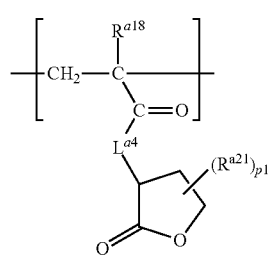
(a3-1)

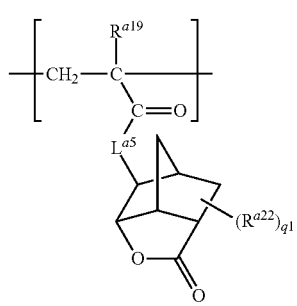

(a3-2)

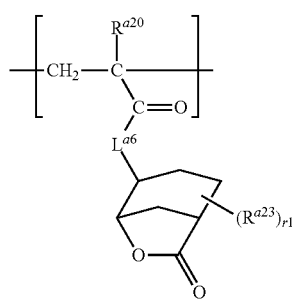

(a3-3)

wherein $L^{a4}$ to $L^{a6}$ independently represent —O— or *—O—$(CH_2)_{k3}$—CO—O—;

k3 represents an integer of 1 to 7, * represents a bind to —CO—;

$R^{a18}$ to $R^{a20}$ independently represent a hydrogen atom or a methyl group;

$R^{a21}$ in each occurrence represents a $C_1$ to $C_4$ aliphatic hydrocarbon group;

p1 represents an integer of 0 to 5;

$R^{a22}$ to $R^{a23}$ in each occurrence independently represent a carboxyl group, cyano group, and a $C_1$ to $C_4$ aliphatic hydrocarbon group;

q1 and r1 independently represent an integer of 0 to 3.

In the formulae (a3-1) to (a3-3), $L^{a4}$ to $L^{a6}$ include the same group as described in $L^{a3}$ above, and are independently preferably —O—, *—O—$(CH_2)_{k31}$—CO—O—, here k3' represents an integer of 1 to 4 (preferably 1), and more preferably —O—;

$R^{a18}$ to $R^{a21}$ are independently preferably a methyl group.

$R^{a22}$ and $R^{a23}$ are independently preferably a carboxyl group, cyano group or methyl group;

p1 to r1 are independently preferably an integer of 0 to 2, and more preferably an integer of 0 or 1.

Examples of the structural unit (a3) include structural units described in JP 2010-204646A. Among these, the structural units are preferably structural units represented by the formula (a3-1-1) to the formula (a3-1-4), the formula (a3-2-1) to the formula (a3-2-4), the formula (a3-3-1) to the formula (a3-3-4), more preferably structural units represented by the formula (a3-1-1) to the formula (a3-1-2), the formula (a3-2-3) to the formula (a3-2-4), and still more preferably structural units represented by the formula (a3-1-1) and the formula (a3-2-3) below.

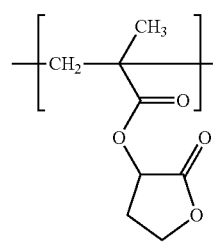

(a3-1-1)

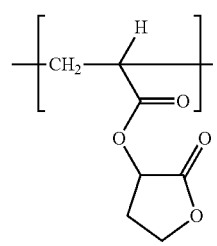

(a3-1-2)

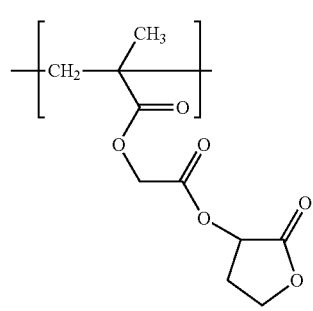

(a3-1-3)

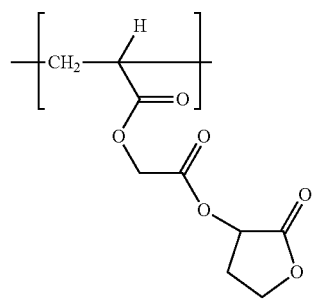

(a3-1-4)

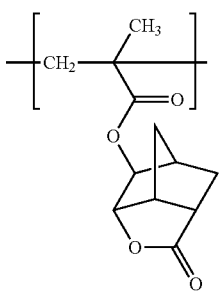

(a3-2-1)

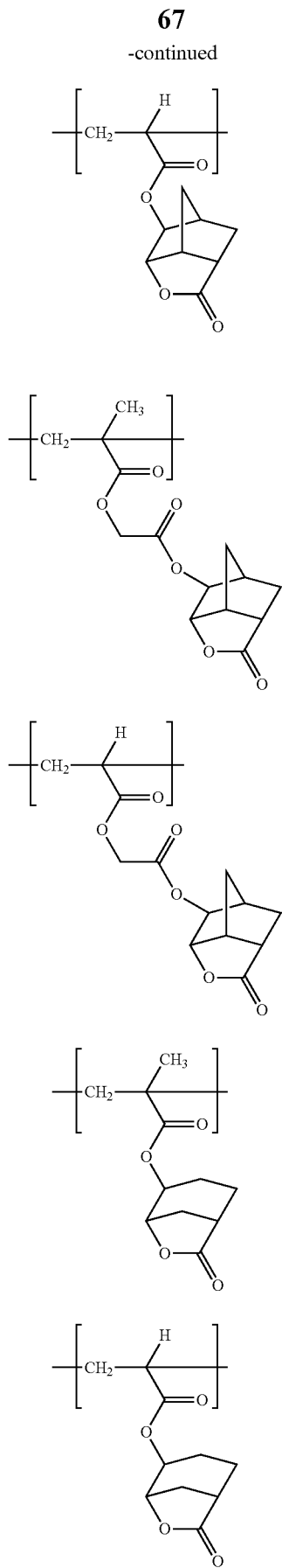

(a3-2-2)
(a3-2-3)
(a3-2-4)
(a3-3-1)
(a3-3-2)

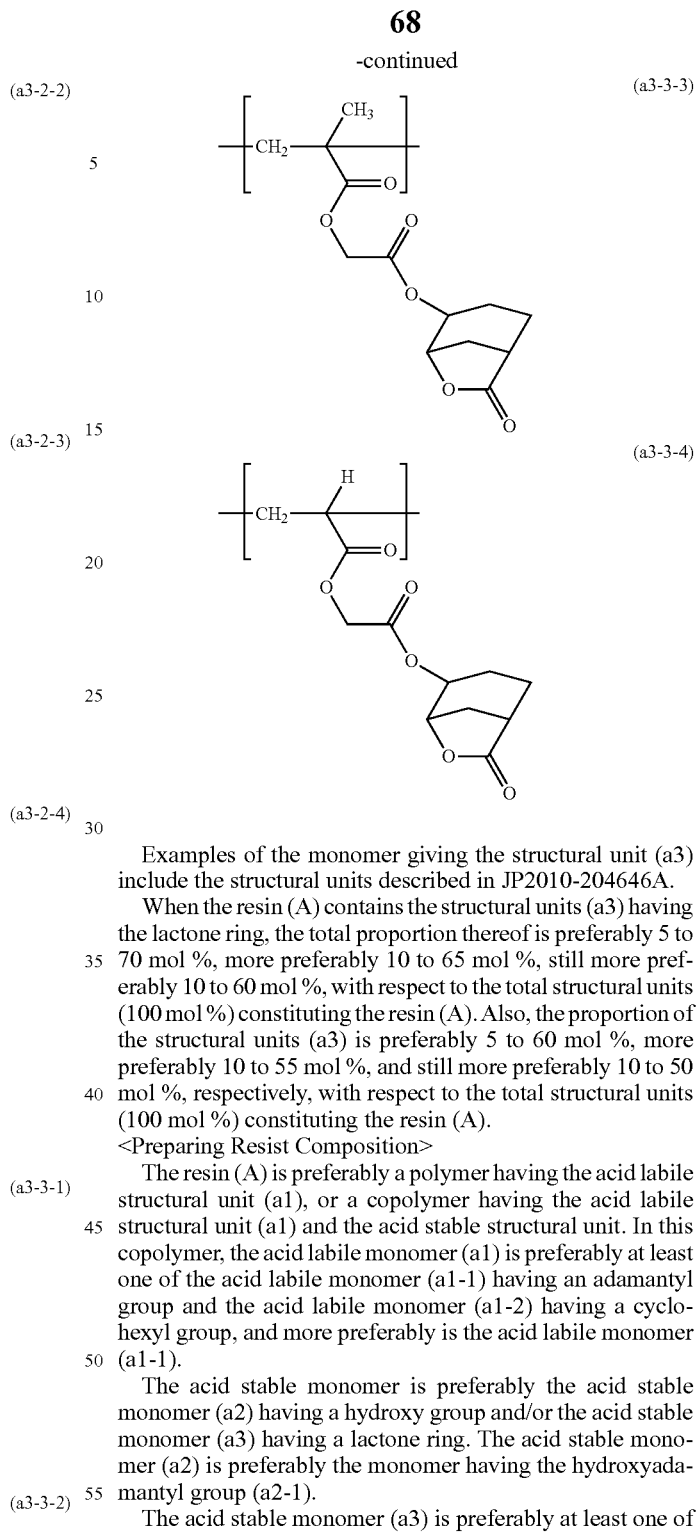

(a3-3-3)
(a3-3-4)

Examples of the monomer giving the structural unit (a3) include the structural units described in JP2010-204646A.

When the resin (A) contains the structural units (a3) having the lactone ring, the total proportion thereof is preferably 5 to 70 mol %, more preferably 10 to 65 mol %, still more preferably 10 to 60 mol %, with respect to the total structural units (100 mol %) constituting the resin (A). Also, the proportion of the structural units (a3) is preferably 5 to 60 mol %, more preferably 10 to 55 mol %, and still more preferably 10 to 50 mol %, respectively, with respect to the total structural units (100 mol %) constituting the resin (A).

<Preparing Resist Composition>

The resin (A) is preferably a polymer having the acid labile structural unit (a1), or a copolymer having the acid labile structural unit (a1) and the acid stable structural unit. In this copolymer, the acid labile monomer (a1) is preferably at least one of the acid labile monomer (a1-1) having an adamantyl group and the acid labile monomer (a1-2) having a cyclohexyl group, and more preferably is the acid labile monomer (a1-1).

The acid stable monomer is preferably the acid stable monomer (a2) having a hydroxy group and/or the acid stable monomer (a3) having a lactone ring. The acid stable monomer (a2) is preferably the monomer having the hydroxyadamantyl group (a2-1).

The acid stable monomer (a3) is preferably at least one of the monomer having the γ-butyrolactone ring (a3-1) and the monomer having the condensed ring of the γ-butyrolactone ring and the norbornene ring (a3-2).

The resin (A) can be produced by a known polymerization method, for example, radical polymerization method, using at least one of the acid labile monomer (a1) and/or at least one of the acid stable monomer (a2) having a hydroxy group and/or at least one of the acid stable monomer (a3) having a lactone ring and/or at least one of a known compound.

The weight average molecular weight of the resin (A) is preferably 2,500 or more (more preferably 3,000 or more, and still more preferably 4,000 or more), and 50,000 or less (more preferably 30,000 or less, and still more preferably 15,000 or less). The weight average molecular weight is a value determined by gel permeation chromatography using polystyrene as the standard product. The detailed condition of this analysis is described in Examples.

The proportion of the resin (A) can be adjusted with respect to the total solid proportion of the resist composition. For example, the resist composition of the present invention preferably contains 80 weight % or more and 99 weight % or less of the resin (A), with respect to the total solid proportion of the resist composition.

In the specification, the term "solid proportion of the resist composition" means the entire proportion of all ingredients other than the solvent (E).

The proportion of the resin (A) and the solid proportion of the resist composition can be measured with a known analytical method such as, for example, liquid chromatography and gas chromatography.

<Basic Compound (C)>

The resist composition of the present invention may contain a basic compound (C). The basic compound (C) is a compound having a property to quench an acid, in particular, generated from the acid generator, and called "quencher".

As the basic compounds (C), nitrogen-containing basic compounds (for example, amine and basic ammonium salt) are preferable. The amine may be an aliphatic amine or an aromatic amine. The aliphatic amine includes any of a primary amine, secondary amine and tertiary amine. The aromatic amine includes an amine in which an amino group is bonded to an aromatic ring such as aniline, and a heteroaromatic amine such as pyridine.

Preferred basic compounds (C) include compounds presented by the formula (C1) to the formula (C8) as described below. Among these, the basic compound presented by the formula (C1-1) is more preferable.

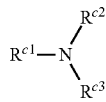
(C1)

wherein $R^{c1}$, $R^{c2}$ and $R^{c3}$ independently represent a hydrogen atom, a $C_1$ to $C_6$ alkyl group, $C_5$ to $C_{10}$ alicyclic hydrocarbon group or a $C_6$ to $C_{10}$ aromatic hydrocarbon group, one or more hydrogen atom contained in the alkyl group and alicyclic hydrocarbon group may be replaced by a hydroxy group, an amino group or a $C_1$ to $C_6$ alkoxyl group, one or more hydrogen atom contained in the aromatic hydrocarbon group may be replaced by a $C_1$ to $C_6$ alkyl group, a $C_1$ to $C_6$ alkoxyl group, a $C_5$ to $C_{10}$ alicyclic hydrocarbon group or a $C_6$ to $C_{10}$ aromatic hydrocarbon group.

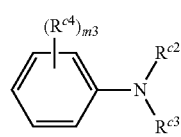
(C1-1)

wherein $R^{c2}$ and $R^{c3}$ have the same definition of the above; $R^{c4}$ in each occurrence represents a $C_1$ to $C_6$ alkyl group, a $C_1$ to $C_6$ alkoxyl group, a $C_5$ to $C_{10}$ alicyclic hydrocarbon group or a $C_6$ to $C_{10}$ aromatic hydrocarbon group;

m3 represents an integer 0 to 3.

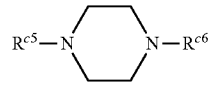
(C2)

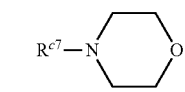
(C3)

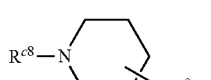
(C4)

wherein $R^{c5}$, $R^{c6}$, $R^{c7}$ and $R^{c8}$ independently represent the any of the group as described in $R^{c1}$ of the above;

$R^{c9}$ in each occurrence independently represents a $C_1$ to $C_6$ alkyl group, a $C_3$ to $C_6$ alicyclic hydrocarbon group or a $C_2$ to $C_6$ alkanoyl group;

n3 represents an integer of 0 to 8.

Examples of the alkanoyl group include acetyl group, 2-methylacetyl group, 2,2-dimethylacetyl group, propionyl group, butylyl group, isobutylyl group, pentanoyl group, and 2,2-dimethylpropionyl group.

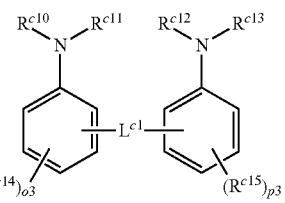
(C5)

(C6)

wherein $R^{c10}$, $R^{c11}$, $R^{c12}$, $R^{c13}$ and $R^{c16}$ independently represent the any of the groups as described in $R^{c1}$;

$R^{c14}$, $R^{c15}$ and $R^{c17}$ in each occurrence independently represent the any of the groups as described in $R^{c4}$;

o3 and p3 represent an integer of 0 to 3;

$L^{c1}$ represents a divalent $C_1$ to $C_6$ alkanediyl group, —CO—, —C(=NH)—, —S— or a combination thereof.

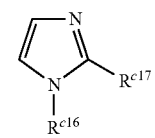
(C7)

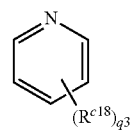
(C8)

wherein $R^{c18}$, $R^{c19}$ and $R^{c20}$ in each occurrence independently represent the any of the groups as described in $R^{c4}$;

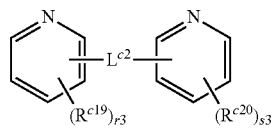

q3, r3 and s3 represent an integer of 0 to 3;

$L^{c2}$ represents a single bond, a $C_1$ to $C_6$ alkanediyl group, —CO—, —C(=NH)—, —S— or a combination thereof.

Specific examples of the amine represented by the formula (C1) include 1-naphtylamine and 2-naphtylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl] amine, triisopropanolamine, ethylene diamine, tetramethylene diamine, hexamethylene diamine, 4,4'-diamino-1,2-diphenylethane, 4,4'-diamino-3,3'-dimethyldiphenylmethane and 4,4'-diamino-3,3'-diethyldiphenylmethane.

Among these, diisopropylaniline is preferable, particularly 2,6-diisopropylaniline is more preferable as the basic compounds (C) contained in the present resist composition.

Specific examples of the compound represented by the formula (C2) include, for example, piperadine.

Specific examples of the compound represented by the formula (C3) include, for example, morpholine.

Specific examples of the compound represented by the formula (C4) include, for example, piperidine, a hindered amine compound having piperidine skeleton described in JP H11-52575-A.

Specific examples of the compound represented by the formula (C5) include, for example, 2,2'-methylenebisaniline.

Specific examples of the compound represented by the formula (C6) include, for example, imidazole and 4-methylimidazole.

Specific examples of the compound represented by the formula (C7) include, for example, pyridine and 4-methylpyrizine.

Specific examples of the compound represented by the formula (C8) include, for example, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl)propane, 1,2-di(4-pyridyloxy)ethane, di(2-pyridyl)ketone, 4,4'-dipyridyl sulfide, 4,4'-dipyridyl disulfide, 2,2'-dipyridylamine, 2,2'-dipicolylamine and bipyridine.

Examples of the ammonium salt include tetramethylammonium hydroxide, tetraisopropylammonium hydroxide, tetrabutylammonium hydroxide, tetrahexylammonium hydroxide, tetraoctylammonium hydroxide, phenyltrimethyl ammonium hydroxide, 3-(trifluoromethyl)phenyltrimethylammonium hydroxide, tetra-n-butyl ammonium salicylate and choline.

The proportion of the basic compound (C) is preferably 0.01 to 5 weight %, more preferably 0.01 to 3 weight %, and still more preferably 0.01 to 1 weight % with respect to the total solid proportion of the resist composition.

<Solvent (D)>

The resist composition of the present invention preferably includes a solvent (D). The solvent (D) can be preferably selected depending on the kinds and an amount of the resin (A) having the structural unit derived from the compound (a), and a kind and an amount of the acid generator from a viewpoint of good coating properties.

Examples of the solvent (D) include glycol ether esters such as ethylcellosolve acetate, methylcellosolve acetate and propylene glycol monomethyl ether acetate; glycol ethers such as propylene glycol monomethyl ether; ethers such as diethylene glycol dimethyl ether; esters such as ethyl lactate, butyl acetate, amyl acetate and ethyl pyruvate; ketones such as acetone, methyl isobutyl ketone, 2-heptanone and cyclohexanone; and cyclic esters such as γ-butyrolactone. These solvents may be used as a single solvent or as a mixture of two or more solvents.

The proportion of the solvent (D) 90 weight % or more, preferably 92 weight % or more, and more preferably 94 weight % or more, and also preferably 99 weight % or less and more preferably 99.9 weight % or less. The proportion of the solvent (D) can be measured with a known analytical method such as, for example, liquid chromatography and gas chromatography.

<Other Ingredient (Hereinafter is Sometimes Referred to as "Other Ingredient (F)")>

The resist composition can also include small amounts of various additives such as a macromolecular compound other than resin (A), sensitizers, dissolution inhibitors, surfactants, stabilizers, and dyes, as needed.

<Preparing the Resist Composition>

The present resist composition can be prepared by mixing the resin (A) and the acid generator, and the basic compound (C), the solvent (D) and the other ingredient (F) as needed. There is no particular limitation on the order of mixing. The mixing may be performed in an arbitrary order. The temperature of mixing may be adjusted to an appropriate temperature within the range of 10 to 40° C., depending on the kinds of the resin and solubility in the solvent (D) of the resin. The time of mixing may be adjusted to an appropriate time within the range of 0.5 to 24 hours, depending on the mixing temperature. There is no particular limitation to the tool for mixing. An agitation mixing may be adopted. The amount of each ingredient in the resist composition can be adjusted by selecting the amount of each ingredient to be used when the resist composition is prepared.

After mixing the above ingredients, the present resist compositions can be prepared by filtering the mixture through a filter having about 0.003 to 0.2 μm pore diameter.

<Method for Producing Resist Pattern>

The method for producing a resist pattern of the present invention includes the steps of:

(1) applying the resist composition of the present invention onto a substrate;

(2) drying the applied composition to form a composition layer;

(3) exposing the composition layer;

(4) heating the exposed composition layer, and (5) developing the heated composition layer.

Applying the resist composition onto the substrate can generally be carried out through the use of a resist application device, such as a spin coater known in the field of semiconductor microfabrication technique. The thickness of the applied resist composition layer can be adjusted by controlling the variable conditions of the resist application device. These conditions can be selected based on a pre-experiment carried out beforehand. The substrate can be selected from various substrates intended to be microfabricated. The substrate may be washed, and an organic antireflection film may be formed on the substrate by use of a commercially available antireflection composition, before the application of the resist composition.

Drying the applied composition layer, for example, can be carried out using a heating device such as a hotplate (so-called "prebake"), a decompression device, or a combination thereof. Thus, the solvent evaporates from the resist composition and a composition layer with the solvent removed is formed. The condition of the heating device or the decompression device can be adjusted depending on the kinds of the solvent used. The temperature in this case is generally within the range of 50 to 200° C. Moreover, the pressure is generally within the range of 1 to $1.0 \times 10^5$ Pa.

The composition layer thus obtained is generally exposed using an exposure apparatus or a liquid immersion exposure apparatus. The exposure is generally carried out through a mask (photomask) that corresponds to the desired pattern. Various types of exposure light source can be used, such as irradiation with ultraviolet lasers such as KrF excimer laser (wavelength: 248 nm), ArF excimer laser (wavelength: 193 nm), $F_2$ excimer laser (wavelength: 157 nm), or irradiation with far-ultraviolet wavelength-converted laser light from a solid-state laser source (YAG or semiconductor laser or the like), or vacuum ultraviolet harmonic laser light or the like. Also, the exposure device may be one which irradiates electron beam or extreme-ultraviolet light (EUV). In this specification, the "exposure" means irradiation of these radiations.

The composition layer may be formed with an exposed portion and an unexposed portion by the above exposure carried out through the mask. In the exposed portion, acid is produced from the acid generator contained in the resist composition upon receiving the energy of the exposure. Thus, the acid labile group contained in the resin (A) reacts with the acid to eliminate the protecting group. As the result, the resin in the exposed portion of the composition layer becomes soluble in an alkali aqueous solution. On the other hand, in the unexposed portion, the resin (A) remains insoluble or poorly soluble in an alkali aqueous solution because of the lack of exposure. In this way, the solubility in the alkali solution will be different between the composition layer in the exposed portion and the composition layer in the unexposed portion.

After exposure, the composition layer is subjected to a heat treatment (so-called "post-exposure bake"). The heat treatment can be carried out using a heating device such as a hotplate. The heating temperature is generally in the range of 50 to 200° C., preferably in the range of 70 to 150° C. The deprotection reaction is promoted by this heat treatment.

The composition layer is developed after the heat treatment, generally with an alkaline developing solution and using a developing apparatus. The development here means to bring the composition layer after the heat treatment into contact with an alkaline solution. Thus, the exposed portion of the composition layer is dissolved by the alkaline solution and removed, and the unexposed portion of the composition layer remains on the substrate, whereby producing a resist pattern. Here, as the alkaline developing solution, various types of aqueous alkaline solutions used in this field can be used. Examples include aqueous solutions of tetramethylammonium hydroxide and (2-hydroxyethyl)trimethylammonium hydroxide (common name: choline).

After the development, it is preferable to rinse the substrate and the pattern with ultrapure water and to remove any residual water thereon.

<Application>

The resist composition of the present invention is useful as the resist composition for excimer laser lithography such as with ArF, KrF or the like, and the resist composition for electron beam (EB) exposure lithography and extreme-ultraviolet (EUV) exposure lithography, as well as liquid immersion exposure lithography.

The resist composition of the present invention can be used in semiconductor microfabrication and in manufacture of liquid crystals, thermal print heads for circuit boards and the like, and furthermore in other photofabrication processes, which can be suitably used in a wide range of applications.

EXAMPLES

The present invention will be described more specifically by way of examples, which are not construed to limit the scope of the present invention.

All percentages and parts expressing the content or amounts used in the Examples and Comparative Examples are based on weight, unless otherwise specified.

The weight average molecular weight is a value determined by gel permeation chromatography.

Column: TSK gel Multipore HXL-M×3+guardcolumn (Tosoh Co. Ltd.)
Eluant: tetrahydrofuran
Flow rate: 1.0 mL/min
Detecting device: RI detector
Column temperature: 40° C.
Injection amount: 100 μL
Standard material for calculating molecular weight: standard polysthylene (Toso Co. ltd.)

Synthesis Example 1

Synthesis of a Salt Represented by the Formula (I1)

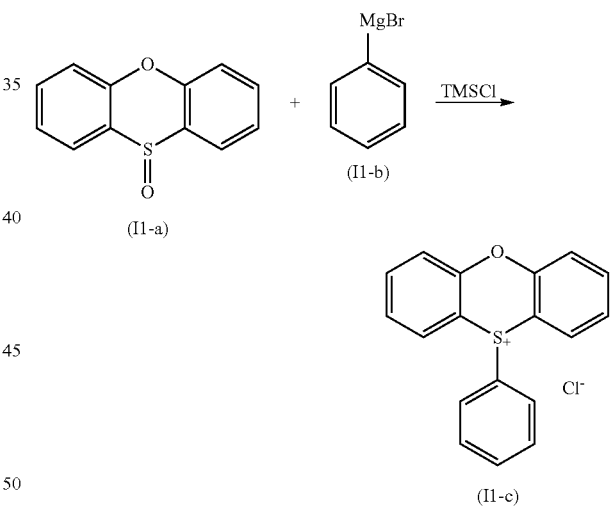

A compound which induces a cation (I) was synthesized.

50.00 parts of the compound represented by the formula (I1-a) and 250 parts of tetrahydrofuran were introduced into a reactor vessel, and the mixture was stirred for 30 minutes at 30° C. Then, 50.23 parts of trimethylsilyl chloride was added into the mixture in the form of drops. The obtained mixture was cooled to 0° C., 157.20 parts of a compound represented by the formula (I1-b) (purity 32%, obtained from Tokyo Chemical Industry Co., LTD) was added thereto in the form of drops over 30 minutes. The temperature of the mixture was elevated to 23° C., and the mixture was stirred for 1 hour at the same temperature. To the obtained reactant, 125 parts of 1N of hydrochloric acid solution was added, and the mixture was stirred, allowed to stand, and then separated to recover an aqueous layer. To the recovered aqueous layer, 125 parts of tert-butyl methyl ether was added, and the obtained solution was stirred, allowed to stand, and then separated to recover an aqueous layer. To the recovered aqueous layer, 125 parts of chloroform was added, and the obtained solution was stirred, allowed to stand, and then separated to recover an organic layer. The recovered organic layer was filtrated, and the filtrate was concentrated. To a residue of concentrate, 28.33 parts of acetonitrile and 354.15 parts of tert-butyl methyl ether were added, and the obtained mixture was stirred for 30 minutes at 23° C., allowed to precipitate. The precipitate was filtrated, resulting in 53.00 parts of the compound represented by the formula (I1-c).

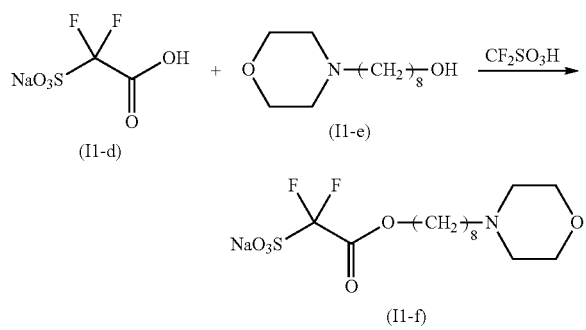

A compound which induces an anion (I) was synthesized.

A compound represented by the formula (I1-d) was synthesized by the method described in JP2006-257078A.

16.80 parts of the compound represented by the formula (I1-d), 18.30 parts of the compound represented by the formula (I1-e) and 250 parts of n-heptane were introduced into a reactor vessel, and the mixture was stirred for 30 minutes at 30° C. Then, 12.80 parts of trifluoroacetic acid was added into the mixture. The temperature of the mixture was elevated, and the mixture was refluxed to dehydrate for 20 hours at 100° C. Thus obtained reactant was cooled to 80° C., 250 parts of acetonitrile was added thereto at the same temperature. The obtained mixture was concentrated. To a residue of concentrate, 290 parts of ethyl acetate was added, and the obtained mixture was stirred for 30 minutes at 23° C., allowed to precipitate. The precipitate was filtrated, resulting in 21.11 parts of the compound represented by the formula (I1-f).

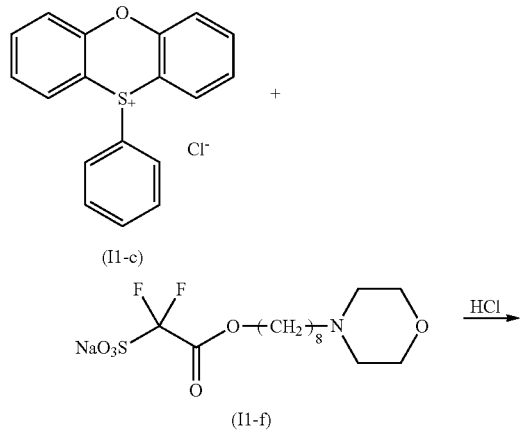

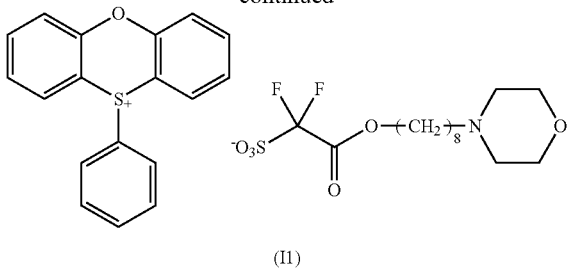

The obtained compound represented by the formula (I1-c) and the compound represented by the formula (I1-f) were used for producing a compound represented by the formula (I1).

26.18 parts of the compound represented by the formula (I1-f) and 147.39 parts of chloroform were introduced into a reactor vessel, and the mixture was stirred for 30 minutes at 30° C. Then, 20.71 parts of the compound represented by the formula (I1-c) and 62.27 parts of ion-exchanged water were added into the mixture. To the obtained mixture, 6.90 parts of 35% of hydrochloric acid solution was added in the form of drops, and the mixture was stirred for 12 hours at 23° C. To the obtained reactant mixture, 12.00 parts of 28% aqueous ammonia was added in the form of drops, and the mixture was separated to recover an organic layer. To the recovered organic layer, 49.13 parts of ion-exchanged water was added, stirred, allowed to stand and separated to wash with water. These washing operations were repeated total five times. To the obtained organic layer, 2.05 parts of activated carbon was added, and the mixture was stirred for 30 minutes at 23° C., and filtrated. The filtrate was concentrated, and to the concentrate, 10.97 parts of acetonitrile and 137.06 parts of tert-butyl methyl ether were added, and the obtained mixture was stirred, and a supernatant was removed. The obtained residue was dissolved in chloroform and concentrate, resulting in 25.50 parts of the salt represented by the formula (I1).

MASS (ESI(+) Spectrum): M$^+$ 277.1
MASS (ESI(−) Spectrum): M$^−$ 372.1

Synthesis Example 2

Synthesis of a Salt Represented by the Formula (I2)

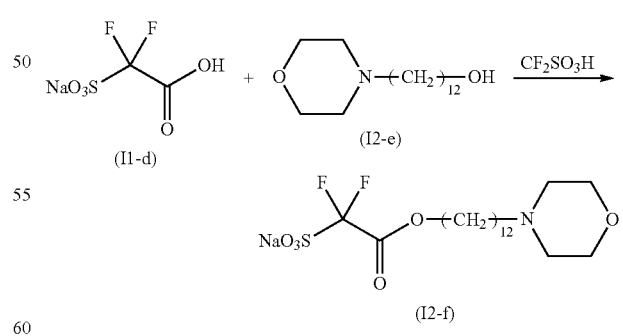

16.80 parts of the compound represented by the formula (I1-d), 23.07 parts of the compound represented by the formula (I2-e) and 250 parts of n-heptane were introduced into a reactor vessel, and the mixture was stirred for 30 minutes at 30° C. Then, 12.80 parts of trifluoroacetic acid was added into the mixture. The temperature of the mixture was elevated, and the mixture was refluxed to dehydrate for 20 hours at 100° C. Thus obtained reactant was cooled to 80° C., 250 parts of acetonitrile was added thereto at the same temperature. The obtained mixture was concentrated. To a residue of concentrate, 290 parts of ethyl acetate was added, and the obtained mixture was stirred for 30 minutes at 23° C., allowed to precipitate. The precipitate was filtrated, resulting in 22.18 parts of the compound represented by the formula (I2-f).

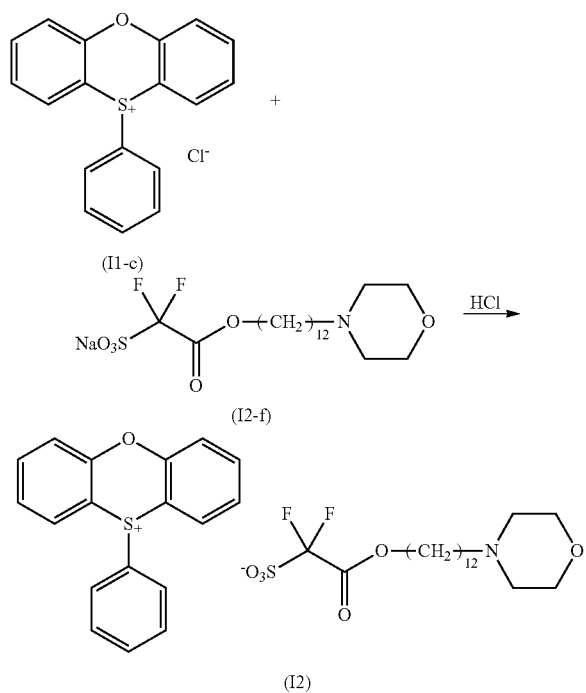

14.95 parts of the compound represented by the formula (I2-0 and 74.73 parts of chloroform were introduced into a reactor vessel, and the mixture was stirred for 30 minutes at 30° C. Then, 10.36 parts of the compound represented by the formula (I1-c) and 31.07 parts of ion-exchanged water were added into the mixture. To the obtained mixture, 3.45 parts of 35% of hydrochloric acid solution was added in the form of drops, the mixture was stirred for 12 hours at 23° C. To the obtained reactant mixture, 6.00 parts of 28% aqueous ammonia was added, and the mixture was separated to recover an organic layer. To the recovered organic layer, 25 parts of ion-exchanged water was added, stirred, allowed to stand and separated to wash with water. These washing operations were repeated total five times. To the obtained organic layer, 1.00 parts of activated carbon was added, and the mixture was stirred for 30 minutes at 23° C., and filtrated. The filtrate was concentrated, and to the concentrate, 6 parts of acetonitrile and 80 parts of tert-butyl methyl ether were added, and the obtained mixture was stirred, and a supernatant was removed. The obtained residue was dissolved in chloroform and concentrate, resulting in 13.10 parts of the salt represented by the formula (I2).

MASS (ESI(+) Spectrum): M⁺ 277.1
MASS (ESI(-) Spectrum): M⁻ 428.2

Synthesis Example 3

Synthesis of a Salt Represented by the Formula (I11)

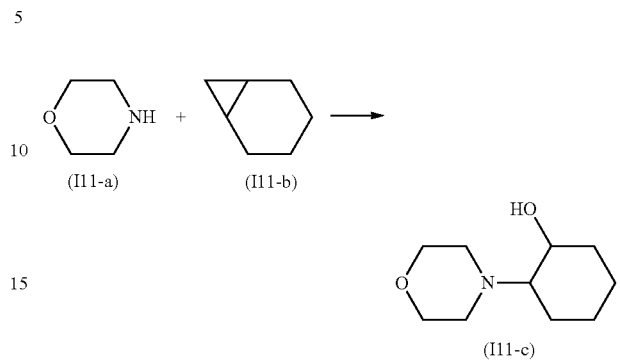

46.60 parts of the compound represented by the formula (I11-a), 27.54 parts of ion-exchanged water and 50.00 parts of the compound represented by the formula (I11-b) were introduced into a reactor vessel, and the mixture was heated to reflux for 2 hours at 105° C. The obtained mixture was cooled to 23° C. To the obtained mixture, 450 parts of saturated sodium hydroxide and 400 parts of tert-butyl methyl ether were added, the mixture was stirred, and separated to obtain an organic layer. To the obtained organic layer, 5.00 parts of magnesium sulfate was added, stirred for 30 minutes at 23° C., and filtrated. The filtrate was distilled under reduced pressure to separate a liquid which contains a boiling point of 104 to 107° C./2 to 3 mmHg, resulting in 62.69 parts of the compound represented by the formula (I11-c).

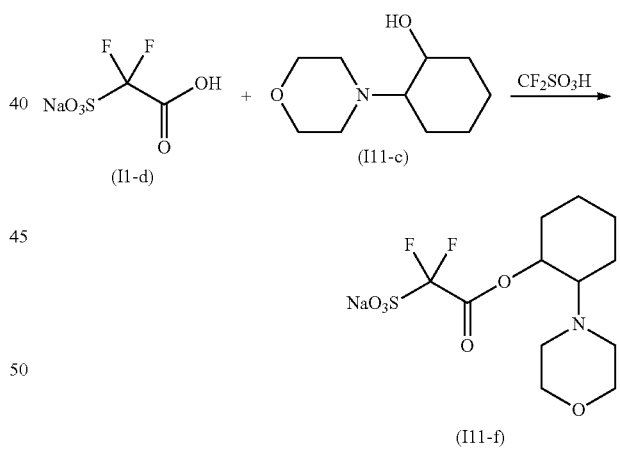

16.80 parts of the compound represented by the formula (I1-d), 15.75 parts of the compound represented by the formula (I11-c) and 250 parts of tert-butyl methyl ether were introduced into a reactor vessel, and the mixture was stirred for 30 minutes at 30° C. Then, 12.80 parts of trifluoroacetic acid was added into the mixture. The temperature of the mixture was elevated, and the mixture was refluxed to dehydrate for 20 hours at 100° C. Thus obtained reactant was cooled to 80° C., 250 parts of acetonitrile was added thereto at the same temperature. The obtained mixture was concentrated, resulting in the compound represented by a residue containing the compound represented by the formula (I11-f).

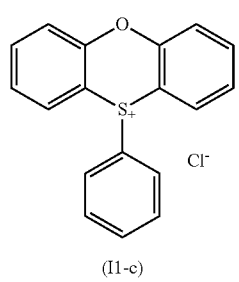

(I1-c)

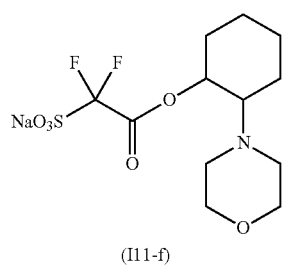

(I11-f)

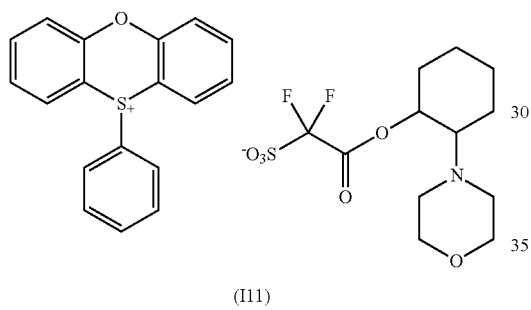

(I11)

To the residue containing the compound represented by the formula (I11-f), 75 parts of chloroform was charged, and stirred for 30 minutes at 30° C. To the obtained reactant, 10.36 parts of a compound represented by the formula (I1-c) and 31.07 parts of ion-exchanged water were added. Then to the obtained mixture, 3.45 parts of 35% hydrochloride was added in the form of drops, and stirred for 12 hours at 23° C. To the obtained reactant, 6.00 parts of 28% aqueous ammonium was added in the form of drops, the obtained mixture was separated to obtain an organic layer. To the obtained organic layer, 25 parts of ion-exchanged water was added, stirred, allowed to stand and separate to wash with water. These washing operations were repeated total five times. To the obtained organic layer, 1.00 parts of activated carbon was added, stirred for 30 minutes at 23° C., and filtrated. The filtrate was concentrated to obtain a concentrate, to this concentrate, 100 parts of acetonitrile was mixed to dissolve, and concentrated. To the obtained residue, 200 parts of tert-butyl methyl ether was added, stirred for 30 minutes, and filtrated, resulting in 9.83 parts of the salt represented by the formula (III).

MASS (ESI(+) Spectrum): M$^+$ 277.1
MASS (ESI(−) Spectrum): M$^−$ 342.1

Synthetic Example of the Resin
The monomers used the synthesis of the resin are shown below.

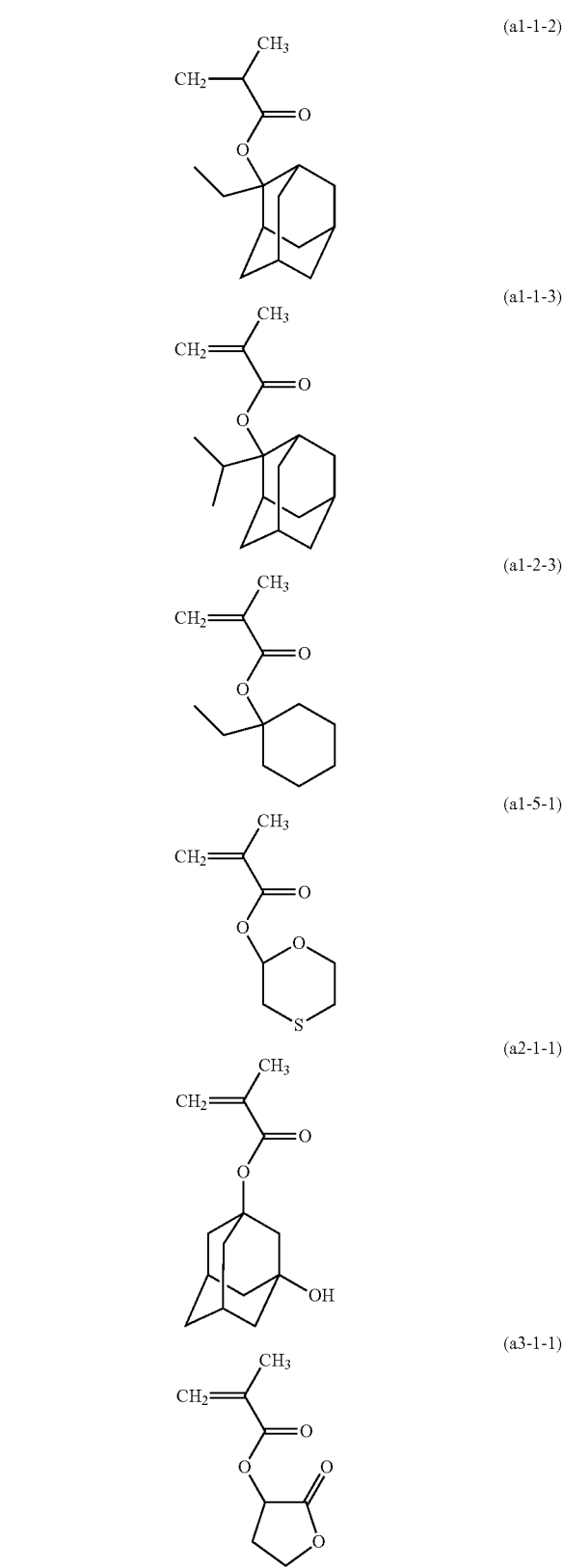

(a3-2-3)

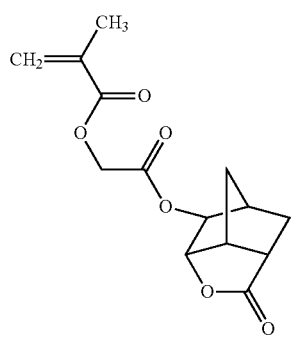

Synthesis of Resin A1

Monomer (a1-1-3), monomer (a1-2-3), monomer (a2-1-1), monomer (a3-1-1) and monomer (a3-2-3) were mixed together with a mole ratio of monomer (a1-1-3):monomer (a1-2-3):monomer (a2-1-1):monomer (a3-1-1):monomer (a3-2-3)=30:14:6:20:30, and dioxane was added thereto in an amount equal to 1.5 times by weight of the total amount of monomers to obtain a solution. Azobisisobutyronitrile and azobis(2,4-dimethylvaleronitrile) was added as an initiator to obtain a solution in an amount of 1 mol % and 3 mol % respectively with respect to the entire amount of monomers, and the resultant mixture was heated for about 5 hours at 73° C. After that, the obtained reacted mixture was poured into a large amount of methanol/water mixed solvent to precipitate a resin. Thus obtained resin was dissolved in another dioxane to obtain a solution, and the solution was poured into a mixture of methanol/water mixed solvent to precipitate a resin. The obtained resin was filtrated. These operations were repeated for two times, resulting in a 65% yield of copolymer having a weight average molecular weight of about 8100. This copolymer, which had the structural units of the following formula, was referred to Resin A1.

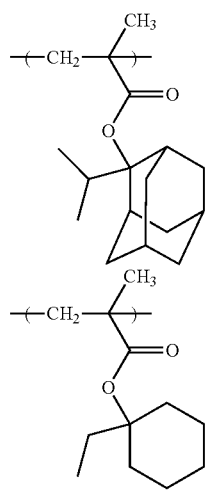

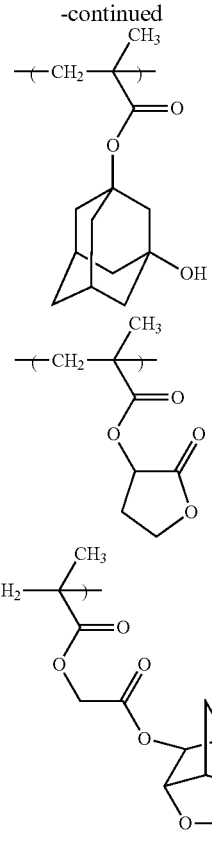

Synthesis of Resin A2

Monomer (a1-1-2), monomer (a2-1-1) and monomer (a3-1-1) were mixed together with a mole ratio of monomer (a1-1-2):monomer (a2-1-1):monomer (a3-1-1)=50:25:25, and dioxane was added thereto in an amount equal to 1.5 times by weight of the total amount of monomers to obtain a solution. Azobisisobutyronitrile and azobis(2,4-dimethylvaleronitrile) was added as an initiator to obtain a solution in an amount of 1.0 mol % and 3.0 mol % respectively with respect to the entire amount of monomers, and the resultant mixture was heated for about 8 hours at 80° C. After that, the obtained reacted mixture was poured into a mixture of a large amount of methanol and water to precipitate a resin. The obtained resin was filtrated. Thus obtained resin was dissolved in another dioxane to obtain a solution, and the solution was poured into a mixture of methanol and water to precipitate a resin. The obtained resin was filtrated. These operations were repeated three times, resulting in a 60% yield of copolymer having a weight average molecular weight of about 9200. This copolymer, which had the structural units of the following formula, was referred to Resin A2.

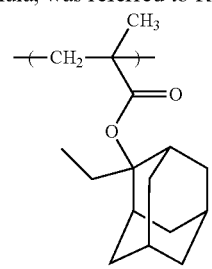

Synthesis of Resin A3

Monomer (a1-1-3), monomer (a1-2-3), monomer (a2-1-1), monomer (a3-2-3) and monomer (a3-1-1) were mixed together with a mole ratio of monomer (a1-1-3):monomer (a1-2-3):monomer (a2-1-1):monomer (a3-2-3):monomer (a3-1-1)=30:14:6:20:30, and dioxane was added thereto in an amount equal to 1.5 times by weight of the total amount of monomers to obtain a solution. Azobisisobutyronitrile and azobis(2,4-dimethylvaleronitrile) was added as an initiator to obtain a solution in an amount of 1 mol % and 3 mol % respectively with respect to the entire amount of monomers, and the resultant mixture was heated for about 5 hours at 75° C. After that, the obtained reacted mixture was poured into a mixture of a large amount of methanol and water to precipitate a resin. The obtained resin was filtrated. Thus obtained resin was dissolved in another dioxane to obtain a solution, and the solution was poured into a large amount of a mixture of methanol and water to precipitate a resin. The obtained resin was filtrated. These operations were repeated two times, resulting in a 60% yield of copolymer having a weight average molecular weight of about 7000. This copolymer, which had the structural units of the following formula, was referred to Resin A3.

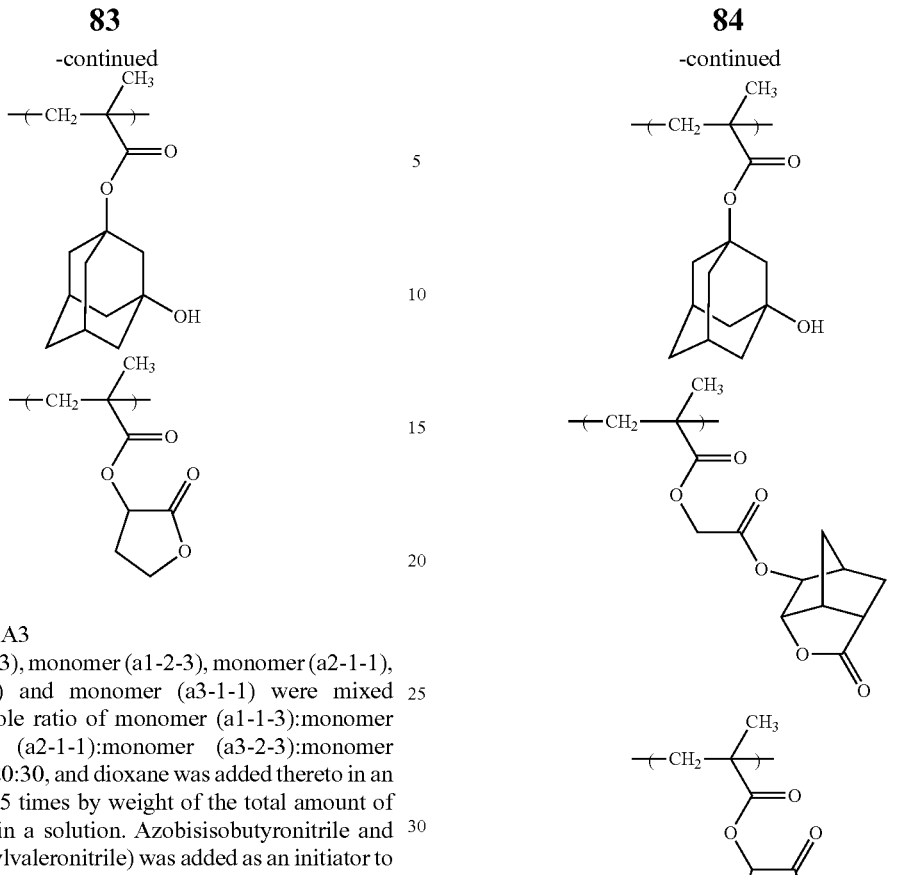

Synthesis of Resin A4

Monomer (a1-1-3), monomer (a1-5-1), monomer (a2-1-1), monomer (a3-2-3) and monomer (a3-1-1) were mixed together with a mole ratio of monomer (a1-1-3):monomer (a1-5-1):monomer (a2-1-1):monomer (a3-2-3):monomer (a3-1-1)=30:14:6:20:30, and dioxane was added thereto in an amount equal to 1.5 times by weight of the total amount of monomers to obtain a solution. Azobisisobutyronitrile and azobis(2,4-dimethylvaleronitrile) was added as an initiator to obtain a solution in an amount of 1 mol % and 3 mol % respectively with respect to the entire amount of monomers, and the resultant mixture was heated for about 5 hours at 75° C. After that, the obtained reacted mixture was poured into a mixture of a large amount of methanol and water to precipitate a resin. The obtained resin was filtrated. Thus obtained resin was dissolved in another dioxane to obtain a solution, and the solution was poured into a large amount of a mixture of methanol and water to precipitate a resin. The obtained resin was filtrated. These operations were repeated two times, resulting in a 62% yield of copolymer having a weight average molecular weight of about 7400. This copolymer, which had the structural units of the following formula, was referred to Resin A4.

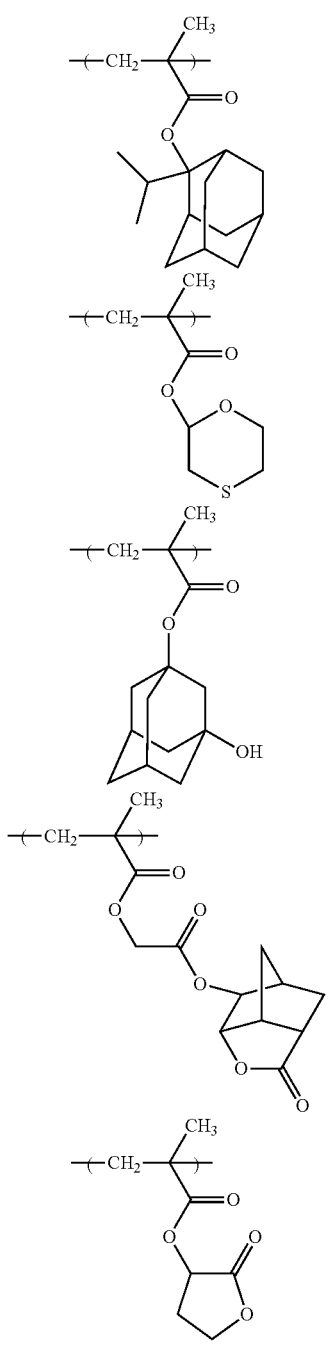

(Preparing Resist Composition)

Resist compositions were prepared by mixing and dissolving each of the components shown in Table 6, and then filtrating through a fluororesin filter having 0.2 μm pore diameter.

TABLE 6

| Ex. | Resin | Acid Generator | Basic Compound | BP/PEB |
|---|---|---|---|---|
| 4 | A1 = 10 | I1/B1 = 0.05/0.85 | — | 100° C./100° C. |
| 5 | A1 = 10 | I1/B2 = 0.05/0.85 | — | 100° C./100° C. |
| 6 | A2 = 10 | I1/B2 = 0.05/0.85 | — | 110° C./110° C. |
| 7 | A1 = 10 | I1/B2 = 0.025/0.85 | C1 = 0.07 | 100° C./100° C. |

TABLE 6-continued

| Ex. | Resin | Acid Generator | Basic Compound | BP/PEB |
|---|---|---|---|---|
| 8 | A2 = 10 | I1/B1 = 0.025/0.85 | C1 = 0.07 | 110° C./110° C. |
| 9 | A3 = 10 | I1/B2 = 0.05/0.85 | — | 100° C./100° C. |
| 10 | A4 = 10 | I1/B2 = 0.05/0.85 | — | 100° C./100° C. |
| 11 | A4 = 10 | I2/B2 = 0.05/0.85 | — | 100° C./100° C. |
| 12 | A4 = 10 | I11/B2 = 0.05/0.85 | — | 100° C./100° C. |
| Comp. Ex.1 | A2 = 10 | B3/B1 = 0.05/0.85 | — | 110° C./110° C. |

(Unit: parts)

<Resin>
Resins Prepared by the Above Synthetic Examples
<Acid Generator>
I1 prepared by the above Synthetic Examples 1
I2 prepared by the above Synthetic Examples 2
I11 prepared by the above Synthetic Example 3
B1:

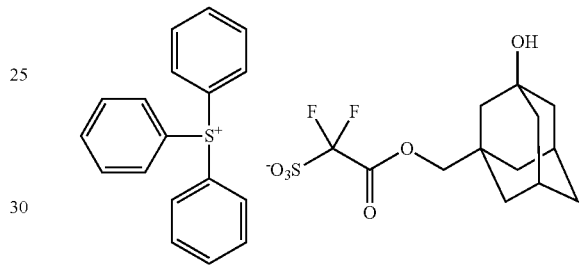

B2: this was prepared by a method according to the method described in the Examples of JP2010-152341A

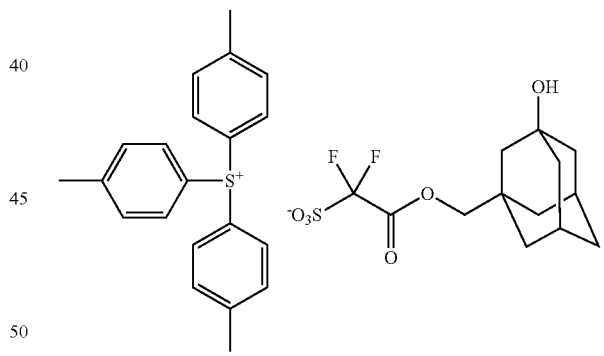

B3: this was prepared by a method according to the method described in the Examples of JP2002-214774A

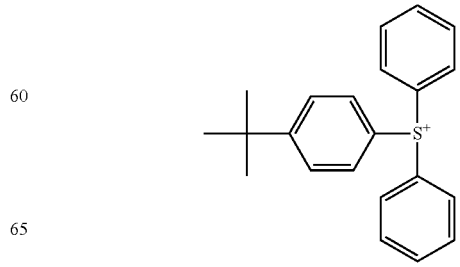

-continued

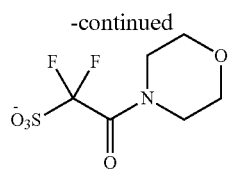

<Basic Compound: Qencher>
C1: 2,6-diisopropylaniline (obtained from Tokyo Chemical Industry Co., LTD)
<Solvent of Resist Composition>

| | |
|---|---|
| Propylene glycol monomethyl ether acetate | 265 parts |
| 2-Heptanone | 20 parts |
| Propylene glycol monomethyl ether | 20 parts |
| γ-butyrolactone | 3.5 parts |

(Producing Resist Pattern)

A composition for an organic antireflective film ("ARC-29", by Nissan Chemical Co. Ltd.) was applied onto 12-inch silicon wafers and baked for 60 seconds at 205° C. to form a 78 nm thick organic antireflective film.

The above resist compositions were then applied thereon by spin coating so that the thickness of the resulting film became 85 nm after drying.

The obtained wafers were then pre-baked for 60 sec on a direct hot plate at the temperatures given in the "PB" column in Table 6 to obtain a composition layer.

Contact hole patterns (hole pitch: 100 nm, hole diameter: 70 nm) were then exposed through stepwise changes in exposure quantity using an ArF excimer stepper for immersion lithography ("XT: 1900Gi" by ASML Ltd.: NA=1.35, 3/4 Annular, X-Y deflection), on the wafers on which the composition layer thus been formed.

The exposure was followed by 60 seconds of post-exposure baking at the temperatures given in the "PEB" column in Table 6. The ultrapure water was used as medium of immersion.

This was followed by 60 sec of puddle development with 2.38 wt % tetramethylammonium hydroxide aqueous solution to obtain a resist pattern.

Effective sensitivity was represented as the exposure amount at which a 70 nm hole diameter resolved to 55 nm hole diameter with the each resist film.

(Focus Margin (DOF) Evaluation)

For the effective sensitivity, when the focus fluctuated with a standard hole diameter as the range of 55 nm±5% (52.5 to 57.5 nm).

Table 7 illustrates the results thereof. The parenthetical number means DOF values.

TABLE 7

| | DOF(μm) |
|---|---|
| Ex. 4 | 0.21 |
| Ex. 5 | 0.24 |
| Ex. 6 | 0.18 |
| Ex. 7 | 0.18 |
| Ex. 8 | 0.15 |
| Ex. 9 | 0.24 |
| Ex. 10 | 0.24 |
| Ex. 11 | 0.24 |
| Ex. 12 | 0.24 |
| Comparative Ex. 1 | 0.09 |

According to the resist composition of the present invention, it is possible to achieve satisfactory wide focus margin (DOF) in the obtained resist pattern. Therefore, the present resist composition can be used for semiconductor microfabrication.

What is claimed is:
1. A salt represented by the formula (I)

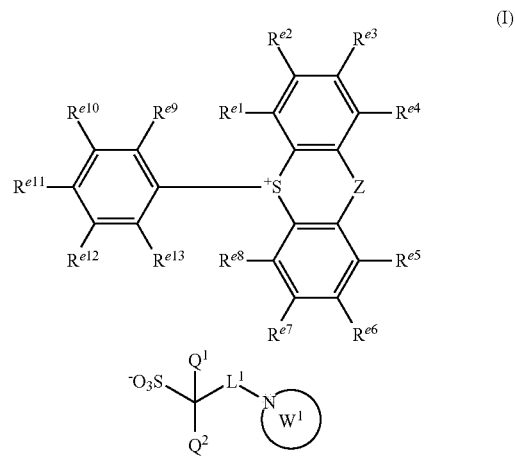

wherein $Q^1$ and $Q^2$ independently represent a fluorine atom or a $C_1$ to $C_6$ perfluoroalkyl group;

$L^1$ represents *—CO—O—$L^a$- or *—$CH_2$—O-$L^b$-, * represents a bond to —$CQ^1Q^2$, $L^a$ and $L^b$ independently represent a $C_1$ to $C_{15}$ divalent saturated aliphatic hydrocarbon group, and one or more —$CH_2$— contained in the divalent saturated aliphatic hydrocarbon group may be replaced by —O— or —CO—;

ring $W^1$ represents a $C_2$ to $C_{36}$ non-aromatic heterocyclic ring, and one or more —$CH_2$-contained in the heterocyclic ring may be replaced by —O—;

$R^{e1}$, $R^{e2}$, $R^{e3}$, $R^{e4}$, $R^{e5}$, $R^{e6}$, $R^{e7}$, $R^{e8}$, $R^{e9}$, $R^{e10}$, $R^{e11}$, $R^{e12}$ and $R^{e13}$ independently represent a hydrogen atom, a halogen atom, a hydroxy group, a $C_1$ to $C_{12}$ hydrocarbon group or carboxyl group, or two of $R^{e1}$, $R^{e2}$, $R^{e3}$, $R^{e4}$, $R^{e5}$, $R^{e6}$, $R^{e7}$, $R^{e8}$, $R^{e9}$, $R^{e10}$, $R^{e11}$, $R^{e12}$ and $R^{e13}$, which two respectively bond to adjacent carbon atoms, may form a ring together with two carbon atoms bonded thereto, and one or more —$CH_2$— contained in the hydrocarbon group may be replaced by —O— or —CO—;

Z represents a single bond or a divalent linking group.

2. The salt according to claim 1, wherein Z in the formula (I) is an oxygen atom.

3. The salt according to claim 1, wherein $L^1$ in the formula (I) is a *—CO—O-$L^a$, wherein $L^a$ is defined as claim 1.

4. An acid generator comprising the salt according to claim 1.

5. A resist composition comprising;
the acid generator according to claim 4, and
a resin.

6. The resist composition according to claim 5, wherein the resin is insoluble or poorly soluble in alkali aqueous solution, but becoming soluble in an alkali aqueous solution by the action of an acid.

7. The resist composition according to claim 5, which further comprises a basic compound.

8. The resist composition according to claim 5, which further comprises a solvent.

9. A method for producing resist pattern comprising steps of;
- (1) applying the resist composition of claim 5 onto a substrate;
- (2) drying the applied composition to form a composition layer;
- (3) exposing the composition layer;
- (4) heating the exposed composition layer, and
- (5) developing the heated composition layer.

* * * * *